(12) United States Patent
Sukovich et al.

(10) Patent No.: US 12,195,790 B2
(45) Date of Patent: *Jan. 14, 2025

(54) METHODS FOR IMPROVED IN SITU DETECTION OF NUCLEIC ACIDS AND SPATIAL ANALYSIS

(71) Applicant: 10x Genomics, Inc., Pleasanton, CA (US)

(72) Inventors: David Sukovich, Oakland, CA (US); Felice Alessio Bava, Rome (IT); Augusto Manuel Tentori, Dublin, CA (US); Hanyoup Kim, Foster City, CA (US); Amanda Janesick, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,582

(22) Filed: Sep. 7, 2023

(65) Prior Publication Data

US 2023/0416808 A1    Dec. 28, 2023

Related U.S. Application Data

(63) Continuation of application No. PCT/US2022/051539, filed on Dec. 1, 2022.

(60) Provisional application No. 63/348,752, filed on Jun. 3, 2022, provisional application No. 63/284,835, filed on Dec. 1, 2021.

(51) Int. Cl.
*C12Q 1/68* (2018.01)
*C12Q 1/6841* (2018.01)

(52) U.S. Cl.
CPC ................... *C12Q 1/6841* (2013.01)

(58) Field of Classification Search
USPC ............ 435/6.1, 6.11, 6.12, 91.1, 91.2, 183, 435/287.1, 287.2; 436/94, 501; 536/23.1, 24.3, 24.33
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |

(Continued)

FOREIGN PATENT DOCUMENTS

| | | |
|---|---|---|
| AU | 2003200718 | 10/2006 |
| CA | 3054046 | 3/2020 |

(Continued)

OTHER PUBLICATIONS

Pei, How Do Biomolecules Cross the Cell Membrane? Acc. Chem. Res., 55, 309-318, 2022.*

(Continued)

*Primary Examiner* — Frank W Lu
(74) *Attorney, Agent, or Firm* — Fish & Richardson P.C.

(57) ABSTRACT

Provided herein are methods, compositions, and systems for improved in situ detection of analytes and spatial analysis using, e.g., a sequencing readout.

27 Claims, 28 Drawing Sheets

(56) References Cited

U.S. PATENT DOCUMENTS

| | | |
|---|---|---|
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,559,032 A | 9/1996 | Pomeroy |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,716,825 A | 2/1998 | Hancock et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,083,761 A | 7/2000 | Kedar et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,306,597 B1 | 10/2001 | Macevicz |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,544,790 B1 | 4/2003 | Sabatini |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,673,620 B1 | 1/2004 | Loeffler |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 6,969,488 B2 | 11/2005 | Bridgham |
| 7,011,944 B2 | 3/2006 | Prudent et al. |
| 7,057,026 B2 | 6/2006 | Barnes |
| 7,083,980 B2 | 8/2006 | Reznikoff et al. |
| 7,098,041 B2 | 8/2006 | Kaylor et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,700,286 B2 | 4/2010 | Stroun et al. |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,207,093 B2 | 6/2012 | Szostak |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |

(56) References Cited

U.S. PATENT DOCUMENTS

| | | |
|---|---|---|
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,951,781 B2 | 2/2015 | Reed |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,557,330 B2 | 1/2017 | Siciliano et al. |
| 9,574,230 B2 | 2/2017 | Van Eijk |
| 9,582,877 B2 | 2/2017 | Fu |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,138,509 B2 | 11/2018 | Church et al. |
| 10,144,966 B2 | 12/2018 | Cantor |
| 10,179,932 B2 | 1/2019 | Church et al. |
| 10,208,982 B2 | 2/2019 | Bannish et al. |
| 10,227,639 B2 | 3/2019 | Levner et al. |
| 10,266,888 B2 | 4/2019 | Daugharthy et al. |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,545,075 B2 | 1/2020 | Deisseroth et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |

(56) References Cited

U.S. PATENT DOCUMENTS

| | | | |
|---|---|---|---|
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 * | 1/2024 | Kim .................. C12Q 1/6841 |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0150909 A1 | 10/2002 | Stuelpnagel |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0175844 A1 | 9/2003 | Nadler et al. |
| 2003/0211489 A1 | 11/2003 | Shen et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082058 A1 | 4/2004 | Schleifer et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0116161 A1 | 6/2005 | Hafeman et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0164490 A1 | 7/2006 | Kim et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0116612 A1 | 5/2007 | Williamson |
| 2007/0128071 A1 | 6/2007 | Shea et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |

(56) References Cited

U.S. PATENT DOCUMENTS

| | | |
|---|---|---|
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0145616 A1 | 6/2008 | Gharib et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0270273 A1 | 10/2009 | Burns et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2009/0321262 A1 | 12/2009 | Adachi et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2010/0282617 A1 | 11/2010 | Rothberg et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0177543 A1 | 7/2012 | Battrell |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0270305 A1 | 10/2012 | Reed et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0052331 A1 | 2/2013 | Kram et al. |
| 2013/0053273 A1 | 2/2013 | Juncker et al. |
| 2013/0065768 A1 | 3/2013 | Zheng et al. |
| 2013/0079232 A1 | 3/2013 | Kain et al. |
| 2013/0096033 A1 | 4/2013 | Routenberg |
| 2013/0171621 A1 | 7/2013 | Luo et al. |
| 2013/0244884 A1 | 9/2013 | Jacobson et al. |
| 2013/0260372 A1 | 10/2013 | Buermann et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0148239 A1 | 5/2015 | Jon |
| 2015/0219618 A1 | 8/2015 | Krishnan et al. |
| 2015/0292988 A1 | 10/2015 | Bharadwaj et al. |
| 2015/0344942 A1 | 12/2015 | Frisen et al. |
| 2015/0368704 A1* | 12/2015 | Fan .................. C12Q 1/6874 506/4 |
| 2016/0019337 A1 | 1/2016 | Roberts et al. |
| 2016/0024555 A1 | 1/2016 | Church et al. |
| 2016/0024576 A1 | 1/2016 | Chee |
| 2016/0033496 A1 | 2/2016 | Chou et al. |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0299165 A1 | 10/2016 | Zhou |
| 2016/0305856 A1 | 10/2016 | Boyden et al. |
| 2016/0333403 A1 | 11/2016 | Chee |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0159109 A1 | 6/2017 | Zheng et al. |
| 2017/0166962 A1 | 6/2017 | van Eijk et al. |
| 2017/0212983 A1 | 7/2017 | Cai et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0275669 A1 | 9/2017 | Weissleder et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0095067 A1 | 4/2018 | Huff et al. |
| 2018/0104694 A1 | 4/2018 | Huff et al. |
| 2018/0104964 A1 | 4/2018 | Uemura et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |

(56) References Cited

U.S. PATENT DOCUMENTS

| | | |
|---|---|---|
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0217094 A1 | 8/2018 | Herr et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0251833 A1 | 9/2018 | Daugharthy et al. |
| 2018/0274039 A1* | 9/2018 | Zhang .................. C12Q 1/6886 |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0249248 A1 | 8/2019 | Beechem et al. |
| 2019/0262831 A1 | 8/2019 | West et al. |
| 2019/0264268 A1 | 8/2019 | Frisen et al. |
| 2019/0264270 A1* | 8/2019 | Zhuang ................. C12Q 1/6841 |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0352708 A1 | 11/2019 | Gaige et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0363408 A1 | 11/2020 | Chou et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |

(56) References Cited

U.S. PATENT DOCUMENTS

| | | |
|---|---|---|
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0416807 A1 | 1/2023 | Chee |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |

FOREIGN PATENT DOCUMENTS

| | | |
|---|---|---|
| CN | 1273609 | 11/2000 |
| CN | 1537953 | 10/2004 |
| CN | 1680604 | 10/2005 |
| CN | 1749752 | 3/2006 |
| CN | 1898398 | 1/2007 |
| CN | 1981188 | 6/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 0961110 | 12/1999 |

(56) References Cited

FOREIGN PATENT DOCUMENTS

| | | |
|---|---|---|
| EP | 0901631 | 8/2004 |
| EP | 1712623 | 10/2006 |
| EP | 1782737 | 5/2007 |
| EP | 1878502 | 1/2008 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013983 | 5/2016 |
| EP | 3013984 | 5/2016 |
| EP | 2350648 | 7/2017 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/113804 | 12/2005 |
| WO | WO 2006/020515 | 2/2006 |
| WO | WO 2006/056861 | 6/2006 |
| WO | WO 2006/064199 | 6/2006 |
| WO | WO 2006/124771 | 11/2006 |
| WO | WO 2006/137733 | 12/2006 |
| WO | WO 2007/010251 | 1/2007 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2008/157801 | 12/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/102903 | 8/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/142841 | 9/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/027367 | 2/2017 |
| WO | WO 2017/048871 | 3/2017 |
| WO | WO 2017/075293 | 5/2017 |
| WO | WO 2017/112957 | 6/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/045186 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/148471 | 8/2018 |
| WO | WO 2018/175779 | 9/2018 |
| WO | WO 2018/209398 | 11/2018 |
| WO | WO 2019/012005 | 1/2019 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/140334 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |

(56) References Cited

FOREIGN PATENT DOCUMENTS

| | | |
|---|---|---|
| WO | WO 2020/028194 | 2/2020 |
| WO | WO 2020/047002 | 3/2020 |
| WO | WO 2020/047004 | 3/2020 |
| WO | WO 2020/047010 | 3/2020 |
| WO | WO 2020/053655 | 3/2020 |
| WO | WO 2020/056381 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/016379 | 1/2021 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/262018 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |

OTHER PUBLICATIONS

U.S. Appl. No. 16/876,709, filed May 18, 2020, Schnall-Levin et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_ VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/

(56) References Cited

OTHER PUBLICATIONS

3GGIfH3RWpd1bFVha1pexR/8baa08d9007157592b65b2cdc7130990/ CG000239_ VisiumSpatialGeneExpression_UserGuide_RevD. pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples, " Nat Methods, Jul. 2013, 10(7):623-9.
Affymetrix, "GeneChip Human Genome U133 Set," retrieved from the Internet: on the World Wide Web at affymetrix.com/support/ technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G.T Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes—Next Generation Tools for Tissue Exploration," Bioessays, Oct. 2020, 42(10):e1900221, 16 pages.
Assets.ctassets.net [online], "Technical Note—Visium Spatial Gene Expression Imaging Guidelines," CG000241 Rev A, 2019, retrieved on Jul. 29, 2022, retrieved from URL <https://assets.ctfassets.net/ an68im79xiti/76JHgFQo6aLq8UPvfL0u2c/ fc39e46f86bf75676d3f7da6dc721fad/CG000241_VisiumImaging-GuidelinesTN_Rev_A.pdf>, 8 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Bell, "A simple way to treat PCR products prior to sequencing using ExoSAP-IT," Biotechniques, 2008, 44(6):834, 1 page.
Belton et al., "Hi-C: A comprehensive technique to capture the conformation of genomes," Methods, Nov. 2012, 58(3):268-276, 16 pages.
Bentley et al., "Accurate whole human genome sequencing using reversible terminator chemistry," Nature, 2008, 456(7218):53-59.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Bibikova et al., "Quantitative gene expression profiling in formalin-fixed paraffin-embedded tissues using universal bead arrays," The American Journal of Pathology, Nov. 1, 2004, 165(5):1799-1807.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Borm et al., "Scalable in situ single-cell profiling by electrophoretic capture of mRNA," bioRxiv, Jan. 2022, 32 pages.
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.

(56) References Cited

OTHER PUBLICATIONS

Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cardona et al., "TrakEM2 0.9a User Manual," Sep. 8, 2011, retrieved on Jul. 29, 2022, retrieved from URL <https://ini.uzh.ch/~acardona/trakem2_manual.html>, 38 pages.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al. "Arrayed profiling of multiple glycans on whole living cell surfaces." Analytical chemistry, Oct. 15, 2013, 85(22):11153-11158.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://biorxiv.org/node/1754517.abstract>, 50 pages.
Choi et al., "Multiplexed detection of mRNA using porosity-tuned hydrogel microparticles," Analytical chemistry, Sep. 28, 2012, 84(21):9370-9378.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)—T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.

(56) References Cited

OTHER PUBLICATIONS

Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Fahy et al., "Design and synthesis of polyacrylamide-based oligonucleotide supports for use in nucleic acid diagnostics," Nucleic Acids Res., Apr. 1993, 21(8):1819-26.
Falconnet et al., "Rapid, Sensitive and Real-Time Multiplexing Platform for the Analysis of Protein and Nucleic-Acid Biomarkers," Anal. Chem., Jan. 7, 2015, 87:1582-1589.
Fan et al., "A versatile assay for high-throughput gene expression profiling on universal array matrices," Genome Research, May 1, 2004, 14(5):878-885.
Fan et al., "Illumina Universal Bead Arrays," Methods in Enzymology, 2006, 410:57-73.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Fredriksson et al., "Protein detection using proximity-dependent DNA ligation assays," Nature Biotech., 20: 473-77, 2002.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Gamper et al., "Gene expression profile of bladder tissue of patients with ulcerative interstitial cystitis," BMC Genomics, Apr. 28, 2009, 10(199):1-17.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Github.com [online], "ST Spot Detector Usage Guide: A Guide to Using the Spatial Transcriptomics Spot Detector 2.0," Jun. 2018, retrieved on Jul. 29, 2022, retrieved from URL <https://github.com/SpatialTranscriptomicsResearch/st_spot_detector/wiki/ST-Spot-Detector-Usage-Guide, 6 pages.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Gyllborg et al., "Hybridization-based in situ sequencing (HybISS) for spatially resolved transcriptomics in human and mouse brain tissue," Nucleic Acids Res., Sep. 29, 2020, 48(19):e112, 11 pages.
Hadrup et al., "Parallel detection of antigen-specific T-cell responses by multidimensional encoding of MHC multimers," Nat. Methods., Jul. 2009, 6(7), 520-526.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.

(56) References Cited

OTHER PUBLICATIONS

Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hobro et al, "An evaluation of fixation methods: Spatial and compositional cellular changes observed by Raman imaging," Vibrational Spectroscopy, Jul. 2017, 91:31-45.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hua et al., "Multi-level transcriptome sequencing identifies COL1A1 as a candidate marker in human heart failure progression," BMC Med., Jan. 2020, 18(1):2, 16 pages.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA, 2008, 105:1176-1181.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Lamture et al., "Direct detection of nucleic acid hybridization on the surface of a charge coupled device," Nucleic Acid Res., Jun. 1994, 22(11):2121-5.
Landegren et al., "A Ligase-Mediated Gene Detection Technique," Science, 1988, 241(4869):1077-1080.

(56) References Cited

OTHER PUBLICATIONS

Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Highly multiplexed subcellular RNA sequencing in situ", Science, 2014, 343(6177):1360-1363.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Levene et al., "Zero-Mode Waveguides for Single-Molecule Analysis at High Concentrations," Science, 2003, 299:682-686.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett., 2008, 33:1026-1028.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Mamedov et al., "Preparing unbiased T-cell receptor and antibody cDNA libraries for the deep next generation sequencing profiling," Frontiers in Immunol., Dec. 23, 2013, 4(456):1-10.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans- chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.

(56) References Cited

OTHER PUBLICATIONS

Moffitt et al., "RNA Imaging with Multiplexed Error-Robust Fluorescence In Situ Hybridization (MERFISH)," Methods Enzymol., 2016, 572:1-49.

Mohsen et al., "The Discovery of Rolling Circle Amplification and Rolling Circle Transcription," Acc Chem Res., Nov. 15, 2016, 49(11):2540-2550, 25 pages.

Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Mulder et al., "CapTCR-seq: hybrid capture for T-cell receptor repertoire profiling," Blood Advances, Dec. 2018, 2(23):3506-3514.

Nadji et al., "Immunohistochemistry of tissue prepared by a molecular-friendly fixation and processing system," Appl Immunohistochem Mol Morphol., Sep. 2005, 13(3):277-82.

Nallur et al., "Signal amplification by rolling circle amplification on DNA microarrays," Nucleic Acids Res., Dec. 1, 2001, 29(23):e118, 9 pages.

Nandakumar et al., "How an RNA Ligase Discriminates RNA versus DNA Damage," Molecular Cell, 2004, 16:211-221.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Navarro et al., "ST viewer: a tool for analysis and visualization of spatial transcriptomics datasets: Supplementary Information," Bioinformatics, Mar. 2019, 1058-1060.

Ncbi.nlm.nih.gov, [online], "Molecular Inversion Probe Assay," available on or before Oct. 14, 2014, via Internet Archive: Wayback Machine URL<https://web.archive.org/web/20141014124037/ https://ncbi.nlm.nih.gov/probe/docs/techmip/>, retrieved on Jun. 16, 2021, retrieved from URL<https://ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niedringhaus et al., "Landscape of next-generation sequencing technologies," Anal Chem., Jun. 2011, 83(12):4327-41.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nilsson et al., "RNA-templated DNA ligation for transcript analysis," Nucleic Acids Res., Jan. 2001, 29(2):578-81.

Nowak, "Entering the Postgenome Era," Science, 1995, 270(5235):368-71.

Ohtsubo et al., "Bacterial insertion sequences," Curr Top Microbiol Immunol., 1996, 204:1-26.

Oksuz et al., "Systematic evaluation of chromosome conformation capture assays," Nature Methods, Sep. 2021, 18:1046-1055.

Olivier, "The Invader assay for SNP genotyping," Mutat. Res., Jun. 2005, 573(1-2):103-110.

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.

Ozsolak et al., "Digital transcriptome profiling from attomole-level RNA samples," Genome Res., Apr. 2010, 20(4):519-25.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger microwells capable of supporting cell spreading and proliferation," Microfluid Nanofluid, 2010, 8:263-268.

Passow et al., "RNAlater and flash freezing storage methods nonrandomly influence observed gene expression in RNAseq experiments," bioRxiv, Jul. 2018, 28 pages.

PCT International Search Report and Written Opinion in International Appln. No. PCT/US2022/051539, dated Jul. 10, 2023, 28 pages.

PCT Invitation to Pay Additional Fees in International Appln. No. PCT/US2022/051539, dated May 16, 2023, 20 pages.

Pellestor et al., "The peptide nucleic acids (PNAs), powerful tools for molecular genetics and cytogenetics," Eur J Hum Genet., Sep. 2004, 12(9):694-700.

Pemov et al., "DNA analysis with multiplex microarray-enhanced PCR," Nucl. Acids Res., Jan. 2005, 33(2):e11, 9 pages.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perler et al., "Intervening sequences in an Archaea DNA polymerase gene," Proc Natl Acad Sci USA, Jun. 1992, 89(12):5577-5581.

Perocchi et al., "Antisense artifacts in transcriptome microarray experiments are resolved by actinomycin D," Nucleic Acids Res., 2007, 35(19):e128, 7 pages.

Petterson et al., "Generations of sequencing technologies," Genomics, 2009, 93(2):105-111.

Picelli et al., "Full-length RNA-seq from single cells using Smart-seq2," Nat Protoc., Jan. 2014, 9(1):171-81.

Picelli et al., "Tn5 transposase and tagmentation procedures for massively scaled sequencing projects," Genome Res., Dec. 2014, 24(12):2033-40.

Et al., "DNA detection using recombination proteins," PLoS Biol., Jul. 2006, 4(7):e204, 7 pages, Piepenburg.

Plasterk, "The Tc1/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

Polsky-Cynkin et al., "Use of DNA immobilized on plastic and agarose supports to detect DNA by sandwich hybridization," Clin. Chem., 1985, 31(9):1438-1443.

Porreca et al., "Polony DNA sequencing," Curr Protoc Mol Biol., Nov. 2006, Chapter 7, Unit 7.8, pp. 7.8.1-7.8.22.

U.S. Appl. No. 61/267,363, filed Dec. 7, 2009, 33 pages.

Qiu et al., "Combination probes with intercalating anchors and proximal fluorophores for DNA and RNA detection," Nucleic Acids Research, Sep. 2016, 44(17):e138, 12 pages.

Raab et al., "Human tRNA genes function as chromatin insulators," EMBO J., Jan. 2012, 31(2):330-50.

Raj et al., "Imaging individual mRNA molecules using multiple singly labeled probes," Nature Methods, Oct. 2008, 5(10):877-879, 9 pages.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Reznikoff, "Tn5 as a model for understanding DNA transposition," Mol Microbiol., Mar. 2003, 47(5):1199-206.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.

Rodriques et al., "Slide-seq: A scalable technology for measuring genome-wide expression at high spatial resolution," Science, 2019, 363(6434):1463-1467.

(56) References Cited

OTHER PUBLICATIONS

Rohland et al., "Partial uracil-DNA-glycosylase treatment for screening of ancient DNA," Phil. Trans. R. Soc. B, Jan. 19, 2015, 370(1660):20130624, 11 pages.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schmidl et al., "ChIPmentation: fast, robust, low-input ChIP-seq for histones and transcription factors," Nature Methods, Oct. 2015, 12:963-965.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A Dna microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Söderberg et al., "Characterizing proteins and their interactions in cells and tissues using the in situ proximity ligation assay," Methods, Jul. 2008, 45(3):227-32.
Sountoulidis et al., "SCRINSHOT, a spatial method for single-cell resolution mapping of cell states in tissue sections, " PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore, " PNAS USA., May 2009, 106(19):7702-7707.
Stoeckius et al., "Simultaneous epitope and transcriptome measurement in single cells," Nature Methods, Jul. 31, 2017, 14(9):865-868.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Su et al., "Restriction enzyme selection dictates detection range sensitivity in chromatin conformation capture-based variant-to-gene mapping approaches," bioRxiv, Dec. 15, 2020, 22 pages.
Sun et al., "Statistical Analysis of Spatial Expression Pattern for Spatially Resolved Transcriptomic Studies," Nature Methods, Jan. 27, 2020, 17(2): 193-200.
Sutherland et al., "Utility of formaldehyde cross-linking and mass spectrometry in the study of protein-protein interactions," J. Mass Spectrom., Jun. 2008, 43(6):699-715.
Svensson et al., "SpatialDE: identification of spatially variable genes," Nature Methods, May 2018, 15:343-346, 15 pages.
Takei et al., "Integrated Spatial Genomics Reveals Global Architecture Of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.

(56) References Cited

OTHER PUBLICATIONS

Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang et al., "Three-dimensional intact-tissue sequencing of single-cell transcriptional states," Science, Jul. 2018, 361(6400):eaat5691, 22 pages.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilbrey-Clark et al., "Cell Atlas technologies and insights into tissue architecture," Biochemical Journal, Apr. 2020, 477(8):1427-1442.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Wong et al., "ST Spot Detector: a web-based application for automatic spot and tissue detection for Spatial Transcriptomics image datasets," Bioinformatics, Jan. 2018, 34(11):1966-1968.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermococcus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.
10xGenomics.com, [online], "Visium Spatial Gene Expression Reagent Kits—User Guide," Sep. 2023, retrieved on Mar. 29, 2024, retrieved

(56) References Cited

OTHER PUBLICATIONS from URL<https://cdn.10xgenomics.com/image/upload/v1695417753/support-documents/CG000239_VisiumSpatialGeneExpression_UserGuide_RevG.pdf>, 70 pages.
Asp et al., "A spatiotemporal organ-wide gene expression and cell atlas of the developing human heart," Cell, Dec. 12, 2019, 179(7):1647-1660.
Kim et al., "Replication of DNA Microarrays Prepared by In Situ Oligonucleotide Polymerization and Mechanical Transfer," Anal Chem., 2007, 79:7267-7274.
Kuhn et al., "A novel, high-performance random array platform for quantitative gene expression profiling," Genome Res, 2004, 14:2347-2356.
Maniatis et al., "Spatiotemporal Dynamics of Molecular Pathology in Amyotrophic Lateral Sclerosis," bioRxiv, Science, 2018, 364(6435), 54 pages.

* cited by examiner

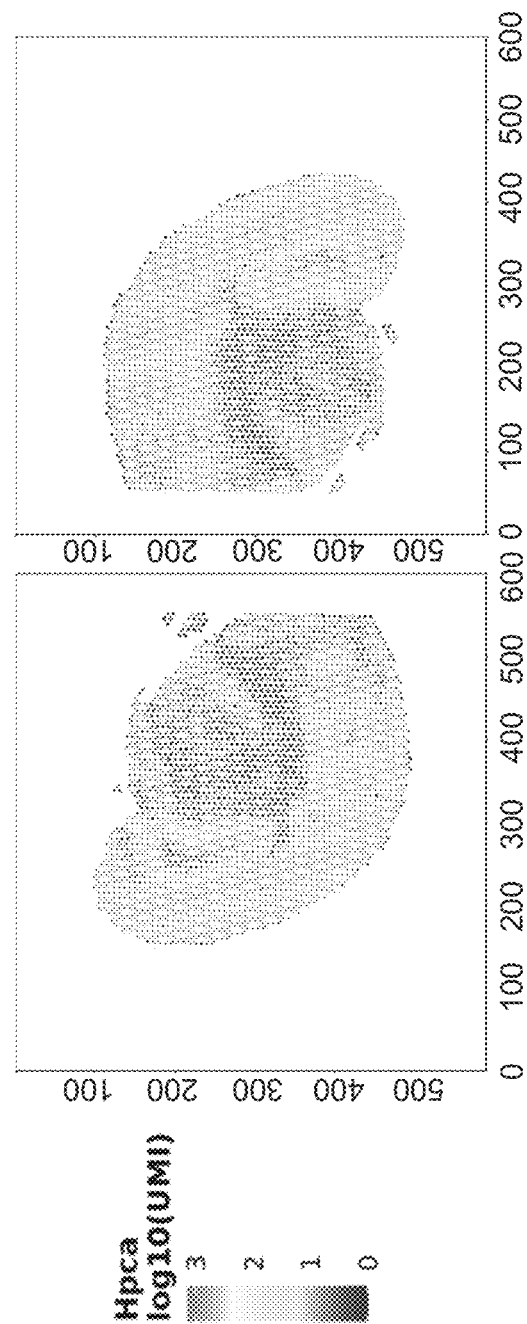

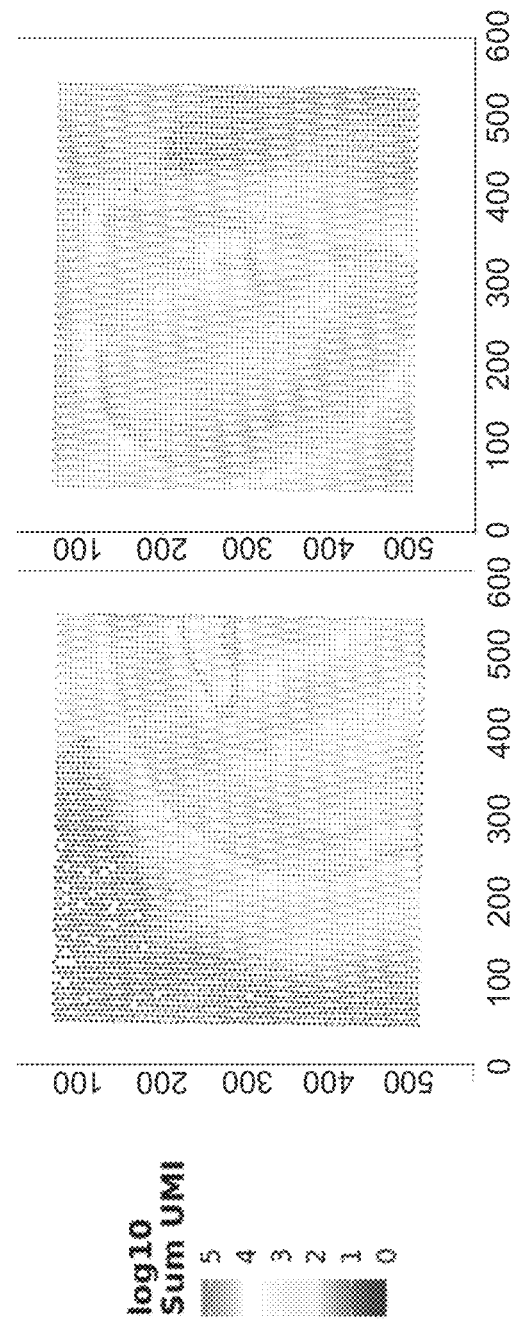

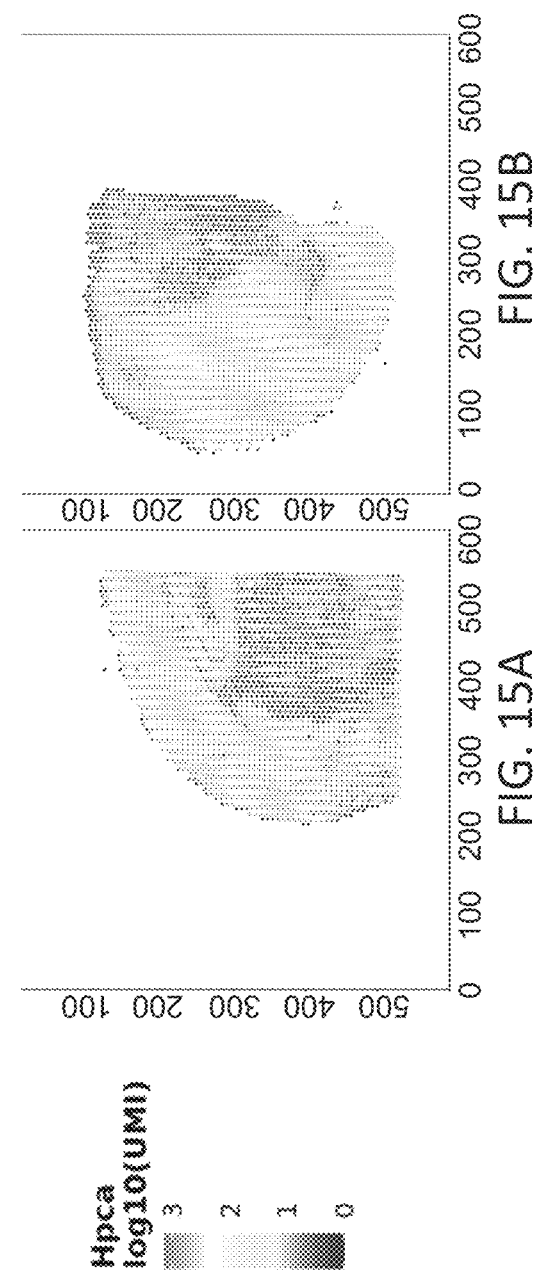

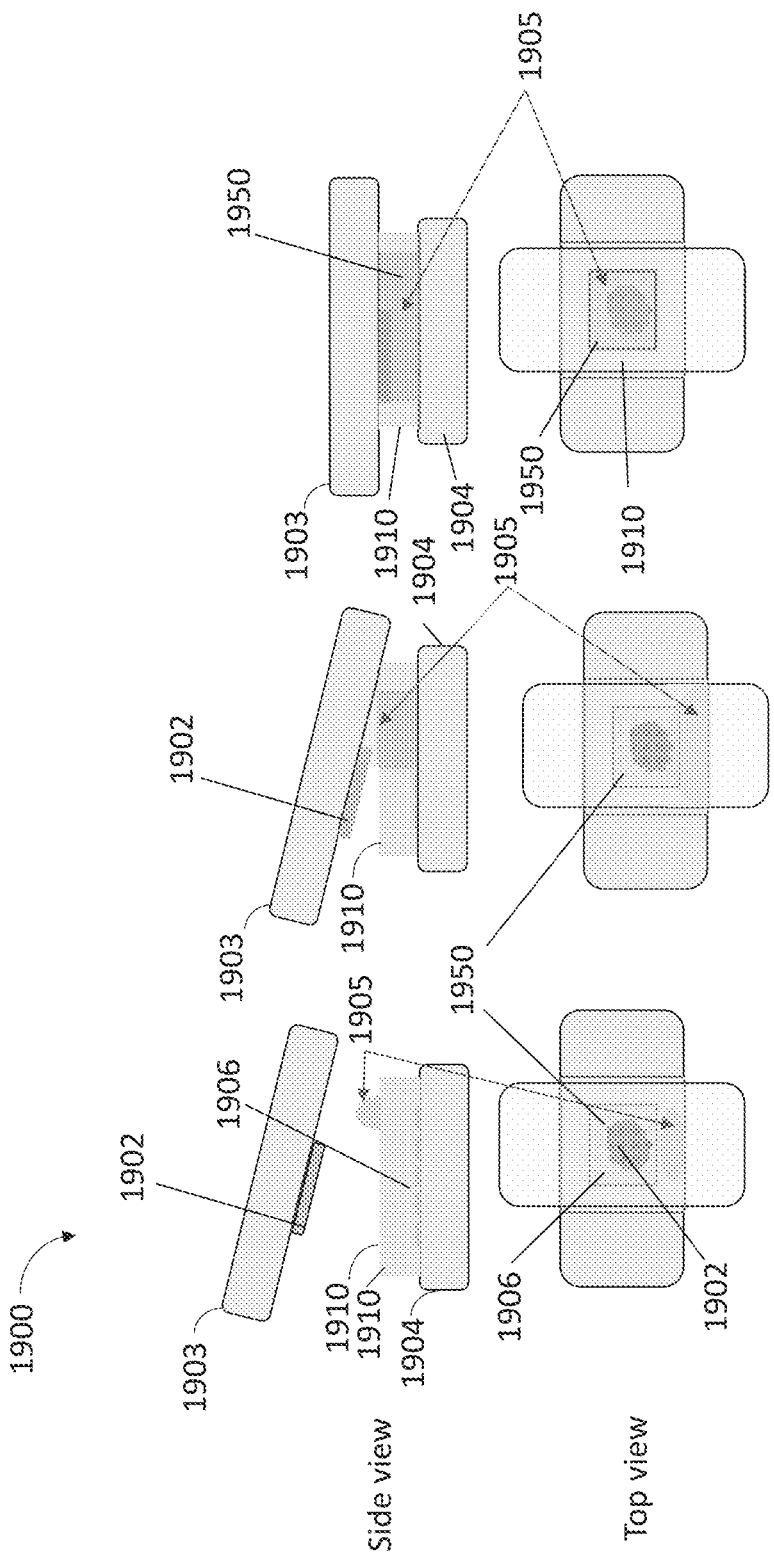

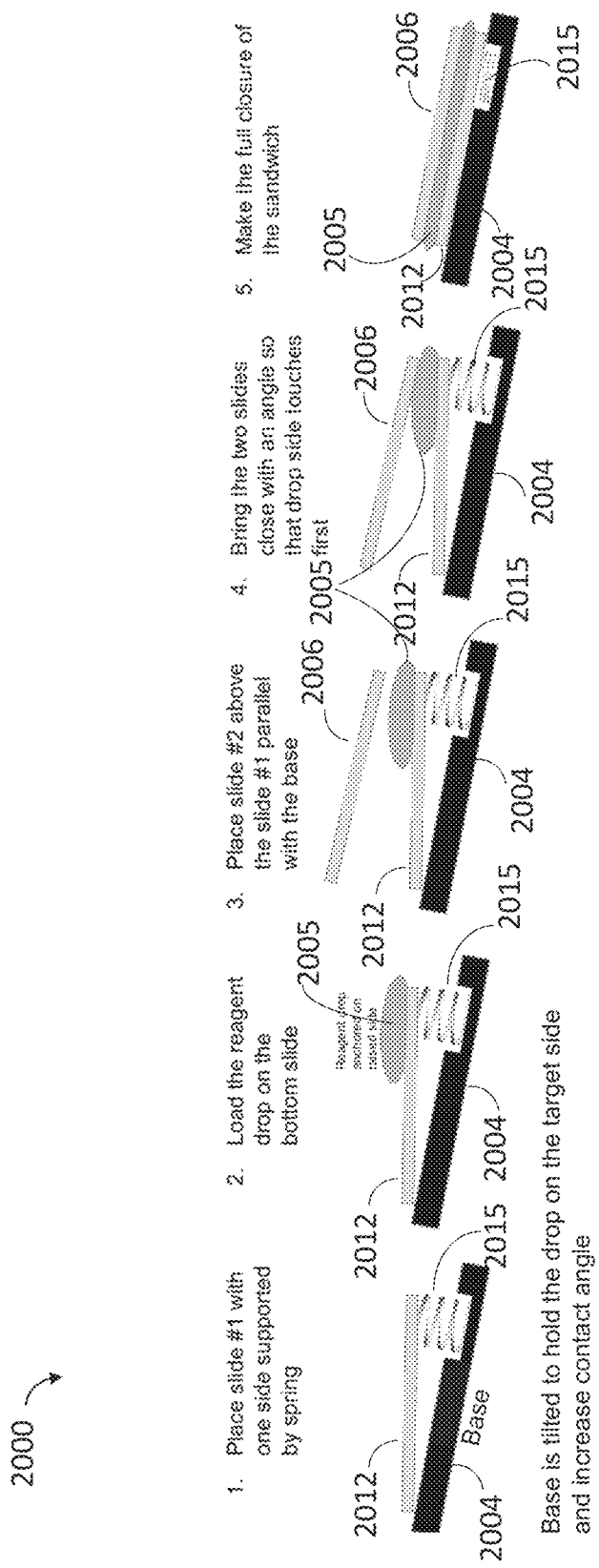

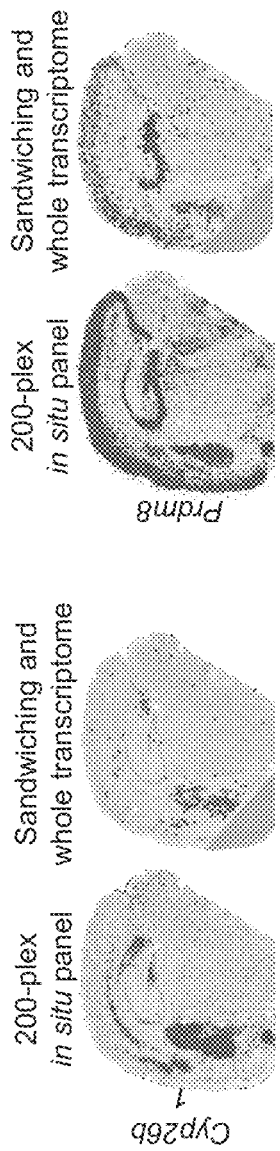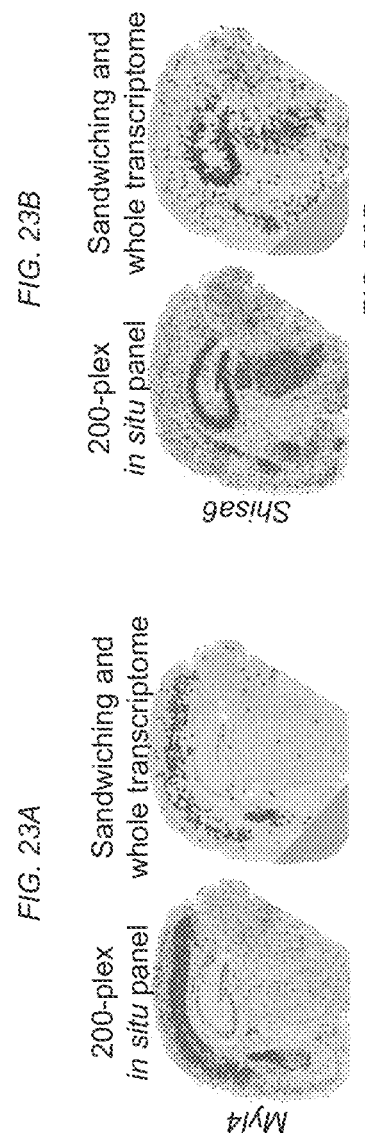
FIG. 23A FIG. 23B FIG. 23C FIG. 23D

METHODS FOR IMPROVED IN SITU DETECTION OF NUCLEIC ACIDS AND SPATIAL ANALYSIS

CROSS-REFERENCE TO RELATED APPLICATIONS

This application is a continuation of PCT Application No. PCT/US2022/051539, filed on Dec. 1, 2022, which claims the benefit of U.S. Provisional Application No. 63/284,835, filed Dec. 1, 2021, and U.S. Provisional Application No. 63/348,752, filed Jun. 3, 2022, the contents of which are incorporated by reference in their entirety herein.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Further, profiling the identity, abundance, and location of analytes within a tissue in situ is useful for understanding the molecular bases of cell identity for developing treatments for diseases. Current in situ hybridization and sequencing-based approaches suffer from low efficiency but the potential value of such in-tissue analysis is significant. Therefore, there exists a need for new and improved methods and systems for in situ analysis paired with spatial analysis to determine the identity, abundance, and distribution of analytes within cells within a tissue. Further, there exists a need for methods to interrogate analytes within cells within a tissue using combinations of in situ and spatial analysis. Spatial analysis of an analyte within a biological sample may require determining the sequence of the analyte sequence or a complement thereof and the sequence of the spatial barcode or a complement thereof to identify the location of the analyte. The biological sample may be placed on a solid support to improve specificity and efficiency when being analyzed for identification or characterization of an analyte, such as DNA, RNA or other genetic material, within the sample.

SUMMARY

The present disclosure features methods, compositions, devices, and systems for determining the location and/or abundance of an analyte in a biological sample. Determining the spatial location and/or abundance of analytes (e.g., proteins, DNA, or RNA) within a biological sample leads to better understanding of spatial heterogeneity in various contexts, such as disease models. Described herein are methods for capturing probes and/or barcodes to a capture domain. In some instances, the techniques disclosed herein facilitate downstream processing, such as sequencing of the probes and/or barcodes bound to a capture domain.

In some examples, the methods disclosed herein utilize RNA-templated ligation (RTL) for analyzing an analyte (e.g., RNA) in a biological sample. In some examples, RTL is used in combination with a "sandwich process," wherein the analyte (or proxy thereof) is transferred from a sample disposed on a first substrate to a second substrate for further downstream processing. In some examples, analyte capture agents are used for analyzing an analyte (e.g., protein) in a biological sample. In some examples, the methods disclosed herein allow spatial analysis of two different types of analytes.

In some embodiments, disclosed herein are methods for analyzing multiple analytes in a biological sample placed on a first substrate, the method comprising: (a) contacting the biological sample with one or more nucleic acid probes that directly or indirectly hybridize to a set of first analytes or complements or amplification products thereof in the biological sample; (b) detecting in the biological sample the one or more nucleic acid probes at a spatial location of the biological sample; (c) hybridizing a first probe and a second probe to a second analyte, wherein the first probe comprises a sequence that is substantially complementary to a first sequence of the second analyte, the second probe comprises a sequence that is substantially complementary to a second sequence of the second analyte, and wherein the second probe comprises a capture probe binding domain; (d) coupling the first probe and the second probe, thereby generating a connected probe; (e) mounting the first substrate on a first member of a support device, the first member configured to retain the first substrate; (f) mounting a second substrate comprising an array on a second member of the support device, the second member configured to retain the second substrate, the array comprising a plurality of capture probes, wherein a capture probe of the plurality of capture probes comprises (i) a spatial barcode and (ii) a capture domain; (g) applying a reagent medium to the first substrate and/or the second substrate; (h) operating an alignment mechanism of the support device to move the first member and/or the second member such that at least a portion of the biological sample is aligned with at least a portion of the array and the portion of the biological sample and the portion of the array contact the reagent medium, and such that the first substrate and the second substrate are separated by a distance of less than 50 micrometers; (i) when the biological sample is aligned with at least a portion of the array, (i) releasing the connected probe from the second analyte and (ii) migrating the connected probe from the biological sample to the array; and (j) hybridizing the connected probe to the capture domain. In some embodiments, the applying step (g) occurs before the mounting steps (e) and (f).

In some embodiments of the method disclosed herein, the first probe and the second probe are on a contiguous nucleic acid sequence. In some embodiments the first probe is on the 3' end of the contiguous nucleic acid sequence and/or the second probe is on the 5' end of the contiguous nucleic acid sequence. In some embodiments, the first and second sequences of the second analyte are adjacent to one another. In some embodiments the first and second sequences of the second analyte are at least 1, 2, 3, 4, 5, 6, 7, 8, 9, 10, or more nucleotides away from one another. In some embodiments the extended first probe comprises a sequence complementary to a sequence between the first and second sequences of the second analyte. In some embodiments an extended second probe is generated using a polymerase, wherein the extended second probe comprises a sequence complementary to a sequence between the first and second sequences of the second analyte.

In some embodiments, the methods disclosed herein further comprise hybridizing a third probe to the first probe and the second probe. In some embodiments the third probe comprises (a) a sequence that is at least 80%, at least 85%, at least 90%, at least 95%, at least 96%, at least 97%, at least 98%, or at least 99%, or 100% complementary to a portion of the first probe that hybridizes to the third probe; and (b) a sequence that is at least 80%, at least 85%, at least 90%, at least 95%, at least 96%, at least 97%, at least 98%, or at least 99%, or 100% complementary to a portion of the second probe that hybridizes to the third probe.

In some embodiments, the coupling the first probe and the second probe comprises ligating via a ligase the first probe and the second probe. In other embodiments the coupling the first probe and the second probe comprises ligating via a ligase: (a) the first probe and the extended second probe; or (b) the extended first probe and the second probe. In some embodiments the ligase is selected from a splintR ligase, a single stranded DNA ligase, or a T4 DNA ligase. In some embodiments the ligase is T4 DNA ligase. In some embodiments, any one or more of steps (a) through (f) of the method further comprise use of a ribonuclease (RNase) inhibitor, optionally wherein step (a) comprises use of the RNase inhibitor.

In some embodiments, the reagent medium comprises an agent for releasing the connected probe and/or the agent for releasing the connected probe comprises a nuclease. In some embodiments the nuclease comprises an RNase, optionally wherein the RNase is selected from RNase A, RNase C, RNase H, or RNase I. In some embodiments the permeabilization agent comprises a protease. In some embodiments the protease is selected from trypsin, pepsin, elastase, or proteinase K. In some embodiments the reagent medium further comprises a detergent. In some embodiments the detergent is selected from sodium dodecyl sulfate (SDS), sarkosyl, saponin, Triton X-100™, or Tween-20™. In some embodiments the reagent medium comprises less than 5 w/v % of a detergent selected from SDS and sarkosyl. In other embodiments the reagent medium comprises at least 5% w/v % of a detergent selected from SDS and sarkosyl. In other embodiments the reagent medium does not comprise sodium dodcyl sulfate (SDS) or sarkosyl. In some embodiments the biological sample and the array are contacted with the reagent medium for about 1-60 minutes. In embodiments the biological sample and the array are contacted with the reagent medium for about 30 minutes. In some embodiments the reagent medium further comprises polyethylene glycol (PEG).

In some embodiments the methods disclosed herein further comprise determining (i) all or a part of the sequence of the connected probe, or a complement thereof, and (ii) the spatial barcode, or a complement thereof, optionally wherein the method further comprises using the determined sequence of (i) and (ii) to determine the location and abundance of the second analyte in the biological sample. In some embodiments the determining comprises sequencing (i) all or a part of the sequence of the connected probe, or a complement thereof, and (ii) the spatial barcode, or a complement thereof. In some embodiments the sequence of the connected probe comprises the sequence of the spatial barcode or the reverse complement thereof, and a sequence corresponding to the second analyte in the biological sample or reverse complement thereof.

In some embodiments, the set of first analytes comprises an RNA analyte. In some embodiments the first analyte is an mRNA analyte. In some embodiments the set of first analytes comprises a DNA analyte. In some embodiments the DNA analyte is genomic DNA. In some embodiments the second analyte is RNA. In some embodiments the second analyte is mRNA. In some embodiments the one or more nucleic acid probes directly hybridize to a first analyte in the set of first analytes or the complement or the amplification product thereof In other embodiments the one or more nucleic acid probes indirectly hybridize to a first analyte in the set of first analytes or the complement or the amplification product thereof.

In some embodiments, the method disclosed herein allows for analyzing multiple analytes in a biological sample placed on a first substrate, the method comprising: (a) contacting the biological sample with one or more nucleic acid probes that directly or indirectly hybridize to a first analyte or a complement or an amplification product thereof in the biological sample, wherein the multiple analytes comprise the first analyte and a second analyte; (b) detecting in the biological sample the one or more nucleic acid probes at a spatial location of the biological sample; (c) contacting the biological sample with a plurality of analyte capture agents, wherein an analyte capture agent of the plurality of analyte capture agents comprises an analyte binding moiety and a capture agent barcode domain, wherein the analyte binding moiety specifically binds to the second analyte, and wherein the capture agent barcode domain comprises an analyte binding moiety barcode and a capture handle sequence; (d) mounting the first substrate on a first member of a support device, the first member configured to retain the first substrate; (e) mounting a second substrate comprising an array on a second member of the support device, the second member configured to retain the second substrate, the array comprising a plurality of capture probes, wherein a capture probe of the plurality of capture probes comprises (i) a spatial barcode and (ii) a capture domain; (0 applying a reagent medium to the first substrate and/or the second substrate; (g) operating an alignment mechanism of the support device to move the first member and/or the second member such that at least a portion of the biological sample is aligned with at least a portion of the array and the portion of the biological sample and the portion of the array contact the reagent medium, and such that the first substrate and the second substrate are separated by a distance of less than 50 micrometers; (h) when the biological sample is aligned with at least a portion of the array, (i) releasing the analyte capture agent from the biological sample and (ii) migrating the analyte capture agent and/or the capture agent barcode domain from the biological sample to the array; and (i) hybridizing the capture handle sequence to the capture domain. In some embodiments, the applying step (0 occurs before the mounting steps (d) and (e).

In some embodiments, the releasing step further releases the capture agent barcode domain from the analyte capture agent. In some embodiments, the second analyte is a protein analyte. In some embodiments, the protein analyte is an extracellular protein. In other embodiments, the protein analyte is an intracellular protein. In some embodiments, the analyte binding moiety is an antibody or antigen-binding fragment thereof. In some embodiments, the analyte capture agent comprises a linker. In some embodiments, the linker is a cleavable linker. In some embodiments, the cleavable linker is a photo-cleavable linker, a UV-cleavable linker, or an enzyme cleavable linker.

In some embodiments, the releasing comprises contacting the biological sample and the array with the reagent medium wherein the reagent medium comprises a nuclease. In some embodiments, the nuclease comprises an RNase. In some embodiments, the RNase is selected from RNase A, RNase C, RNase H, and RNase I. In some embodiments, the reagent medium further comprises a permeabilization agent. In some embodiments, the releasing further comprises simultaneously permeabilizing the biological sample and releasing the capture agent barcode domain from the analyte binding moiety. In some embodiments, the permeabilization agent comprises a protease. In some embodiments, the protease is selected from trypsin, pepsin, elastase, or proteinase K. In some embodiments, the reagent medium further comprises a detergent. In some embodiments, the detergent is selected from sodium dodecyl sulfate (SDS), sarkosyl, saponin, Triton X-100 ™, or Tween-20 ™. In some embodiments, the reagent medium comprises less than 5 w/v % of a detergent selected from SDS and sarkosyl. In other embodiments, the reagent medium comprises at least 5% w/v % of a detergent selected from SDS and sarkosyl. In other embodiments, the reagent medium does not comprise sodium dodcyl sulfate (SDS) or sarkosyl. In some embodiments, the biological sample and the array are contacted with the reagent medium for about 1-60 minutes. In some embodiments, the biological sample and the array are contacted with the reagent medium for about 30 minutes.

In some embodiments of the method disclosed herein, the biological sample is a tissue sample. In some embodiments, the tissue sample is a solid tissue sample. In some embodiments, the solid tissue sample is a tissue section. In some embodiments, the tissue sample is a fixed tissue sample. In some embodiments, the fixed tissue sample is a formalin fixed paraffin embedded (FFPE) tissue sample. In some embodiments, the FFPE tissue is deparaffinized and decrosslinked prior to step (a). In other embodiments, the fixed tissue sample is a formalin fixed paraffin embedded cell pellet. In other embodiments, the tissue sample is a fresh frozen tissue sample. In some embodiments, the tissue sample is fixed and stained prior to step (a). In some embodiments, the tissue sample is stained using immunofluorescence, immunohistochemistry, or hematoxylin and eosin (H&E) stain.

In some embodiments, the capture probe comprises a poly(T) sequence. In some embodiments, the capture probe comprises one or more functional domains, a unique molecular identifier (UMI), a cleavage domain, or a combination thereof. In some embodiments, the capture domain of the capture probe comprises a sequence that is substantially complementary to a sequence of the second analyte. In some embodiments, the capture domain of the capture probe comprises a sequence that is specific to the second analyte.

In some embodiments, a nucleic acid probe of the one or more nucleic acid probes comprises a padlock probe, a circular probe, or a circularized probe. In some embodiments, the detecting the one or more nucleic acid probes comprises imaging the biological sample to detect fluorescent signal. In some embodiments, a sequence of the spatial barcode or a complementary sequence thereof or an amplified sequence thereof is determined. In some embodiments, step (b) comprises in situ sequencing and/or sequential hybridization of a plurality of probes. In some embodiments, the one or more nucleic acid probes comprise a primary probe that directly hybridizes to a first analyte in the set of first analytes or the complement or the amplification product thereof. In some embodiments, the first analyte is an mRNA, the complement is a cDNA, and/or the amplification product is a rolling circle amplification (RCA) product. In some embodiments, the primary probe comprises a padlock probe, a circular probe, or a circularized probe. In some embodiments, the primary probe comprises one or more barcode sequences that uniquely identify the first analyte.

In some embodiments, of the methods disclosed herein, step (b) comprises contacting the biological sample with one or more detectably labelled probes capable of directly or indirectly hybridizing to the primary probe or a complement or amplification product thereof, optionally wherein the one or more detectably labelled probes hybridize to one or more barcode sequences of the primary probe or the complement or amplification product thereof. In some embodiments, step (b) comprises contacting the biological sample with one or more secondary probes capable of directly or indirectly hybridizing to the primary probe or the complement or amplification product thereof, optionally wherein the one or more secondary probes hybridize to one or more barcode sequences of the primary probe or the complement or amplification product thereof. In some embodiments, step (b) further comprises contacting the biological sample with one or more detectably labelled probes capable of directly or indirectly hybridizing to the one or more secondary probes or the complement or amplification product thereof, optionally wherein the one or more detectably labelled probes hybridize to one or more barcode sequences of the one or more secondary probes or the complement or amplification product thereof. In some embodiments, the method further comprises imaging the biological sample to detect the one or more barcode sequences of the primary probe or the complement or amplification product thereof, and/or the one or more barcode sequences of the one or more secondary probes or the complement or amplification product thereof, optionally wherein the sequencing comprises sequencing by ligation or sequencing by hybridization. In some embodiments, the method further comprises generating an amplification product comprising a sequence of the barcode sequence or a complementary sequence thereof. In some embodiments, the amplification product is generated by RCA. In some embodiments, the amplification product comprises one or more modified nucleotides. In some embodiments, the in situ sequencing comprises sequencing by ligation. In other embodiments, the in situ sequencing comprises sequencing by hybridization. In yet other embodiments, the in situ sequencing comprises sequencing by synthesis.

In some embodiments of the methods disclosed herein, the detecting step comprises generating a RCA product in situ in the biological sample, the RCA product comprising a sequence of the first nucleic acid probe or complement thereof; and detecting a signal (e.g., fluorescent signal) associated with the RCA product at a spatial location of the biological sample on a first substrate.

In some embodiments, disclosed herein are methods for capturing an analyte from a biological sample disposed in a first region of a first substrate, the method comprising: mounting the first substrate on a first member of a support device, the first substrate disposed in a first plane, the first member configured to retain the first substrate in a fixed position with respect to the first plane; mounting a second substrate on a second member of the support device, the second substrate disposed in a second plane and comprising a second region including a plurality of second capture probes, wherein a second capture probe of the plurality of second capture probes comprises a spatial barcode and a second capture domain; aligning, along the first plane and/or the second plane, the first region with the second region such that the first region and the second region are vertically aligned when the first substrate is positioned superior to the second substrate; applying a reagent medium to the first substrate and/or the second substrate, the reagent medium providing a permeabilization buffer between the biological sample and the second substrate; and positioning, responsive to the aligning and the applying, the second substrate such that the biological sample contacts at least a portion of the reagent medium when the first and second members are aligned and within a threshold distance along an axis orthogonal to the second plane, thereby allowing the analyte to migrate from the biological sample to the second substrate, the analyte binding to the second capture domain.

In some embodiments, at least one of the first substrate and the second substrate further comprise a spacer, wherein after the first and second substrate being mounted on the support device, the spacer is disposed between the first substrate and second substrate and is configured to maintain the reagent medium within a chamber formed by the first substrate, the second substrate, and the spacer, and maintain a separation distance between the first substrate and the second substrate, the spacer positioned to at least partially surround an area on the first substrate on which the biological sample is disposed and/or the array disposed on the second substrate, wherein the area of the first substrate, the spacer, and the second substrate at least partially encloses a volume comprising the biological sample. In some embodiments, the chamber comprises a partially or fully sealed chamber. In some embodiments, the separation distance comprises a distance of at least 2 μm. In some embodiments, wherein the separation distance comprises a distance between about 5 μm to 25 μm. In some embodiments, the second substrate comprises the spacer. In other embodiments, the first substrate comprises the spacer.

In some embodiments, the delivering the reagent medium to the first substrate and/or the second substrate comprises delivering the reagent medium to a region of the spacer, the region outside an enclosed area of the second substrate, or the enclosed area formed by the spacer. In some embodiments, assembling the chamber comprises positioning, responsive to the delivering, the first substrate at an angle such that a dropped side of the first substrate contacts at least a portion of the reagent medium when the first substrate and the second substrate are within a threshold distance along an axis orthogonal to the second substrate, the dropped side urging the reagent medium toward the three sides partially surrounding the fluid. In some embodiments, the support device is configured to maintain an approximately parallel arrangement of the first substrate and the second substrate. In some embodiments, the support device further comprises an alignment mechanism coupled to the second member, the alignment mechanism comprising a linear actuator configured to move the second member along an axis orthogonal to the plane of the second member. In some embodiments, the alignment mechanism is coupled to the second member. In some embodiments, the linear actuator is configured to move the second member along the axis orthogonal to the plane of the second member at a velocity of at least 0.1 mm/sec. In some embodiments, the linear actuator is configured to move the second member along the axis orthogonal to the plane of the second member with an amount of force of at least 0.1 lbs.

In any of the foregoing embodiments, the one or more nucleic acid probes can comprise 100, 200, 300, 400, 500 or more species of nucleic acid probes and the set of first analytes or complements or amplification products thereof can comprise 100, 200, 300, 400, 500 or more analytes or complements or amplification products thereof. In some embodiments, the first analyte and the second analyte are the same. In some embodiments, the first analyte and the second analyte are an RNA analyte.

In some embodiments, disclosed herein are methods for analyzing multiple analytes in a biological sample placed on a first substrate, the methods including (a) contacting the biological sample with an analyte capture agent that binds to a first analyte in the biological sample, wherein the analyte capture agent comprises an analyte binding moiety and a capture agent barcode domain, and wherein the capture agent barcode domain comprises a nucleic acid sequence; (b) detecting in the biological sample all or a portion of the nucleic acid sequence of the capture agent barcode domain at a spatial location of the biological sample; (c) hybridizing a first probe and a second probe to a second analyte, wherein the first probe comprises a sequence that is substantially complementary to a first sequence of the second analyte, the second probe comprises a sequence that is substantially complementary to a second sequence of the second analyte, and wherein the second probe comprises a capture probe binding domain; (d) coupling the first probe and the second probe, thereby generating a connected probe; (e) mounting the first substrate on a first member of a support device, the first member configured to retain the first substrate; (0 mounting a second substrate comprising an array on a second member of the support device, the second member configured to retain the second substrate, the array comprising a plurality of capture probes, wherein a capture probe of the plurality of capture probes comprises (i) a spatial barcode and (ii) a capture domain; (g) applying a reagent medium to the first substrate and/or the second substrate, the reagent medium comprising a permeabilization agent; (h) operating an alignment mechanism of the support device to move the first member and/or the second member such that at least a portion of the biological sample is aligned with at least a portion of the array and the portion of the biological sample and the portion of the array contact the reagent medium, and such that the first substrate and the second substrate are separated by a distance of less than 50 micrometers; (i) when the biological sample is aligned with at least a portion of the array, (i) releasing the connected probe from the second analyte and (ii) migrating the connected probe from the biological sample to the array; and (j) hybridizing the connected probe to the capture domain. In some embodiments, step (b) comprises contacting the biological sample with a detectably labeled probe capable of hybridizing to all or a portion of the nucleic acid sequence of the capture agent barcode domain, optionally wherein the detectably labeled probe comprises a fluorophore.

In some embodiments, the detecting includes imaging the biological sample to detect fluorescent signal. In some embodiments, the first analyte is a protein analyte. In some embodiments, the protein analyte is an intracellular or extracellular protein. In some embodiments, the analyte binding moiety is an antibody or antigen-binding fragment thereof. In some embodiments, the second analyte is an RNA analyte. In some embodiments, the second analyte is an mRNA analyte. In some embodiments, the methods further include determining (i) all or a part of the sequence of the connected probe, or a complement thereof, and (ii) the spatial barcode, or a complement thereof, optionally wherein the method further comprises using the determined sequence of (i) and (ii) to determine the location and abundance of the second analyte in the biological sample.

In some embodiments, provided herein are methods for analyzing an analyte in a biological sample placed on a first substrate, the methods including: (a) providing on the first substrate a biological sample that has previously been subject to an in situ analysis; (b) hybridizing a first probe and a second probe to the analyte, wherein the first probe comprises a sequence that is substantially complementary to a first sequence of the analyte, the second probe comprises a sequence that is substantially complementary to a second sequence of the analyte, and wherein the second probe comprises a capture probe binding domain; (c) coupling the first probe and the second probe, thereby generating a connected probe; (d) mounting the first substrate on a first member of a support device, the first member configured to retain the first substrate; (e) mounting a second substrate comprising an array on a second member of the support device, the second member configured to retain the second substrate, the array comprising a plurality of capture probes, wherein a capture probe of the plurality of capture probes comprises (i) a spatial barcode and (ii) a capture domain; (0 applying a reagent medium to the first substrate and/or the second substrate, the reagent medium comprising a permeabilization agent; (g) operating an alignment mechanism of the support device to move the first member and/or the second member such that at least a portion of the biological sample is aligned with at least a portion of the array and the portion of the biological sample and the portion of the array contact the reagent medium, and such that the first substrate and the second substrate are separated by a distance of less than 50 micrometers; (h) when the biological sample is aligned with at least a portion of the array, (i) releasing the connected probe from the second analyte and (ii) migrating the connected probe from the biological sample to the array; and (i) hybridizing the connected probe to the capture domain. In some embodiments, the in situ analysis includes in situ hybridization of one or more nucleic acid probes to a second analyte. In some embodiments, the in situ analysis further comprises detecting in the biological sample the one or more nucleic acid probes at a spatial location of the biological sample using fluorescence.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 13A shows spatial data for expression of a single analyte gene for a mouse brain tissue section.

FIG. 13B shows spatial data for expression of a single analyte gene for a second replicate of the same mouse brain tissue section as shown in FIG. 13A.

FIG. 14A shows spatial data of the entire mouse transcriptome for the same mouse brain cortex tissue section as the fluorescent in situ data presented in FIGS. 19A-19E.

FIG. 14B shows spatial data of the entire mouse transcriptome for the same mouse brain cortex tissue section as the fluorescent in situ data presented in FIGS. 8A-8E.

FIG. 15A shows spatial data of the intensity of expression of the analyte gene Hpca for the same mouse brain cortex tissue section as the fluorescent in situ data presented in FIGS. 9A-9E.

FIG. 15B shows spatial data of the intensity of expression of the analyte gene Hpca for the same mouse brain cortex tissue section as the fluorescent in situ data presented in FIGS. 8A-8E.

FIG. 19A shows the first substrate angled over (superior to) the second substrate.

FIG. 19B shows that as the first substrate lowers, and/or as the second substrate rises, the dropped side of the first substrate may contact the drop of the reagent medium.

FIG. 19C shows a full closure of the sandwich between the first substrate and the second substrate with the spacer contacting both the first substrate and the second substrate.

FIGS. 20A-20E show an example workflow for an angled sandwich assembly.

FIG. 23A shows example results for the Cyp26b1 gene in a fresh frozen mouse brain section by the in situ analysis workflow targeting 200 analyte genes (left) and the whole-transcriptome spatial analysis workflow performed on the same sample (right).

FIG. 23B shows example results for the Prdm8 gene in a fresh frozen mouse brain section by the in situ analysis workflow targeting 200 analyte genes (left) and the whole-transcriptome spatial analysis workflow performed on the same sample (right).

FIG. 23C shows example results for the Myl4 gene in a fresh frozen mouse brain section by the in situ analysis workflow targeting 200 analyte genes (left) and the whole-transcriptome spatial analysis workflow performed on the same sample (right).

FIG. 23D shows example results for the Shisa6 gene in a fresh frozen mouse brain section by the in situ analysis workflow targeting 200 analyte genes (left) and the whole-transcriptome spatial analysis workflow performed on the same sample (right).

DETAILED DESCRIPTION

I. Introduction

Figure 1:
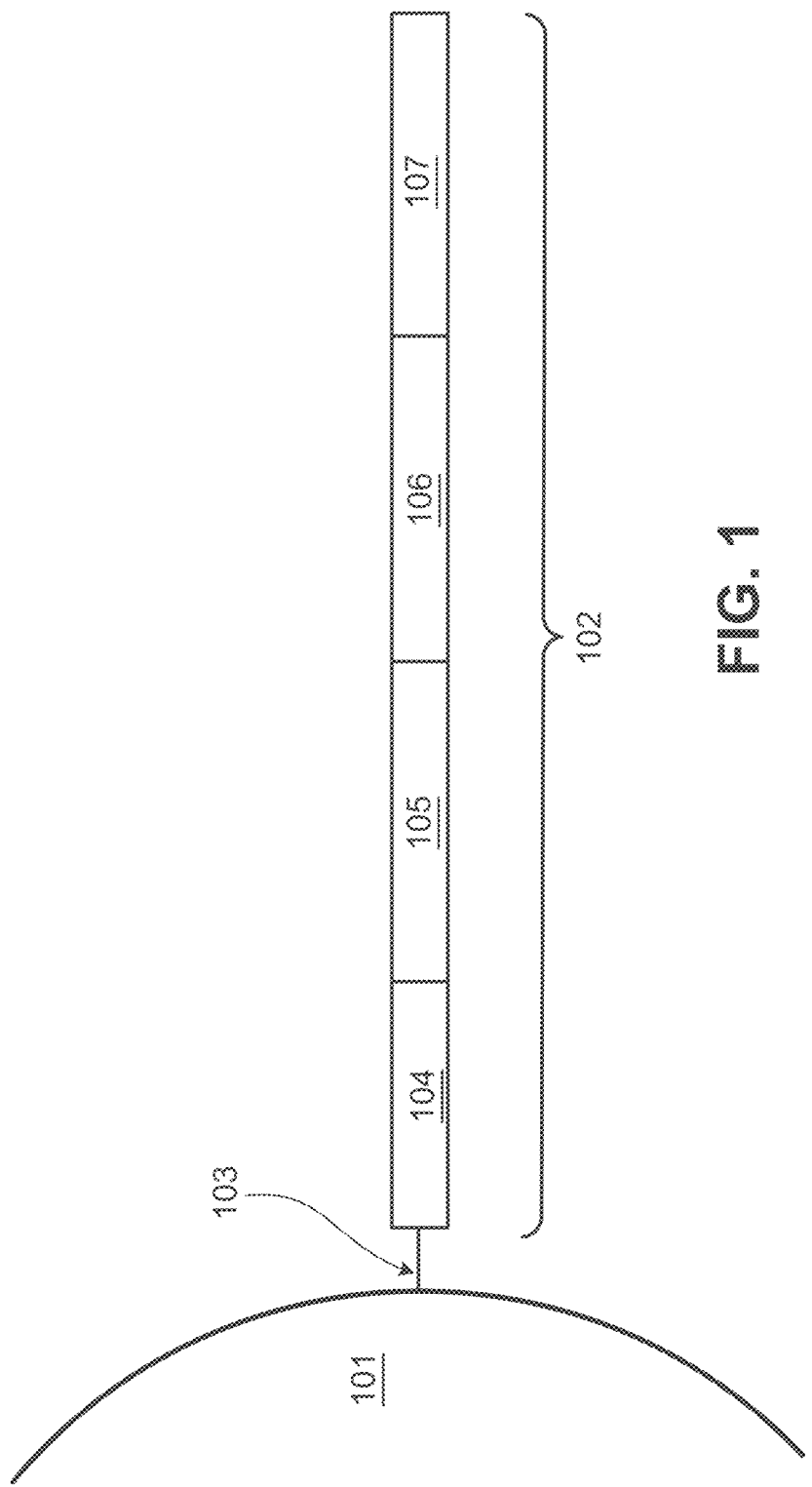
FIG. 1 is a schematic diagram showing an example of a barcoded capture probe, as described herein.

Provided herein in some aspects are methods, compositions, devices, and systems for integrated in situ spatial assays using a microscopy readout (e.g., optical sequencing of a barcode sequence of a probe directly or indirectly binds to a target analyte) and/or a sequencing readout (e.g., NGS sequencing of a analyte nucleic acid sequence per se and/or a barcode sequence of a probe), for example, for analyzing a cell in an intact tissue. The methods disclosed herein further comprise spatially profiling analytes such as the transcriptome or a subset thereof in a biological sample using an array-based spatial analysis assay.

Methods, compositions, kits, devices, and systems for in situ spatial assays, including spatial genomics and transcriptomics assays, are provided. In some embodiments, a provided method is quantitative and preserves the spatial information within a tissue sample without physically isolating cells or using homogenates. Also provided herein are compositions and methods for detecting and/or quantifying nucleic acids in cells, tissues, organs, or organisms. In some embodiments, the present disclosure provides methods for high-throughput profiling of a large number of analytes in situ, including spatial information of such analytes, such as RNA transcripts and/or DNA loci in a tissue sample. In some embodiments, the present disclosure provides methods for high-throughput profiling of a large number of analytes in situ, followed by analysis of spatial information for the same biological sample, in which sequence information for a spatial barcode associated with an analyte is obtained, and the sequence information can be used to provide information about the spatial distribution of the analyte in the biological sample.

Combined with integrated in situ spatial assays provided herein, further provided herein are spatial analysis methodologies, systems, and compositions that can provide a vast amount of analyte and/or expression data for a variety of analytes within a biological sample at high spatial resolution, while retaining native spatial context. In some embodiments, the spatial analysis of the variety of analytes within a biological sample is preceded by in situ analysis of the same biological sample, where the biological sample first undergoes an in situ analysis workflow followed by a spatial analysis workflow. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Referring to the in situ component of the disclosure, in one aspect, provided herein are methods that comprises an in situ assay module for one or more analytes in a biological sample, e.g., a tissue sample. In some embodiments, the assay comprises analyzing the presence/absence, distribution, location, amount, level, expression, or activity of analytes (e.g., nucleic acid molecules) in a tissue sample in situ. Analytes can include nucleic acid molecules and non-nucleic acid molecules, such as proteins and peptides. Nucleic acid molecules can be derived from or analyzed in any specific type of cell and/or a specific subcellular region, e.g., from cytosol, from cell nuclei, from mitochondria, from microsomes, and more generally, from any other compartment, organelle, or portion of a cell. Examples comprise DNA analytes such as genomic DNA, methylated DNA, specific methylated DNA sequences, fragmented DNA, mitochondrial DNA, and RNA/DNA hybrids. Examples of analyte nucleic acid molecules also comprise RNA analytes such as various types of coding and non-coding RNA. Examples of the different types of RNA analytes comprise messenger RNA (mRNA), ribosomal RNA (rRNA), transfer RNA (tRNA), microRNA (miRNA), pre-mRNA, and viral RNA. RNA analytes can be obtained from or analyzed in cells or cellular compartments (e.g., nucleus).

In some embodiments, the method comprises analyzing a transcriptome, proteome, or genome, e.g., the global transcriptome or genome, of a tissue sample. In some embodiments, the method comprises a process for performing spatial transcriptomics and/or spatial genomics and/or spatial proteomics, which enables the simultaneous analysis of an expression pattern and/or a location/distribution pattern of the genes, genomic loci, and proteins expressed or present in a tissue sample.

In some embodiments, the in situ assay is a targeted assay, e.g., one that analyzes pre-designed probes that directly or indirectly bind to target biological analytes, e.g., mRNA molecules in a tissue sample. In some embodiments, the in situ assay comprises providing one or more nucleic acid probes that hybridize to a target nucleic acid (or a complement, amplification product, or derivative thereof) and detecting the one or more nucleic acid probes at a spatial location of the biological sample. In some embodiments, the pre-designed probes comprise one or more primary probes or probe sets, e.g., a probe that binds to an analyte, and/or one or more secondary probes or probe sets, e.g., a probe that binds to a primary probe or complement thereof or product (e.g., a hybridization product, a ligation product, an extension product (e.g., by a DNA or RNA polymerase), a replication product, a transcription/reverse transcription product, and/or an amplification product) thereof. In some embodiments, the pre-designed probes comprise one or more higher order probes or probe sets, e.g., an $(n+1)^{th}$ order probe that binds to an $n^{th}$ order probe or complement thereof or product (e.g., a hybridization product, a ligation product, an extension product (e.g., by a DNA or RNA polymerase), a replication product, a transcription/reverse transcription product, and/or an amplification product) thereof, where n is an integer of 2 or greater. In some embodiments, the pre-designed probes are barcoded probes. In some embodiments, an $n^{th}$ order probe comprises a barcode sequence (an $n^{th}$ order barcode sequence), and an $(n+1)^{th}$ order probe binds to the $n^{th}$ order barcode sequence and comprises an $(n+1)^{th}$ order barcode sequence for binding by another barcoded probe or by a detectably labeled probe, e.g., a fluorescently labeled detection oligo, where n is an integer of 1 or greater. In any of the embodiments disclosed herein, the binding of a probe to another probe or to an analyte may be direct (e.g., via direct hybridization of nucleic acid sequences or antigen-antibody binding) or indirect (e.g., indirect hybridization via one or more bridging oligo or binding interaction). The binding interactions may be analyzed using microscopy, such as high resolution optical microscopy, to provide readouts of the presence/absence, distribution, location, amount, level, expression, or activity of the analyte. In some embodiments, the in situ assay comprises in situ sequencing and/or in situ hybridization, such as sequential hybridization of probes. In some embodiments, the in situ assay analyzes about 20, about 50, about 100, about 200, about 500, about 1,000, about 2,000, about 5,000, or about 10,000 genes, e.g., mRNA transcripts from the genes in a tissue sample. In some embodiments, mRNA transcripts from between about 100 and about 1,000 genes in a tissue sample are analyzed in situ. In another aspect, a method disclosed herein further comprises a spatial assay module, e.g., a quantitative and/or qualitative analysis of the presence/absence, distribution, location, amount, level, expression, or activity of analytes (e.g., nucleic acid molecules) in a tissue sample, facilitated by spatial barcoding, wherein the spatial pattern of the presence/absence, distribution, location, amount, level, expression, or activity of the analytes within the tissue sample is retained. In some embodiments, the method comprises analyzing a transcriptome or genome, e.g., the global transcriptome or genome, of a tissue sample. In some embodiments, the method comprises a process for performing spatial transcriptomics and/or spatial genomics, which enables the simultaneous analysis of an expression pattern and/or a location/distribution pattern of the genes or genomic loci expressed or present in a tissue sample. In some embodiments, the method couples array-based capture of nucleic acid molecules with high throughput nucleic acid sequencing technologies, which allows the nucleic acid molecules (e.g., RNA or DNA molecules) in the tissue sample, to be captured and labelled with a positional tag (e.g., a spatial barcode). In some embodiments, the method further comprises synthesis of nucleic acid molecules which are sequenced, e.g., with nucleotide resolution, and analyzed to determine which genes are expressed in any and all parts of the tissue sample. In some embodiments, the individual, separate and specific transcriptome of each cell in the tissue sample can be obtained at the same time, providing highly parallel comprehensive transcriptome signatures from individual cells within a tissue sample without losing spatial information within said investigated tissue sample. In some embodiments, the method comprises a process for performing spatial proteomics, which enables the simultaneous analysis of an expression pattern and/or a location/distribution pattern of a protein or a set of protein loci expressed or present in a tissue sample.

In another aspect, provided herein is a method that comprises an in situ assay module for one or more analytes in a biological sample, e.g., a tissue sample, followed by a spatial assay module for spatial analysis of one or more analytes in the same biological sample.

In some embodiments, a method disclosed herein comprises sequentially performing one or more in situ assays and one or more spatial assays. In some embodiments, one or more in situ assays is performed on a biological sample, e.g., a tissue sample, and subsequently one or more spatial assays is performed on the same biological sample, e.g., the same tissue sample. The in situ analysis of a first analyte (or first set of analytes) are performed before analyzing a second analyte (or second set of analytes) with a spatial assay utilizing a sequencing readout. In some embodiments, a method disclosed herein comprises providing dual readout, e.g., a microscopy readout and a sequencing readout. In some embodiments, a method disclosed herein comprises analyzing a microscopy readout for the in situ assay and a sequencing readout for the spatial assay. In some embodiments, a method disclosed herein comprises analyzing a first analyte in the in situ assay and a second analyte in the spatial assay. In some embodiments, the first analyte and the second analyte are the same molecule. In some embodiments, the first analyte and the second analyte are different molecules. In some embodiments, the first analyte and the second analyte comprise a common nucleic acid sequence, or one comprises a nucleic acid sequence and the other comprises a complementary sequence or a product (e.g., a hybridization product, a ligation product, an extension product (e.g., by a DNA or RNA polymerase), a replication product, a transcription/reverse transcription product, and/or an amplification product) thereof. In some examples, the second analyte may comprise a nucleic acid sequence of the first analyte or a nucleic acid sequence of a labelling agent for the first analyte. In some examples, the second analyte may comprise a complementary nucleic acid sequence of a nucleic acid sequence of the first analyte or a nucleic acid sequence of a labelling agent for the first analyte. In some examples, the second analyte may be a product (e.g., a hybridization product, a ligation product, an extension product (e.g., by a DNA or RNA polymerase), a replication product, a transcription/reverse transcription product, and/or an amplification product, e.g., an RCA product) of the first analyte or a probe targeting the first analyte (e.g., a probe used in the in situ assay). In some embodiments, the first analyte and the second analyte comprise different nucleic acid sequences.

In some embodiments, a method disclosed herein comprises contacting a biological sample on a substrate, e.g., a glass slide, with one or more nucleic acid probes that directly or indirectly hybridize to a first analyte nucleic acid or a complement or product (e.g., a hybridization product, a ligation product, an extension product (e.g., by a DNA or RNA polymerase), a replication product, a transcription/reverse transcription product, and/or an amplification product) thereof in the biological sample. In some embodiments, the biological sample on the substrate is subjected to an in situ analysis, e.g., in situ sequencing for the first analyte nucleic acid in the sample. In some embodiments, the biological sample is a tissue sample, such as a freshly isolated or preserved tissue section. In some embodiments, the biological sample is fixed by reversible cross-linking. In some embodiments, the biological sample is processed such that one or more analyte molecules (e.g., RNA molecules) are reversibly locked in place to preserve a spatial pattern of the presence/absence, distribution, location, amount, level, expression, or activity of the analyte within the tissue sample and/or relatively to one or more other analytes in the tissue sample. In some embodiments, the biological sample is embedded in a matrix, such as a polymeric matrix. In some embodiments, the biological sample is hydrogel-embedded. In some embodiments, the one or more analyte molecules (e.g., RNA molecules) are targeted by probes and analyzed using in situ imaging, for example sequencing by ligation, sequencing by hybridization, sequencing by synthesis, sequencing by binding, and/or sequential hybridization of barcoded probes followed by decoding. In some embodiments, molecules of a set of analytes in the sample are analyzed in situ in a highly multiplexed approach.

In some embodiments, once images of the in situ analysis are recorded, the method further comprises treating the sample so that a second nucleic acid or a complement or product (e.g., a hybridization product, a ligation product, an extension product, a replication product, a transcription/reverse transcription product, derivative, and/or an amplification product) thereof in the sample is released. For example, the method may further comprise de-crosslinking the sample so that a second analyte nucleic acid or a complement or product (e.g., a hybridization product, a ligation product, an extension product (e.g., by a DNA or RNA polymerase), a replication product, a transcription/reverse transcription product, and/or an amplification product) thereof in the sample is not locked in place (for example to a hydrogel). In some embodiments, the second nucleic acid (e.g., mRNAs) or a complement thereof or a product thereof is allowed to be directly or indirectly captured by a plurality of capture probes. In some embodiments, the substrate for in situ imaging is a first substrate, and the plurality of capture probes are provided on a second substrate, and the second analyte (e.g., a nucleic acid analyte, e.g., mRNA) or a complement thereof or a product thereof or intermediate agent thereof are allowed to migrate to the plurality of capture probes on the second substrate. In some embodiments, a capture probe of the plurality of capture probes comprises (i) a capture domain capable of capturing a nucleic acid and (ii) a spatial barcode that corresponds to the position of the capture agent on the first substrate and/or the second substrate.

In some embodiments, a method disclosed herein comprises processing a sample, e.g., by lysing or permeabilizing a de-crosslinked tissue sample, to allow one or more molecules in the sample to be directly or indirectly captured by a capture probe. In some embodiments, the one or more molecules in the sample are allowed to migrate, e.g., out of one or more cells of the sample and/or out of the sample. In some embodiments, the first analyte nucleic acid or a complement or product (e.g., a hybridization product, a ligation product, an extension product (e.g., by a DNA or RNA polymerase), a replication product, a transcription/reverse transcription product, and/or an amplification product) thereof is allowed to migrate out of a cell of the sample, to be captured by a capture agent on a substrate. In some embodiments, the second analyte nucleic acid or a complement or product (e.g., a hybridization product, a ligation product, an extension product (e.g., by a DNA or RNA polymerase), a replication product, a transcription/reverse transcription product, and/or an amplification product) thereof is allowed to migrate out of a cell of the sample, to be captured by a capture agent on a substrate. In some embodiments, after the biological sample, e.g. a tissue sample, has been processed by an in situ assay module, the first analyte nucleic acid or a complement or product (e.g., a hybridization product, a ligation product, an extension product (e.g., by a DNA or RNA polymerase), a replication product, a transcription/reverse transcription product, and/or an amplification product) thereof is allowed to migrate out of a cell of the sample.

In some embodiments, a method disclosed herein comprises generating a spatially labeled polynucleotide comprising (i) a sequence of the second analyte nucleic acid or complement thereof and (ii) a sequence of the spatial barcode or complement thereof. In some embodiments, the second analyte nucleic acid is the same as the first analyte nucleic acid analyzed during in situ imaging. In some embodiments, the second analyte nucleic acid is different from the first analyte nucleic acid analyzed during in situ imaging. In some embodiments, a plurality of second analyte nucleic acids are analyzed in the spatial assay. In some embodiments, the plurality of second analyte nucleic acids are a transcriptome or a subset thereof.

In some embodiments, the second analyte nucleic acid comprises an mRNA sequence, and the capture agent comprises a capture probe. In some embodiments, the capture probe comprises a free 3' end such that the capture probe functions as a reverse transcriptase (RT) primer using the second analyte nucleic acid as a template for primer extension. In some embodiments, the second analyte nucleic acid comprises DNA (e.g., cDNA). In some embodiments, the second analyte nucleic acid is generated prior to or during the in situ assay using an mRNA template (e.g., reverse transcription). In some embodiments, the sample is subjected to a reverse transcription reaction, wherein one or more RNA molecules in the sample are reverse transcribed to generate DNA molecules (e.g., cDNA) prior to or during an in situ assay module disclosed herein. The generated DNA molecules can be analyzed in an in situ assay module and/or a spatial assay module of an integrated method disclosed herein. In some embodiments, the free 3' end comprises an oligo dT, a random sequence, or a gene-specific sequence. In some embodiments, the capture probe further comprises a universal domain which is 5' to the spatial barcode, wherein the universal domain comprises: (i) an amplification domain; and/or (ii) a cleavage domain for releasing the generated spatially labeled polynucleotide from the surface of the substrate. In some embodiments, the generated spatially labeled polynucleotide is a cDNA or amplification product thereof.

In some embodiments, a method disclosed herein comprises releasing the spatially labeled polynucleotide or a portion thereof or a complement or product (e.g., a hybridization product, a ligation product, an extension product (e.g., by a DNA or RNA polymerase), a replication product, a transcription/reverse transcription product, and/or an amplification product) thereof for analysis. In some embodiments, the spatially labeled polynucleotide or a portion thereof or a complement or product (e.g., a hybridization product, a ligation product, an extension product (e.g., by a DNA or RNA polymerase), a replication product, a transcription/reverse transcription product, and/or an amplification product) is released from one or more cells of a biological sample, e.g., a tissue sample, after an in situ assay module for one or more analytes in the biological sample has been performed. In some embodiments, the spatially labeled polynucleotide or a portion, complement, or product thereof is released from a substrate, e.g., from the second substrate. In some embodiments, the method comprises a step of determining a sequence of at least a portion of the spatially labeled polynucleotide or a portion, complement, or product thereof. In some embodiments, the determining step comprises sequencing by ligation, sequencing by hybridization, sequencing by synthesis, and/or sequencing by binding. In some embodiments, the released spatially labeled polynucleotide or a portion, complement, or product thereof is analyzed by direct sequencing. In some embodiments, the released spatially labeled polynucleotide or a portion, complement, or product thereof is analyzed by indirect sequencing. In some embodiments, the method comprises amplifying the spatially labeled polynucleotide or a portion, complement, or product thereof, e.g., amplifying the spatially labeled polynucleotide or a portion, complement, or product thereof prior to, during, or after the releasing step. In some embodiments, the determining step comprises amplification of the released spatially labeled polynucleotide or a portion, complement, or product thereof prior to sequencing. In some embodiments, a method comprises correlating the spatial barcode of the spatially labeled polynucleotide and the detected spatial location of the one or more nucleic acid probes.

The methods disclosed herein utilize spatial analysis methodologies and compositions. Non-limiting aspects of spatial analysis methodologies and compositions are described in U.S. Pat. Nos. 10,774,374, 10,724,078, 10,480, 022, 10,059,990, 10,041,949, 10,002,316, 9,879,313, 9,783, 841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2):e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "analyte" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody) or a portion thereof, such as those described herein. For example, intermediate agents may bind to analytes at their original spatial location in the biological sample. Such intermediate agents that had been bound to the analytes may be detected according to one or more methods disclosed herein to determine presence/absence, distribution, location, amount, level, expression, or activity of the analytes, and attribute the analytes to their original spatial location in the sample.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte in a biological sample. In some embodiments, the capture probe is a nucleic acid. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

In some instance, the capture domain is designed to detect one or more specific analytes of interest. For example, a capture domain can be designed so that it comprises a sequence that is complementary or substantially complementary to one analyte of interest. Thus, the presence of a single analyte can be detected. Alternatively, the capture domain can be designed so that it comprises a sequence that is complementary or substantially complementary to a conserved region of multiple related analytes. In some instances, the multiple related analytes are analytes that function in the same or similar cellular pathways or that have conserved homology and/or function. The design of the capture probe can be determined based on the intent of the user and can be any sequence that can be used to detect an analyte of interest. In some embodiments, the capture domain sequence can therefore be random, semi-random, defined or combinations thereof, depending on the analyte(s).

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of an analyte or an intermediate agent disclosed herein. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
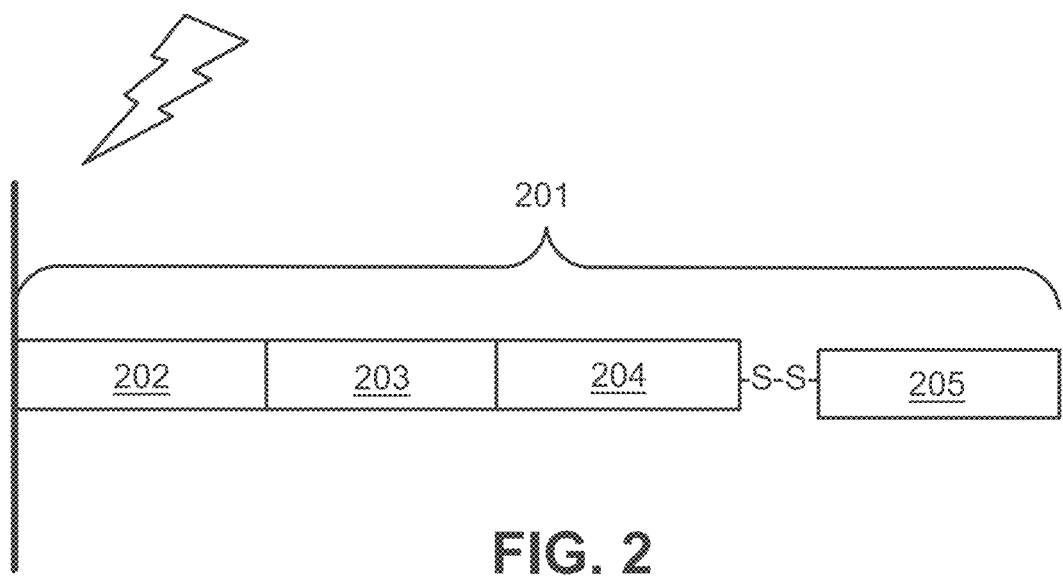
FIG. 2 is a schematic illustrating a cleavable capture probe, wherein the cleaved capture probe can enter into a non-permeabilized cell and bind to analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
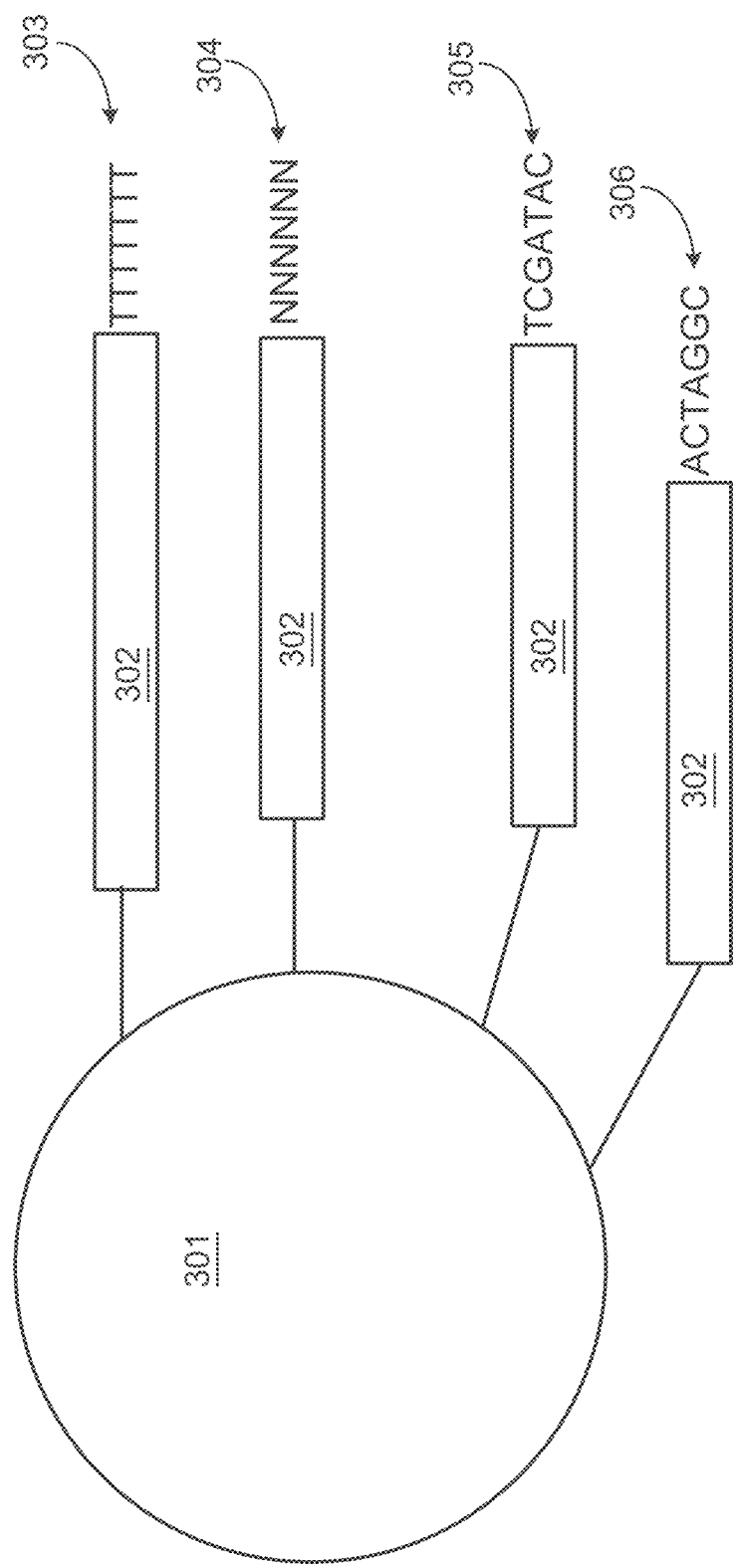
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
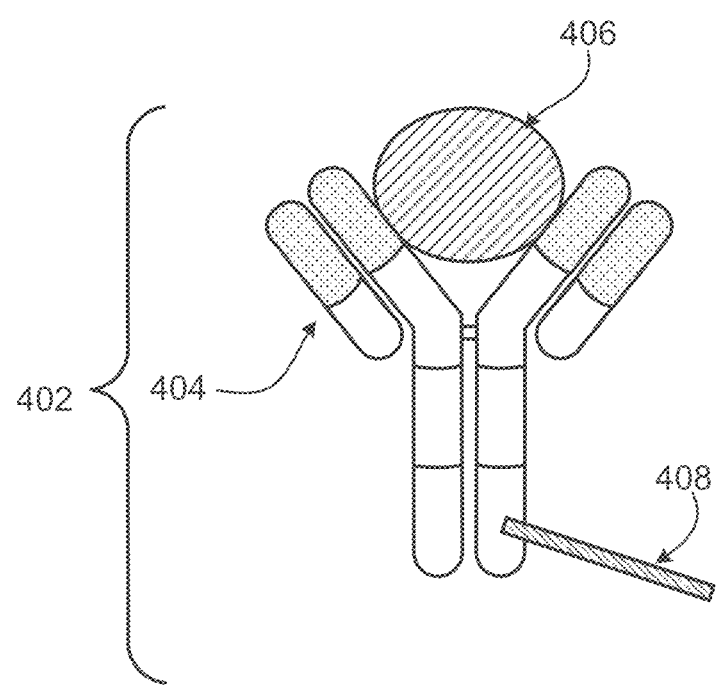
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
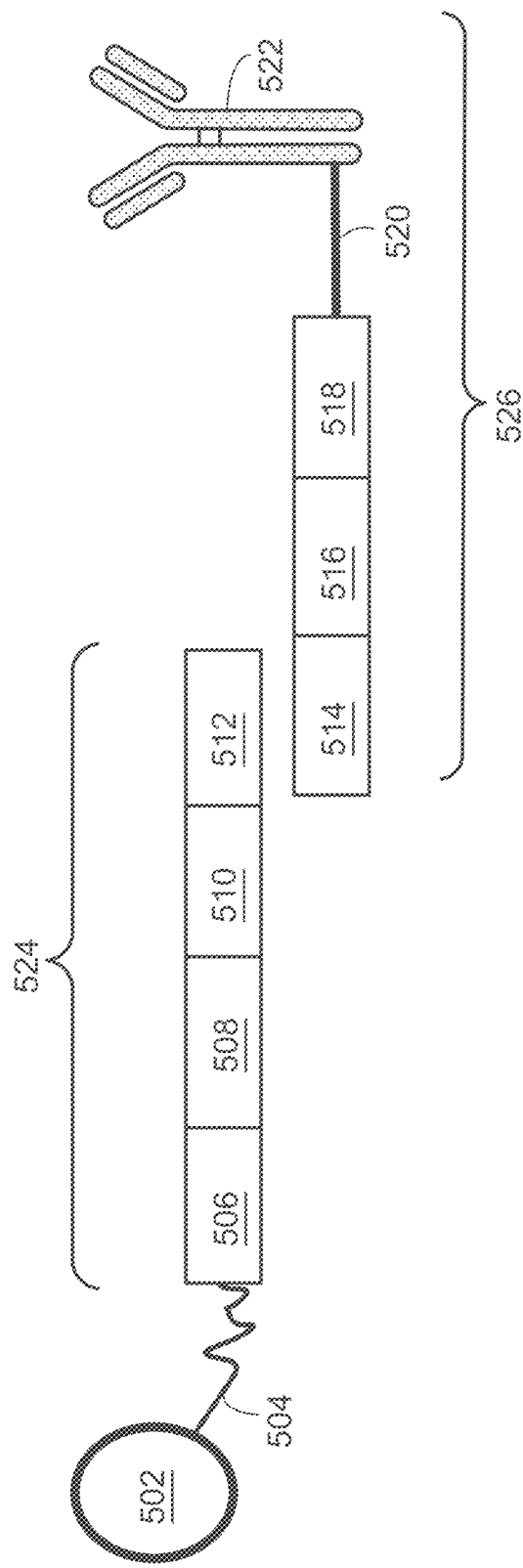
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
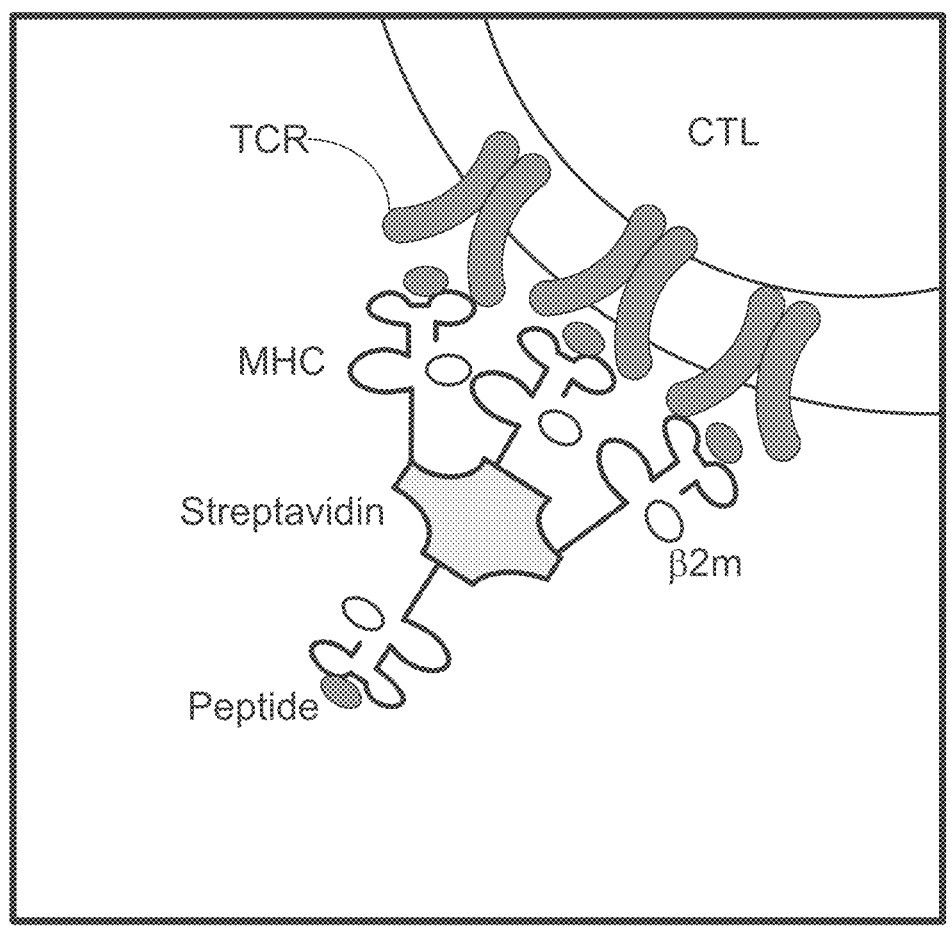
FIGS. 6A, 6B, and 6C are schematics illustrating how streptavidin cell tags can be utilized in an array-based system to produce a spatially-barcoded cells or cellular contents.
Figure 6B:
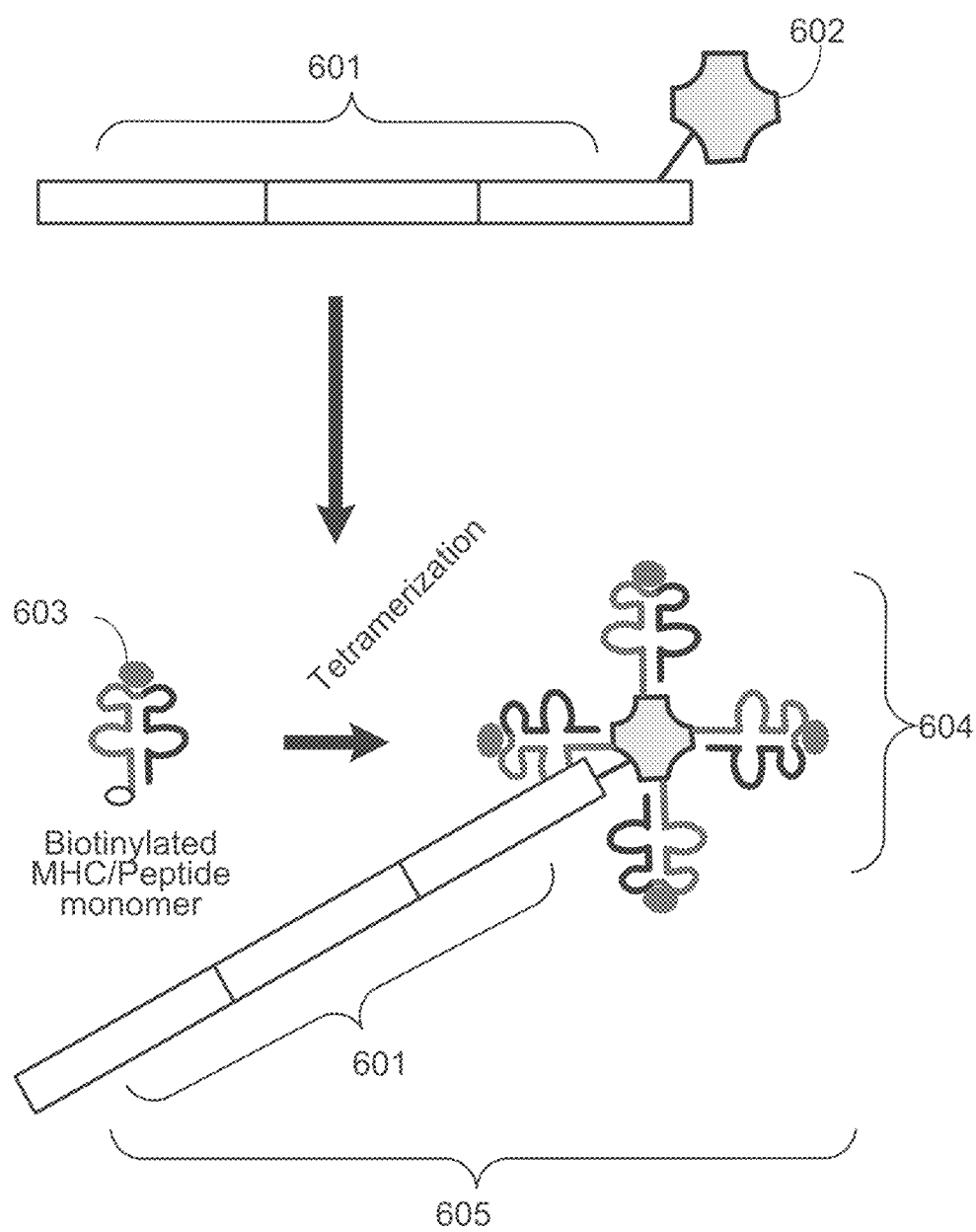
Figure 6C:
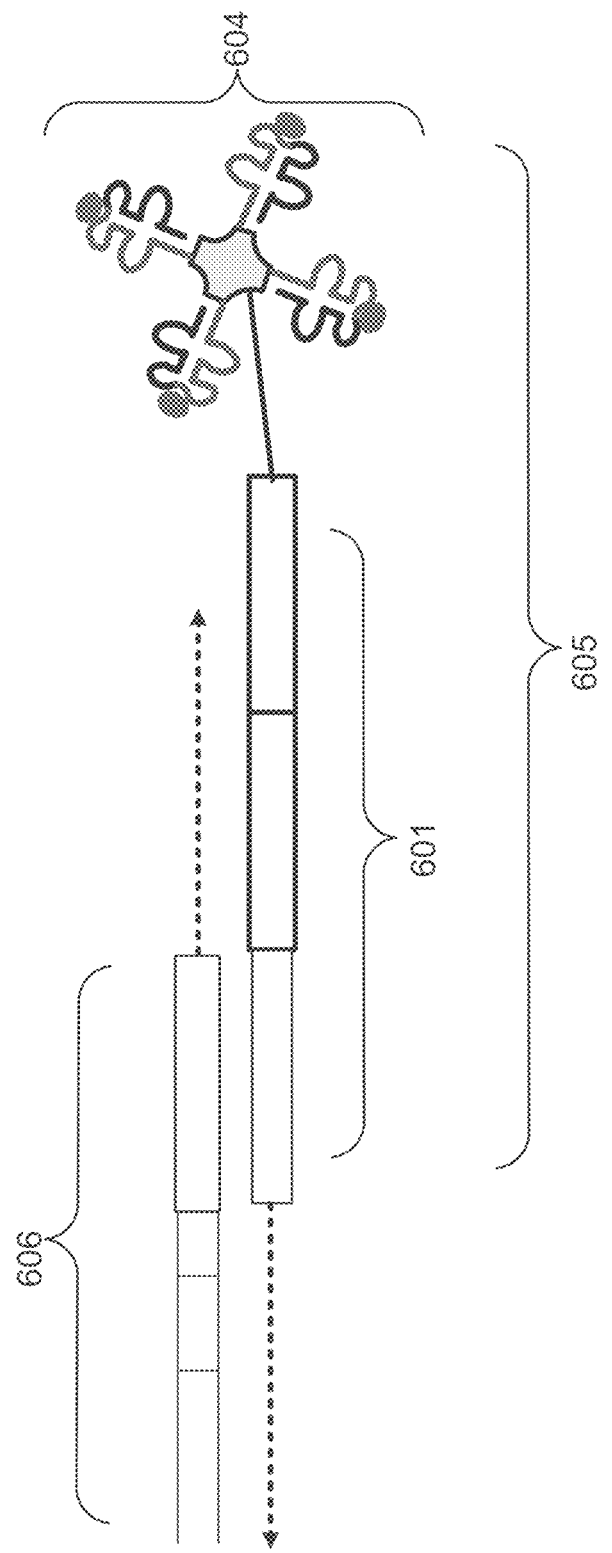

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a analyte T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 1105. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes).

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease (e.g., RNAse H). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application Publ. No. WO 2021/102003 A1 and/or U.S. Patent Application Publ. No. US 2021-0150707 A1.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. Patent Application Publ. No. US 2021-0150707 A1.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of PCT Publ. No. WO 2020/123320, PCT Publ. No. WO 2021/102005, and/or U.S. Patent Application Publ. No. US 2021-0158522 A1. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

The sandwich process is described in PCT Patent Application Publication No. WO 2020/123320, which is incorporated by reference in its entirety.

II. Methods and Systems for Capturing Analytes and Derivatives Thereof

1. Introduction

The methods provided herein disclose methods of analyzing the location and/or abundance of a nucleic acid or protein analyte in a biological sample using a combination of in situ and spatial analyses. In some instances, the methods include performing in situ analysis on a biological sample placed on a first substrate followed by transferring analytes or intermediate agents from the biological sample to a second substrate having a plurality of capture probes. In some instances, the methods include performing in situ analysis on a biological sample mounted on a first substrate, followed by aligning (e.g., sandwiching) the first substrate having the biological sample with a second substrate that includes a plurality of capture probes. The aligning of the first and second substrates and transfer of analytes (including, e.g., analyte proxies, which may also be referred to herein as "intermediate agents") can be facilitated by a sandwiching process described herein. Sandwiching processes and spatial analysis methodologies disclosed herein can facilitate determining the location and abundance of a nucleic acid or protein analyte in a biological sample can be determined, as provided herein.

In some embodiments, the methods disclosed have the advantage of being capable of correlating, comparing and/or integrating a result of the in situ assay with a result of the spatial assay. In some embodiments, methods disclosed herein comprise correlating, comparing and/or integrating the presence/absence, distribution, location, amount, level, expression, or activity of a first analyte (e.g., a first nucleic acid or protein analyte) from the in situ assay with the presence/absence, distribution, location, amount, level, expression, or activity of a second analyte (e.g., a second nucleic acid or protein analyte) from the spatial assay.

The methods provided herein can be applied to an analyte or an analyte-derived molecule(s). As used herein, an analyte derived molecule includes, without limitation, an analyte proxy or intermediate agent (e.g., a connected probe disclosed herein, an analyte capture agent disclosed herein or portion thereof), a product of reverse transcription (e.g., an extended capture probe),). In some embodiments, the analyte or analyte derived molecules comprise RNA and/or DNA. In some embodiments, the analyte or analyte derived molecules comprise one or more proteins.

In some instances, the methods disclosed herein provide efficient release of an analyte or analyte derived molecule (e.g. or i.e., an intermediate agent) from a biological sample so that it can be easily captured or detected using methods disclosed herein. In some instances, the methods disclosed herein provide efficient release of an analyte or analyte derived molecule (e.g. or i.e., an intermediate agent) from a biological sample that has previously undergone an in situ analysis workflow so that the analyte or analyte derived molecule (e.g. or i.e., an intermediate agent) can be easily captured or detected using methods disclosed herein.

In some instances, the methods disclosed herein allow for detection of analytes or analyte derived molecules (e.g. or i.e., intermediate agents) from different biological samples using a single array comprising a plurality of capture probes. As such, in some instances, the methods allow for serial capture of analytes or analyte derived molecules (e.g. or i.e., intermediate agents) from multiple samples. The analytes or analyte derived molecules can then be demultiplexed using biological-sample-specific index sequences to identify it biological sample origin.

Provided herein is a workflow that includes (i) an in situ assay module, (ii) methods of sandwiching two substrates together in order to transfer analytes/intermediate agents to array of capture probes, and (iii) methods of spatial capture and analysis.

In some instances, the in situ assay module can begin by contacting a biological sample mounted on a first substrate with nucleic acid probes that are designed to hybridize to analytes in the biological sample. After hybridization, the probes can be detected (e.g., using fluorescence) in the biological sample at a spatial location of the biological sample (e.g., by microscopy).

The methods disclosed herein include a second method of spatial detection using RNA-templated ligation ("RTL") probe pairs. Such method can comprise contacting the biological sample mounted on the first substrate with the RTL probe pairs. The first probe and a second probe of an RTL probe pair can hybridize to another analyte (e.g. or i.e., distinct from the analyte) detected by the nucleic acid probes. In some embodiments, the first probe and a second probe of an RTL probe pair hybridize to the same analyte detected by the nucleic acid probes. Each pair of RTL probes is designed such that the set of probe pairs covers an entire transcriptome. Each hybridized RTL probe pair is ligated on the first substrate, creating a ligation product. Next, the methods include aligning the first substrate with a second substrate having a plurality of capture probes, wherein a capture probe of the plurality of capture probes comprises (i) a spatial barcode and (ii) a capture domain. Then, the ligation product is transferred to the second substrate and is captured by the capture probe.

After capture of the ligation product using the capture probe, the method can further comprise extending the capture probe, using the ligation product as a template. Thus, the product of this reaction, which may be referred to herein as an extended capture probe, includes both the spatial barcode and the ligation product or a complement thereof. After, a library comprising the extended capture probe can be generated and sequenced. Embodiments of the methods, compositions, devices, and systems disclosed herein are provided below.

2. Biological Samples and Substrates

(a) Exemplary Biological Samples

The biological sample as used herein can be any suitable biological sample described herein or known in the art. In some embodiments, the biological sample is a tissue. In some embodiments, the tissue sample is a solid tissue sample. In some embodiments, the biological sample is a tissue section. In some embodiments, the tissue is flash-frozen and sectioned. Any suitable methods described herein or known in the art can be used to flash-freeze and section the tissue sample. In some embodiments, the biological sample, e.g., the tissue, is flash-frozen using liquid nitrogen before sectioning. In some embodiments, the sectioning is performed using cryosectioning. In some embodiments, the methods further comprises a thawing step, after the cryosectioning. In some embodiments, the biological sample, e.g., the tissue sample is fixed, for example in methanol, acetone, PFA or is formalin-fixed and paraffin-embedded (FFPE). In some embodiments, the biological sample comprises intact cells. In some embodiments, the biological sample is a cell pellet, e.g., a fixed cell pellet, e.g., a FFPE cell pellet.

The biological sample, e.g., tissue sample, can be stained, and imaged prior, during, and/or after each step of the methods described herein. Any of the methods described herein or known in the art can be used to stain and/or image the biological sample. In some embodiments, the imaging occurs prior to deaminating the sample. In some embodiments, the biological sample is stained using an H&E staining method. In some embodiments, the tissue sample is stained and imaged for about 10 minutes to about 2 hours (or any of the subranges of this range described herein). Additional time may be needed for staining and imaging of different types of biological samples.

The tissue sample can be obtained from any suitable location in a tissue or organ of a subject, e.g., a human subject. A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (e.g. or i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*. In some instances, the sample is a human sample.

In some instances, the sample is a human breast tissue sample. In some instances, the sample is a human brain tissue sample.

In some instances, the tissue sample is from adrenal glands, appendix, bladder, bones, bone marrow, brain, lung bronchi, diaphragm, ears, esophagus, eyes, fallopian tubes, gallbladder, genitals, heart, hypothalamus, joints, kidneys, large intestine, larynx, liver, lungs, lymph nodes, mammary glands, mesentery, mouth, nasal cavity, nose, ovaries, pancreas, pineal gland, parathyroid glands, pharynx, pituitary gland, prostate, rectum, salivary glands, skeletal muscles, skin, small intestine, spinal cord, spleen, stomach, thymus gland, thyroid, trachea, tongue, ureters, urethra, uterus, vagina, placenta, testes, nails, vas deferens, seminal vesicles, bulbourethral glands, penis, scrotum, parathyroid glands, tonsils, nerves, subcutaneous tissue, olfactory epithelium, or cerebellum.

(b) Exemplary First and Second Substrates

In some instances, a biological sample is provided (e.g. or i.e., placed) on a first substrate for one or more in situ assay modules of the integrated assay disclosed herein. In some embodiments, the biological sample on the first substrate is contacted with one or more nucleic acid probes for one or more in situ assay modules. The one or more nucleic acid probes may directly or indirectly hybridize to a first nucleic acid or a complement or an amplification product thereof in the biological sample.

A wide variety of different substrates can be used for the in situ assay module, as long as the substrate is compatible with the sample and sample processing, the in situ reagents and reactions, and in situ signal detection (e.g., optical imaging such as fluorescence microscopy). A substrate can be any suitable support material. For instance, the first substrate and/or the second substrate can be any solid or semi-solid support upon which a biological sample can be mounted. The first substrate and/or the second substrate can include, but are not limited to, glass, modified and/or functionalized glass, hydrogels, films, membranes, plastics, paper, nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene, polycarbonate, and polymer monoliths. In some embodiments, the first substrate and/or the second substrate comprises an inert material or matrix (e.g., glass slides) that has been functionalized by, for example, treating the substrate with a material comprising reactive groups which facilitate mounting of the biological sample. The first substrate and/or the second substrate comprises a substantially flat planar surface. The first substrate and/or the second substrate can be a slide, e.g., a glass slide. For example, a glass slide such as a cover slip may be used. The first substrate and/or the second substrate can be transparent. The first substrate and/or the second substrate can also correspond to a flow cell.

In some instances, the first substrate having a sample attached thereto for an in situ assay does not comprise a plurality of capture probes immobilized on the first substrate. Instead, the capture agents are provided on one or more second substrates, to which the biological sample is introduced during or after an in situ assay module. For example, a first substrate comprising a biological sample having previously undergone an in situ assay module, and a second substrate, e.g., comprising a plurality of capture probes, may be subjected to a sandwiching process described herein to facilitate molecular interaction and/or transfer of materials from the sample to the second substrate. In some embodiments, the plurality of capture agents remain immobilized on the second substrate during a spatial assay, and molecules in the biological sample is released, delivered, and/or driven toward the second substrate for the capture agents to capture the molecules.

In some embodiments, the first substrate does not comprise a plurality (e.g., array) of capture probes, each comprising a spatial barcode.

In some embodiments, the second substrate comprises a plurality of capture probes. In some instances, a capture probe of the plurality includes a poly(T) sequence. In some embodiments, the capture probe on the second substrate includes a sequence specific to the connected probe. In some embodiments, the capture probe on the second substrate includes a functional domain. In some embodiments, the capture probe on the second substrate further includes one or more functional domains, a unique molecular identifier (UMI), a cleavage domain, and combinations thereof.

In some instances, the first substrate or the second substrate is between about 0.01 mm and about 5 mm, e.g., between about 0.05 mm and about 3 mm, between about 0.1 mm and about 2.5 mm, between about 0.2 mm and about 2 mm, between about 0.5 mm and about 1.5 mm, or about 1 mm in thickness. In some embodiments, the first substrate or the second substrate is or is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm in thickness, or of a thickness in between any of the aforementioned values.

A substrate, e.g., a first substrate and/or a second substrate, can generally have any suitable form or format. For example, the first substrate and/or the second substrate can be flat, curved, e.g., convexly or concavely curved. For example, the first substrate or the second substrate can be curved towards the area where the interaction between a biological sample, e.g., tissue sample, and a first substrate takes place. In some embodiments, the first substrate and/or the second substrate is flat, e.g., planar, chip, or slide. The first substrate and/or the second substrate can contain one or more patterned surfaces within the first substrate and/or the second substrate (e.g., channels, wells, projections, ridges, divots, etc.).

In some embodiments, the first substrate and/or the second substrate includes one or more markings on its surface, e.g., to provide guidance for aligning at least a portion of the biological sample with a plurality of capture probes on the second substrate during a sandwich process disclosed herein. For example, the first substrate and/or the second substrate can include a sample area indicator identifying the sample area. In some embodiments, during a sandwiching process described herein, the sample area indicator on the first substrate is aligned with an area of the second substrate comprising a plurality of capture probes. In some embodiments, the first and/or second substrate can include a fiducial mark. In some embodiments, the first and/or second substrate does not comprise a fiducial mark. In some embodiments, the first substrate does not comprise a fiducial mark and the second substrate comprises a fiducial mark. Such markings can be made using techniques including, but not limited to, printing, sand-blasting, and depositing on the surface.

In some embodiments, imaging can be performed using one or more fiducial markers, e.g. or i.e., objects placed in the field of view of an imaging system which appear in the image produced. Fiducial markers are typically used as a point of reference or measurement scale. Fiducial markers are their uses are described in further detail in, e.g., WO 2020/176788 A1, the entire contents of which are incorporated herein by reference.

Exemplary substrates similar to the first substrate (e.g., a substrate having no capture probes) and/or the second substrate are described in Section (I) above and in WO 2020/123320, which is hereby incorporated by reference in its entirety.

3. In Situ Assay Modules

In some aspects, provided herein are methods comprising in situ assays using microscopy as a readout, e.g., nucleic acid sequencing, hybridization, or other detection or determination methods involving an optical readout. In some aspects, detection or determination of a sequence of one, two, three, four, five, or more nucleotides of a analyte nucleic acid is performed in situ in a cell in an intact tissue. In some embodiments, the assay comprises detecting the presence or absence of an amplification product (e.g., RCA product). In some embodiments, the present disclosure provides methods for high-throughput profiling of a large number of analytes in situ, such as transcripts and/or DNA loci, e.g., for detecting and/or quantifying nucleic acids and/or proteins in cells, tissues, organs or organisms. In some embodiments, the hybridization of probes with the sample and/or detection steps during the in situ assay is performed on analytes in the sample that are not captured by capture probes or capture agents.

(a) In Situ Analysis

In some aspects, provided herein is a method comprising analyzing biological analytes based on in situ hybridization of probes comprising nucleic acid sequences. In some embodiments, the method comprises sequential hybridization of detectably-labelled oligonucleotides to barcoded probes that directly or indirectly bind to biological analytes in a sample. In some embodiments, a detectably-labelled oligonucleotide directly binds to one or more barcoded probes. In some embodiments, a detectably-labelled oligonucleotide indirectly binds to one or more barcoded probes, e.g., via one or more bridging nucleic acid molecules.

In some aspects, an in situ hybridization based assay is used to localize and analyze nucleic acid sequences (e.g., a DNA or RNA molecule comprising one or more specific sequences of interest) within a native biological sample, e.g., a portion or section of tissue or a single cell. In some embodiments, the in situ assay is used to analyze the presence, absence, an amount or level of mRNA transcripts (e.g., a transcriptome or a subset thereof, or mRNA molecules of interest) in a biological sample, while preserving spatial context. In some embodiments, the present disclosure provides compositions and methods for in situ hybridization using directly or indirectly labeled molecules, e.g., complementary DNA or RNA or modified nucleic acids, as probes that bind or hybridize to analyte nucleic acids within a biological sample of interest.

Nucleic acid probes, in some examples, may be labelled with radioisotopes, epitopes, hapten, biotin, or fluorophores, to enable detection of the location of specific nucleic acid sequences on chromosomes or in tissues. In some embodiments, probes are locus specific (e.g., gene specific) and bind or couple to specific regions of a chromosome. In alternative embodiments, probes are alphoid or centromeric repeat probes that bind or couple to repetitive sequences within each chromosome. Probes may also be whole chromosome probes (e.g., multiple smaller probes) that bind or couple to sequences along an entire chromosome.

In some embodiments, provided herein is a method comprising DNA in situ hybridization to measure and localize DNA. In some embodiments, provided herein is a method comprising RNA in situ hybridization to measure and localize RNAs (e.g., mRNAs, lncRNAs, and miRNAs) within a biological sample (e.g., a fixed tissue sample). In some embodiments, RNA in situ hybridization involves single-molecule RNA fluorescence in situ hybridization (FISH). In some embodiments, fluorescently labelled nucleic acid probes are hybridized to pre-determined RNA analytes, to visualize gene expression in a biological sample. In some embodiments, a FISH method comprises using a single nucleic acid probe specific to each analyte, e.g., single-molecule FISH (smFISH). The use of smFISH may produce a fluorescence signal that allows for quantitative measurement of RNA transcripts. In some embodiments, smFISH comprises a set of nucleic acid probes, about 50 base pairs in length, wherein each probe is coupled to a set fluorophores. For example, the set of nucleic acid probes may comprise five probes, wherein each probe coupled to five fluorophores. In some embodiments, said nucleic acid probes are instead each coupled to one fluorophore. For example, a smFISH protocol may use a set of about 40 nucleic acid probes, about 20 base pairs in length, each coupled to a single fluorophore. In some embodiments, the length of the nucleic acid probes varies, comprising 10 to 100 base pairs, such as 30 to 60 base pairs. Alternatively, a plurality of nucleic acid probes targeting different regions of the same RNA transcript may be used. It will be appreciated by those skilled in the art that the type of nucleic acid probes, the number of nucleic acid probes, the number of fluorophores coupled to said probes, and the length of said probes, may be varied to fit the specifications of the individual assay.

In further embodiments smFISH is applied to a multiplexed workflow, wherein consecutive/sequential hybridizations are used (e.g., as in seqFISH or seqFISH+) to impart a temporal barcode on analyte transcripts. Sequential rounds of fluorescence in situ hybridization may be accompanied by imaging and probe stripping, detecting individual transcripts (e.g., RNA transcripts) within a biological sample (e.g., a tissue sample, a single cell, or extracted RNA). In some embodiments, each round of hybridization comprises a pre-defined set of probes (e.g., between about 10 and about 50 probes such as 24 to 32 probes) that target unique RNA transcripts. In some examples, the pre-defined set of probes is multicolored. Optionally, multiple nucleic acid probes are attached onto the sample, wherein each probe comprises an initiation sequence for amplification, allowing for decreased autofluorescence (e.g., as in single-molecule hybridization chain reaction (smHCR)). In some embodiments, a multiplexed smFISH method described herein may multiplex from 10 s to over 10,000 mRNAs, optionally accompanied by imaging, to efficiently and accurately profile the entire transcriptome. In situ hybridization methods may further comprise using two probes to bind analyte transcripts (e.g., RNA transcripts), that serve as binding targets for amplification primers. In some embodiments, this process results in signal amplification (e.g., as in RNAscope). In some embodiments, in situ hybridization methods may employ metal tags instead of fluorophores (e.g., imaging mass cytometry). Metal-conjugated antibodies may couple to the metal tags hybridized to transcripts on a biological sample. In some embodiments, mass-cytometry may be used to quantify metal abundances, allowing the concurrent evaluation of RNA and protein within a biological sample.

In some embodiments, a method described herein comprises a multiplexed FISH protocol that is error-robust (e.g., MERFISH). In some embodiments, said protocol comprises non-readout nucleic acid probes (e.g., primary probes) comprising a binding region (e.g., a region that binds to a target such as RNA transcripts) coupled to one or more flanking regions. In some embodiments, each non-readout nucleic acid probe is coupled to two flanking regions. The non-readout nucleic acid probes may hybridize to a transcript (e.g., RNA transcript) within a biological sample (e.g., tissue sample or a single cell), such that florescent readout nucleic acid probes may subsequently serially hybridize to the flanking region(s) of the non-readout nucleic acid probes. In some embodiments, each round of hybridization comprises successive imaging and probe stripping to quench signals from readout nucleic acid probes from previous rounds. RNAs may be imaged by FISH, and errors accumulated during multiple imaging rounds (e.g., imperfect hybridizations) are detected and/or corrected. In some embodiments, expansion microscopy is employed to increase the number of detected RNA analytes without signal overlap. In similar embodiments, non-readout nucleic acid probes are cross-linked to analyte transcripts prior to imaging. Cross-linking may be performed by any method known in the art. In preferred embodiments, cross-linking is performed using hydrogel tissue embedding. Following said cross-linking steps, barcoding may be performed, comprising sequential hybridizations using readout probes coupled to pre-determined colors to generate unique barcodes (e.g., generating pseudocolors from consecutive hybridizations).

In some embodiments, one or more barcodes of a probe are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed using any suitable methods or techniques, comprising those described herein, such as RNA sequential probing of analytes (RNA SPOTs), sequential fluorescent in situ hybridization (seqFISH or seqFISH+), single-molecule fluorescent in situ hybridization (smFISH), or multiplexed error-robust fluorescence in situ hybridization (MERFISH). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); US B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

Similar strategies of in situ hybridization using variations of FISH techniques may also be adopted by methods described herein. In some embodiments, a method comprises non-barcoding multiplexed FISH protocols (e.g., ouroboros sm-FISH (osmFISH)). Non-barcoding methods may be limited to detecting a specific number of analytes, defined by the number of hybridization rounds performed. In some embodiments, imaging is performed following each hybridization round, wherein the probe is stripped after imaging, allowing for subsequent hybridization and imaging rounds.

Additional embodiments of the present disclosure may include using in situ hybridization protocols that do not rely on probe capture of transcripts from pre-defined locations. In some embodiments, optics-free spatial mapping of transcripts in a biological sample may be used (e.g., a chemically encoded microscopy system). In some embodiments, transcripts are first tagged in situ with unique nucleotide tags (e.g., unique molecular identifiers). This first reaction may be followed by a second in situ amplification reaction, labelled by a new set of unique nucleotide tags (e.g., unique event identifiers). In some embodiments, RNA or DNA sequencing may be used to identify each molecular chain sequence (e.g., concatemers). In further embodiments, an algorithm may be used to evaluate the proximities of the sequences and produce images of the analyte transcripts, in combination with sequence information.

In some embodiments, provided herein is a method comprising linking sequencing information and spatial information of analytes within endogenous environments. For example, analysis of nucleic acid sequences may be performed directly on DNA or RNA within an intact biological sample, e.g., by in situ analysis. In some embodiments, the present disclosure allows for the simultaneous identification and quantification of a plurality of analytes, such as 100 s, 1000 s, or more of transcripts (e.g., mRNA transcripts), in addition to spatial resolution of said transcripts. In some aspects, the spatial resolution of transcripts may be subcellular. Optionally, the spatial resolution may be increased using signal amplification strategies described herein.

In some embodiments, fluorescent dyes are used to target nucleic acid bases, and padlock probes are used to target RNAs in situ. In some embodiments, mRNAs are reverse transcribed into cDNAs, and padlock probes are able to bind or couple to cDNAs. In some embodiments, padlock probes comprise oligonucleotides with ends that are complementary to a target sequence (e.g., analyte cDNA transcripts). Upon hybridization of padlock probes to the target sequence, enzymes may be used to ligate the ends of the padlock probes, and catalyze the formation of circularized DNA.

In some embodiments, the ends of the padlock probes are in close proximity upon hybridization to the analyte RNA or cDNA, to allow ligation and circularization of the padlock probe. The padlock probes may additionally comprise one or more barcode sequences. In alternative embodiments, there may be a gap between the ends of the padlock probes upon hybridization to the analyte RNA or cDNA, that must be filled with nucleic acids (e.g., by DNA polymerization), prior to ligation of the ends of the padlock probes and circularization. In some embodiments, the gap between to ends of the padlock probes is of variable length, e.g., up to four base pairs, and can allow reading out the actual RNA or cDNA sequence. In some embodiments, the DNA polymerase has strand displacement activity. In some embodiments, the DNA polymerase may instead not have strand displacement activity, such as the polymerase used in barcode in situ targeted sequencing (BaristaSeq) which provides read-length of up to 15 bases using a gap-filling padlock probe approach. See, e.g., Chen et al., *Nucleic Acids Res.* 2018, 46, e22, incorporated herein by reference in its entirety.

A method described herein may comprise DNA circularization and amplification (e.g., rolling circle amplification), at the location of padlock probes. In some embodiments, amplification results in multiple repeats of padlock probe sequences. Sequencing and/or decoding of the amplified padlock probes may be performed using sequencing-by-ligation. In alternative methods, sequencing-by-hybridization or sequencing-by-synthesis are used. In some embodiments, amplicons are stabilized by crossing-linking described herein, during the sequencing process. In some embodiments, the in situ analysis methods presented in this disclosure may be automated on a microfluidic platform.

Additional approaches to in situ analysis will be appreciated by those skilled in the art. For example, in some embodiments, barcoded padlocks probes may not be reverse transcribed. Instead, a second primer binds (e.g., ligates) directly to an RNA sequence adjacent to the padlock probe. In some embodiments, amplification (e.g., rolling circle amplification) is performed, wherein the amplification product becomes embedded within a hydrogel by any suitable method known in the art (e.g., hydrogel-tissue chemistry), which is then cleaned of unbound proteins and lipids. Embedded amplification products may, for example, be sequenced using variations of the sequencing-by-ligation approach, to determine the barcode sequence of each padlock probe. In some embodiments, the combinations of chemistry and sequencing described herein may be used to analyze spatial orientation of analyte transcripts in 3D.

In some embodiments, an in situ analysis methods described in the present disclosure may be untargeted. In some embodiments, untargeted in situ analysis may comprise genome/transcriptome-wide profiling of gene expression within a biological sample, e.g., as in fluorescent in situ RNA sequencing (FISSEQ). In some embodiments, RNA species are captured and converted into cross-linked cDNA amplicons (e.g., cDNA cross-linked to the cellular protein matrix of the sample). In some examples, cDNA synthesis is performed using modified amine bases to promote the cross-linking process. The synthesis of cross-linked cDNA amplicons may be followed by amplification (e.g., rolling circle amplification) as described elsewhere herein. In some embodiments, sequencing-by-ligation may be used to sequence the amplification products. In some embodiments, the sequencing step includes partition sequencing to selectively sequence of subsets of amplification products. In some embodiments, the strategies described herein allow for the detection of RNA, DNA, and/or proteins, in tandem. In some embodiments, in situ sequencing may be combined with ex situ sequencing, e.g., as in in situ transcriptome accessibility sequencing (INSTA-Seq).

In some embodiments, in situ sequencing involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g. or i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55- and Lee et al., (2014) *Science,* 343(6177), 1360-1363. In addition, examples of methods and systems for performing in situ sequencing are described in WO2014/163886, WO2018/045181, WO2018/045186, and in U.S. Pat. Nos. 10,138,509 and 10,179,932. Exemplary techniques for in situ sequencing comprise, but are not limited to, STARmap (described for example in Wang et al., (2018) Science, 361(6499) 5691), MERFISH (described for example in Moffitt, (2016) *Methods in Enzymology,* 572, 1-49), and FISSEQ (described for example in US 2019/0032121).

(b) Probes and Probe Hybridization

In some aspects, the methods disclosed herein involve the use of one or more probes or probe sets that hybridize to a target nucleic acid, such as an RNA molecule. Exemplary probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary. In some embodiments, a primary probe (e.g., a DNA probe that directly binds to an RNA analyte) is amplified through rolling circle amplification, e.g., using a circular probe or a circularized probe from padlock ligation as a template. In some embodiments, the primary probes, such as a padlock probe or a probe set that comprises a padlock probe, contain one or more barcodes. In some embodiments, one or more barcodes are indicative of a sequence in the analyte nucleic acid, such as a single nucleotide (e.g., SNPs or point mutations), a dinucleotide sequence, a short sequence of about 5 nucleotides in length, or a sequence of any suitable length.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., PCT App. PCT/EP2018/077161, published as WO2019068880 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety.

In some embodiments, a circular probe can be indirectly hybridized to the analyte nucleic acid. In some embodiments, the circular construct is formed from a probe set capable of proximity ligation, for instance a proximity ligation in situ hybridization (PLISH) probe set. See, e.g., PCT App. PCT/US2018/023846, published as WO2018175779 which is hereby incorporated by reference in its entirety.

In some embodiments, a padlock or circular probe directly hybridizes to an RNA transcript. A splint primer can be used to facilitate DNA-templated padlock ligation. The padlock or circular probe may comprise a targeting (e.g., target-hybridizing) sequence and one or more analyte barcode regions. After probe hybridization and/or any circularization steps to provide a circular probe, in some embodiments the circular probe is amplified, e.g., in a RCA reaction, to generate an amplified molecule comprising the primary/analyte barcodes or complementary sequences thereof. In some embodiments, after amplification, the method further comprises detecting the amplification product using a detectably labeled oligonucleotide (such as a fluorescently labeled detection oligo) that is capable of hybridizing to one or more of the barcode sequences or complementary sequences thereof.

In some embodiments, a splint primer can be used to facilitate DNA-templated padlock ligation. The padlock or circular probe may comprise a targeting (e.g., target-hybridizing) sequence and one or more analyte barcode regions. After probe hybridization and/or any circularization steps to provide a circular probe, in some embodiments the circular probe is amplified, e.g., in a RCA reaction, to generate an amplified molecule comprising the primary/analyte barcodes or complementary sequences thereof. In some embodiments, after amplification, the method further comprises using a detection probe (e.g., a secondary probe) comprising (1) a barcode-binding region that hybridizes to the primary/analyte barcode region of the targeting probe directly or indirectly, and (2) two or more detection barcode regions that each hybridizes to a detectably labeled oligonucleotide. In some embodiments, two or more of the secondary barcodes are different from each other. For example, all of the secondary barcodes of the secondary probes that bind to the same primary probe may be different, e.g., each secondary barcode may specifically hybridize to a detection oligo and be uniquely identified by the detection oligo sequence.

In some embodiments, one or more nucleic acid probes directly hybridize to a set of first analytes or complements or an amplification product thereof in the biological sample. In some embodiments the set of first analytes are one or more DNA analyte molecules. In some embodiments the set of first analytes are one or more RNA analyte molecules. In some embodiments one or more nucleic acid probes directly hybridize to a set of second analytes or complements or an amplification product thereof in the biological sample. In some embodiments the set of second analytes are one or more DNA analyte molecules. In some embodiments the set of second analytes are one or more RNA analyte molecules. In some embodiments the set of first analytes is the same as the set of second analytes. In some embodiments the set of first analytes is different than the set of second analytes. In some embodiments the set of first analytes partially overlaps the set of second analytes. In some embodiments, the primary probe or a probe set comprising the primary probe hybridizes to the RNA analyte first, followed by amplification of the primary probe which is circular or circularized after analyte hybridization, e.g., using RCA.

In any of the embodiments disclosed herein, disclosed herein is a multiplexed assay where multiple analyte nucleic acids (e.g., genes or RNA transcripts) are probed with multiple nucleic acid probes. In some embodiments, the multiple nucleic acid probes include a panel of 10, 20, 30, 40, 50, 60, 70, 80, 90, 100, 200, 300, 400, 500, 600, 700, 800, 900, 1000 or more probes. The multiple nucleic acid probes can each be specific to a different analyte nucleic acid. For example, the multiple nucleic acid probes can each target a different one of 10, 20, 30, 40, 50, 60, 70, 80, 90, 100, 200, 300, 400, 500, 600, 700, 800, 900, 1000 or more analyte nucleic acids. In some embodiments, each of the multiple nucleic acid probes can target one of about 200 different nucleic acids.

In any of the embodiments disclosed herein, disclosed herein is a multiplexed assay where multiple analyte nucleic acids (e.g., genes or RNA transcripts) are probed with multiple primary probes (e.g., padlock primary probes), and optionally multiple secondary probes hybridizing to the primary barcodes (or complementary sequences thereof) are all hybridized at once, followed by sequential secondary barcode detection and decoding of the signals.

In some embodiments, ribonuclease (RNAse) inhibitors are used to protect RNA analytes and/or DNA-RNA hybrid analytes from degradation by one or more of RNAse A, RNAse B, RNAse, C, RNAse H, RNAse 1, RNAse T1, S1 nuclease, or other nucleases during the in situ analysis workflow described herein.

In some embodiments, an RNA analyte is reverse transcribed to generate a DNA molecule, and a primary probe then hybridizes to the DNA molecule. In the case of a padlock probe, the padlock can be ligated using the DNA generated from the RNA as a splint. In some embodiments, a bridging probe capable of hybridizing to a barcode sequence of the primary probe or an amplification product (e.g., RCA product) thereof may be used. A bridging probe may comprise a sequence that does not hybridize to a barcode sequence (or complement thereof) of the primary probe but capable of hybridizing to one or more detectably labelled detection oligos. An exemplary method of using detection oligos in a barcoding system via sequence-by-hybridization chemistry for spatial detection of RNA transcripts can be found at Gyllborg et al., "Hybridization-based In situ Sequencing (HybISS): spatial transcriptomic detection in human and mouse brain tissue," bioRxiv 2020.02.03.931618, which is incorporated herein by reference in its entirety.

In some embodiments, various primary probes can hybridize to an RNA analyte and be ligated using RNA-templated ligation and/or DNA-templated ligation to form a circularized probe comprising one or more barcode sequences. In some embodiments, the primary probes are one or more nucleic acid probes that directly or indirectly hybridize to a set of first analytes or complements or an amplification product thereof in the biological sample. In some embodiments, a secondary probe or bridging probe may be hybridized to the circularized probe or an amplification product thereof. In some embodiments, detection oligos may be hybridized to the circularized probe or an amplification product thereof, a secondary probe or an amplification product thereof, or a bridging probe. For example, the padlock probe can be circularized using RNA-templated ligation. An RNA-templated ligase can be used to close the circle of a linear DNA probe to circularize the padlock, and the ligation efficiency can be increased through the incorporation of ribonucleotides into DNA padlock probes. See, e.g., WO 20210262018 A1, which is incorporated herein by reference in its entirety. In some embodiments, padlock probe ligation efficiency may be increased by using DNA splint oligonucleotides. In some embodiments, the two halves may serve as a DNA splint for each other for ligation. Any suitable methods of RNA-templated ligation or DNA-templated ligation may be used in the in situ assay and are encompassed in the present disclosure.

In some embodiments, the reporter oligonucleotide comprises a sequence corresponding to the labelling agent and therefore corresponds to (e.g., uniquely identifies) an analyte (e.g., a protein analyte) or cell feature that the labelling agent labels. In some embodiments, the labelling agent can comprise a reporter oligonucleotide comprising one or more barcode sequences. Thus, the reporter oligonucleotide can be a nucleic acid analyte disclosed herein, and can be analyzed using any methods disclosed herein. In some embodiments, a probe such as a padlock probe may be used to analyte a reporter oligonucleotide. In some examples, the reporter oligonucleotide of a labelling agent that specifically recognizes a protein can be analyzed using in situ hybridization (e.g., sequential hybridization) and/or in situ sequencing (e.g., using padlock probes and rolling circle amplification of ligated padlock probes). Further, the reporter oligonucleotide of the labelling agent and/or a complement thereof and/or a product (e.g., a hybridization product, a ligation product, an extension product (e.g., by a DNA or RNA polymerase), a replication product, a transcription/reverse transcription product, and/or an amplification product) thereof can be captured by a capture agent disclosed herein and analyzed using a spatial assay.

In some embodiments, an analyte (a nucleic acid analyte or non-nucleic acid analyte) can be specifically bound by one or more reporter oligonucleotide (e.g., antibodies) each of which is attached to a reporter oligonucleotide. In some embodiments, an analyte (a nucleic acid analyte or non-nucleic acid analyte) can be specifically bound by two labelling agents (e.g., antibodies) each of which is attached to a reporter oligonucleotide (e.g., DNA) that can participate in ligation, replication, and sequence decoding reactions, e.g., using a probe or probe set. In some embodiments, the probe set may comprise two or more probes, each comprising a region that is complementary to each other. For example, a proximity ligation reaction can include reporter oligonucleotides attached to pairs of antibodies that can be joined by ligation if the antibodies have been brought in proximity to each other, e.g., by binding the same analyte protein (complex), and the DNA ligation products that form are then used to template PCR amplification, as described for example in Soderberg et al., Methods. (2008), 45(3): 227-32, the entire contents of which are incorporated herein by reference. In some embodiments, a proximity ligation reaction can include reporter oligonucleotides attached to antibodies that each bind to one member of a binding pair or complex, for example, for analyzing a binding between members of the binding pair or complex. For detection of analytes using oligonucleotides in proximity, see, e.g., U.S. Patent Application Publication No. 2002/0051986, the entire contents of which are incorporated herein by reference. In some embodiments, two analytes in proximity can be specifically bound by two labelling agents (e.g., antibodies) each of which is attached to a reporter oligonucleotide (e.g., DNA) that can participate, when in proximity when bound to their respective analytes, in ligation, replication, and/or sequence decoding reactions.

In some embodiments, two analytes (or two regions of an analyte) can be specifically bound by two different labelling agents (e.g., antibodies) each of which is attached to a reporter oligonucleotide (e.g., DNA) that can be ligated if the two labelling agents are in sufficient proximity to allow the reporter oligonucleotides to be joined via ligation. In some cases, once ligation occurs, the ligated product (e.g., ligated reporter oligonucleotides) or product or derivative thereof can be captured by a capture agent and analyzed.

In some embodiments, two analytes (or two regions of an analyte) can be specifically bound by two labelling agents (e.g., antibodies) each of which is attached to a reporter oligonucleotide (e.g., DNA), and a probe that comprises a first region for hybridizing to one of the two reporter oligonucleotides and a second region for hybridizing to the other reporter oligonucleotide is added to the sample. In some embodiments, the probe is a padlock probe optionally comprising a barcode that can be associated with the labelling agents. In some aspects, the probe can be detected by hybridizing two or more probes for ligation to sequences of the probe (e.g., padlock probe). In some cases, one the two or more probes for ligation is ligated using the padlock probe as template and the ligated product can be captured by a capture agent and analyzed. In some cases, the probe (e.g., padlock probe) can be ligated and used for downstream analysis or detection. For example, the ligated probe can be used for RCA and the RCA product can be detected using any suitable methods. In some embodiments, information from the labelling agents may be useful for characterizing cells (e.g., by targeting a cell marker and/or protein with the labelling agent(s). In some cases, the information from the labelling agent(s) can be associated with information from the in situ assay provided in Section IV.

In some embodiments, upon ligation, two probes may form a circularized probe. In some embodiments, one or more suitable probes can be used and ligated, wherein the one or more probes comprise a sequence that is complementary to the one or more reporter oligonucleotides (or portion thereof). The probe may comprise one or more barcode sequences. In some embodiments, the one or more reporter oligonucleotide may serve as a primer for rolling circle amplification (RCA) of the circularized probe. In some embodiments, a nucleic acid other than the one or more reporter oligonucleotide is used as a primer for rolling circle amplification (RCA) of the circularized probe. For example, a nucleic acid capable of hybridizing to the circularized probe at a sequence other than sequence(s) hybridizing to the one or more reporter oligonucleotide can be used as the primer for RCA. In other examples, the primer in a SNAIL probe set used as the primer for RCA.

In some embodiments, one or more analytes can be specifically bound by two primary antibodies, each of which in turn recognized by a secondary antibody each attached to a reporter oligonucleotide (e.g., DNA). Each nucleic acid molecule can aid in the ligation of the probe to form a circularized probe. In some instances, the probe can comprise one or more barcode sequences. Further, the reporter oligonucleotide may serve as a primer for rolling circle amplification of the circularized probe. The nucleic acid molecules, circularized probes, and RCA products can be analyzed using any suitable method disclosed herein for in situ analysis as well as spatial analysis.

In some embodiments, one or more probes directly or indirectly targeting one or more analytes (e.g., nucleic acids, proteins or cell features) are contacted with the sample prior to or during an in situ assay module. The one or more probes may include a labelling agent (e.g., an antibody comprising a reporter oligonucleotide), a padlock probe or probe set, templated ligation probes, an analyte capture agent, or any combination thereof. In some embodiments, one or more probes directly or indirectly targeting one or more analytes (e.g., nucleic acids, proteins or cell features) are contacted with the sample after an in situ assay module but prior to during a spatial assay module, wherein the one or more probes may include a labelling agent (e.g., an antibody comprising a reporter oligonucleotide), templated ligation probes, an analyte capture agent, a capture probe, or any combination thereof.

(c) Ligation

In some embodiments, the provided methods involve ligating one or more polynucleotides that are part of a hybridization complex that comprises an analyte nucleic acid for in situ analysis. In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has a DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g. or i.e., separated by one or more intervening nucleotides or "gaps". In some embodiments, said ends are not ligated directly to each other, but instead occurs either via the intermediacy of one or more intervening (so-called "gap" or "gap-filling" (oligo)nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or analyte nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

(d) Amplification

In some embodiments, the methods of the invention comprise the step of amplifying one or more polynucleotides, for instance the padlock probe or a circular probe formed from the padlock probe. In some embodiments, the amplifying is achieved by performing rolling circle amplification (RCA). In other embodiments, a primer that hybridizes to the padlock probe is added and used as such for amplification.

In some embodiments, a removing step is performed to remove molecules that are not specifically hybridized to the analyte nucleic acid and/or the circular probe. In some embodiments, the removing step is performed to remove unligated probes. In some embodiments, the removing step is performed after ligation and prior to amplification.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (e.g. or i.e., amplicon) containing multiple copies of the cDNA. Techniques for rolling circle amplification (RCA) are known in the art such as linear RCA, a branched RCA, a dendritic RCA, or any combination thereof (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix.

Exemplary modification and polymer matrix that can be employed in accordance with the provided embodiments comprise those described in, for example, WO 2014/163886, WO 2017/079406, US 2016/0024555, US 2018/0251833 and WO2014/025392. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

(e) Detection and Analysis

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, WO 05/065814, US 2005/0100900, WO 06/064199, WO07/010,251, US 2012/0270305, US 2013/0260372, and US 2013/0079232.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597.

In some embodiments, the barcodes of the detection probes are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of analytes (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," Nature 568(7751):235-239 (2019); Chen et al., "Spatially resolved, highly multiplexed RNA profiling in single cells," Science; 348(6233):aaa6090 (2015); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., *Opt. Lett.* (2008), 33, 1026-1028, and term "perfectly et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g. or i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

(f) Labelling Agents

In some embodiments, provided herein are methods, compositions, devices, and kits for using analyte capture agents for spatial profiling of biological analytes (e.g., RNA, DNA, and cell surface or intracellular proteins and/or metabolites). In some embodiments, an analyte capture agent (also referred to at times as a "labelling agent") may include an agent that interacts with an analyte (e.g., an analyte in a sample) and with a capture agent (e.g., a capture probe attached to a substrate) to identify the analyte. In some embodiments, the sample may be contracted with one or more labelling agents prior to, during, or after the in situ assays and/or the spatial assays provided herein. In some embodiments, the method comprises one or more post-fixing (also referred to as post-fixation) steps after contacting the sample with one or more labelling agents. In some embodiments, the analyte capture agent comprises an analyte binding moiety and a capture agent barcode domain.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the analyte (e.g., cell surface feature) to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, an analyte binding moiety may include any molecule or moiety capable of binding to an analyte (e.g., a biological analyte, e.g., a macromolecular constituent). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific analyte molecule, e.g., an analyte). The analyte binding moiety can include an antibody or antibody fragment (e.g., an antigen-binding fragment) that binds to a specific analyte (e.g., a polypeptide).

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies) as well as being readily detected, (e.g., using sequencing or array technologies). In some embodiments, the analyte capture agents can include analyte binding moieties with capture agent barcode domains attached to them. For example, an analyte capture agent can include a first analyte binding moiety (e.g., an antibody that binds to an analyte, e.g., a first cell surface feature) having associated with it a capture agent barcode domain that includes a first analyte binding moiety barcode.

In some embodiments, the capture agent barcode domain of an analyte capture agent includes an analyte capture sequence. As used herein, the term "analyte capture sequence" refers to region or moiety configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent, the capture agent barcode domain can be directly coupled to the analyte binding moiety, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties can be achieved through any of a variety of direct or indirect, covalent or non-covalent associations or attachments. For example, in the case of a capture agent barcode domain coupled to an analyte binding moiety that includes an antibody or antigen-binding fragment, such capture agent barcode domains can be covalently attached to a portion of the antibody or antigen-binding fragment using chemical conjugation techniques (e.g., Lightning-Link® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker, coupled to oligonucleotides with an avidin or streptavidin linker.) Antibody and oligonucleotide biotinylation techniques can be used, and are described for example in Fang et al., Nucleic Acids Res. (2003), 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG4-NHS ester reaction, or the like, can be used to couple capture agent barcode domains to analyte binding moieties. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn analytes active ester (e.g., $NH_2$). The reactive moiety on the analyte binding moiety can be a chemical compound or group that binds to the reactive moiety on the analyte binding moiety. Exemplary strategies to conjugate the analyte binding moiety to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety is an antibody, the antibody can be modified prior to or contemporaneously with conjugation of the oligonucleotide. For example, the antibody can be glycosylated with a substrate-permissive mutant of β-1,4-galactosyltransferase, GalT (Y289L) and azide-bearing uridine diphosphate-N-acetylgalactosamine analog uridine diphosphate-GalNAz. The modified antibody can be conjugated to an oligonucleotide with a dibenzocyclooctyne-PEG4-NHS group. In some embodiments, certain steps (e.g., COOH activation (e.g., EDC) and homobifunctional cross linkers) can be avoided to prevent the analyte binding moieties from conjugating to themselves. In some embodiments of any of the spatial profiling methods described herein, the analyte capture agent (e.g., analyte binding moiety coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins. An analyte capture agent can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent to couple with intracellular cellular constituents (such as, without limitation, intracellular proteins, metabolites and nuclear membrane proteins). Following intracellular delivery, analyte capture agents can be used to analyze intracellular constituents as described herein.

In some embodiments of any of the spatial profiling methods described herein, the capture agent barcode domain coupled to an analyte capture agent can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, an analyte binding moiety of an analyte capture agent includes one or more antibodies or antigen binding fragments thereof. The antibodies or antigen binding fragments including the analyte binding moiety can specifically bind to an analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a set of analytes present in a biological sample. In some embodiments, the set of analytes includes a single species of analyte (e.g., a single species of polypeptide). In some embodiments in which the set of analytes includes a single species of analyte, the analyte binding moieties of the plurality of analyte capture agents are the same. In some embodiments in which the set of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the set of analytes includes multiple different species of analyte (e.g., multiple different species of polypeptides).

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g. or i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent bound to the cell surface protein can be bound to a capture probe (e.g., a capture probe on an array), which capture probe includes a capture domain that interacts with an analyte capture sequence present on the capture agent barcode domain of the analyte capture agent. All or part of the capture agent barcode domain (including the analyte binding moiety barcode) can be copied with a polymerase using a 3' end of the capture domain as a priming site, generating an extended capture probe that includes the all or part of the capture probe (including a spatial barcode present on the capture probe) and a copy of the analyte binding moiety barcode. In some embodiments, the spatial array with the extended capture probe(s) can be contacted with a sample, where the analyte capture agent(s) associated with the spatial array capture the analyte(s). The analyte capture agent(s) containing the extended capture probe(s), which includes the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g. single cells) and analyzed by the single cell/droplet methods described herein. The extended capture probe can be sequenced to obtain a nucleic acid sequence, in which the spatial barcode of the capture probe is associated with the analyte binding moiety barcode of the analyte capture agent. The nucleic acid sequence of the extended capture probe can thus be associated with the analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a feature (e.g., a feature at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

4. Spatial Analysis (a) Capturing Nucleic Acid Analytes using RNA-Templated Ligation In some instances, following one or more steps of an in situ assay module described herein, one or more analytes (and/or one or more analyte proxies or intermediate agents) from the biological sample are transferred to a second substrate comprising an array of capture probes, wherein a capture probe of the array comprises a capture domain and a spatial barcode.

In some embodiments, the methods compositions, devices, and systems herein utilize RNA-templated ligation to detect the analyte. As used herein, spatial "RNA-templated ligation," or "RTL" is a process wherein individual probes (e.g., a first probe, a second probe) in a probe pair hybridize to adjacent sequences of an analyte (e.g., an RNA molecule) in a biological sample (e.g., a tissue sample). The RTL probes are then coupled (e.g., ligated) together, thereby creating a connected probe (e.g., a ligation product). RTL processes and compositions are described in US Appl. Publ. No. 2021/0285046 A1 and PCT Patent Application Publication No. WO 2021/133849 A1, each of which is incorporated by reference in its entirety.

An advantage to using RTL is that it allows for enhanced detection of analytes (e.g., low expressing analytes) because both probes must hybridize to the analyte in order for the coupling (e.g., ligating) reaction to occur. As used herein, "coupling" refers to an interaction between two probes that results in a single connected probe that comprises the two probes. In some instances, coupling is achieved through ligation. In some instances, coupling is achieved through extension of one probe to the second probe followed by ligation. In some instances, coupling is achieved through hybridization (e.g., using a third probe that hybridized to each of the two probes) followed by extension of one probe or gap filling of the sequence between the two probes using the third probe as a template.

The connected probe (e.g., ligation product) that results from the coupling (e.g., ligation) of the two probes can serve as a proxy for an analyte. Further, it is appreciated that probe pairs can be designed to cover any gene of interest or globally cover the entire transcriptome. For example, a pair of probes can be designed so that each analyte, e.g., a whole exome, a transcriptome, a genome, can conceivably be detected using a probe pair.

In some instances, following one or more steps of an in situ assay module described herein, e.g., following in situ hybridization of one or more nucleic acid probes to the biological sample and detection of the one or more probes in situ, one or more analytes (and/or one or more analyte proxies, e.g. or i.e., intermediate agents) from the biological sample are transferred to a second substrate comprising an array of capture probes, wherein a capture probe of the array comprises a capture domain and a spatial barcode. In particular, after in situ hybridization of one or more nucleic acid probes to the biological sample and/or detection of the one or more probes in situ, the methods of intermediate agent capture may include (a) hybridizing a first probe and a second probe to the analyte, wherein the first probe and the second probe each comprise a sequence that is substantially complementary to adjacent sequences of the analyte, and wherein the second probe comprises a capture probe binding domain; (b) coupling the first probe and the second probe, thereby generating a connected probe (e.g., a ligation product) comprising the capture probe binding domain; (c) contacting the biological sample with a reagent medium comprising a permeabilization agent and an agent for releasing the connected probe (e.g., a ligation product), thereby (i) permeabilizing the biological sample and (ii) releasing the connected probe (e.g., a ligation product) from the analyte; and (d) hybridizing the capture probe binding domain of the connected probe (e.g., a ligation product) to a capture domain of a capture probe, wherein the capture probe comprises: (i) a spatial barcode and (ii) a capture domain. In some embodiments, steps (a), (b), or (a) and (b) of the methods of intermediate agent capture may be performed concurrently with one or more steps of the in situ assay, e.g., concurrent with in situ hybridization of one or more nucleic acid probes.

Also provided herein are methods for analyzing an analyte in a biological sample mounted on a first substrate including (a) hybridizing a first probe and a second probe to the analyte, wherein the first probe and the second probe each include a sequence that is substantially complementary to adjacent sequences of the analyte, and wherein the second probe includes a capture probe binding domain; (b) coupling (e.g., ligating) the first probe and the second probe, thereby generating a connected probe (e.g., a ligation product) including the capture probe binding domain; (c) aligning the first substrate with a second substrate including an array, such that at least a portion of the biological sample is aligned with at least a portion of the array, wherein the array includes a plurality of capture probes, wherein a capture probe of the plurality of capture probes includes: (i) a spatial barcode and (ii) a capture domain; (d) when the biological sample is aligned with at least a portion of the array, (i) releasing the connected probe (e.g., a ligation product) from the analyte and (ii) passively or actively migrating the connected probe (e.g., a ligation product) from the biological sample to the array; and (e) hybridizing the capture probe binding domain of the connected probe (e.g., a ligation product) to the capture domain.

In some embodiments, the process of transferring the connected probe (e.g., a ligation product) from the first substrate to the second substrate is referred to as a "sandwich" process, which is described in Section (II)(4)(c) below. Sandwiching processes is described in PCT Patent Application Publication No. WO 2020/123320, which is incorporated by reference in its entirety.

The RTL as disclosed herein include hybridizing of one or more probe pairs (e.g., RTL probes) to adjacent or nearby sequences of an analyte (e.g., RNA; e.g., mRNA). In some instances, the probes are DNA molecules. In some instances, the first probe comprises at least two ribonucleic acid bases at the 3' end. In some instances, the second probe comprises a phosphorylated nucleotide at the 5' end. RTL probes can be designed using methods known in the art. In some instances, probe pairs are designed to cover an entire transcriptome of a species (e.g., a mouse or a human). In some instances, RTL probes are designed to cover a subset of a transcriptome (e.g., a mouse or a human). In some instances, the methods disclosed herein utilize about 500, about 1000, about 2000, about 3000, about 4000, about 5000, about 6000, about 7000, about 8000, about 9000, about 10,000, about 15,000, about or more probe pairs.

In some instances, the first and second analyte regions of an analyte are directly adjacent to one another. In some embodiments, the complementary sequences to which the first probe and the second probe hybridize are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, or about 150 nucleotides away from each other. Gaps between the probes may first be filled prior to coupling (e.g., ligation), using, for example, dNTPs in combination with a polymerase such as polymerase mu, DNA polymerase, RNA polymerase, reverse transcriptase, VENT polymerase, Taq polymerase, and/or any combinations, derivatives, and variants (e.g., engineered mutants) thereof. In some embodiments, when the first and second probes are separated from each other by one or more nucleotides, deoxyribonucleotides are used to extend and couple (e.g., ligate) the first and second probes.

In some instances, the first probe and the second probe hybridize to an analyte on the same transcript. In some instances, the first probe and the second probe hybridize to an analyte on the same exon. In some instances, the first probe and the second probe hybridize to an analyte on different exons. In some instances, the first probe and the second probe hybridize to an analyte that is the result of a translocation event (e.g., in the setting of cancer). The methods provided herein make it possible to identify alternative splicing events, translocation events, and mutations that change the hybridization rate of one or both probes (e.g., single nucleotide polymorphisms, insertions, deletions, point mutations).

In some embodiments, the first and/or second probe as disclosed herein includes at least two ribonucleic acid bases at the 3' end; a functional sequence; a phosphorylated nucleotide at the 5' end; and/or a capture probe binding domain. In some embodiments, the functional sequence is a primer sequence. The "capture probe binding domain" is a sequence that is complementary to a particular capture domain present in a capture probe. In some embodiments, the capture probe binding domain includes a poly(A) sequence. In some embodiments, the capture probe binding domain includes a poly-uridine sequence, a poly-thymidine sequence, or a combination thereof. In some embodiments, the capture probe binding domain includes a random sequence (e.g., a random hexamer or octamer). In some embodiments, the capture probe binding domain is complementary to a capture domain in a capture probe that detects a particular analyte(s) of interest. In some embodiments, a capture probe binding domain blocking moiety that interacts with the capture probe binding domain is provided. In some embodiments, a capture probe binding domain blocking moiety includes a sequence that is complementary or substantially complementary to a capture probe binding domain. In some embodiments, a capture probe binding domain blocking moiety prevents the capture probe binding domain from binding the capture probe when present. In some embodiments, a capture probe binding domain blocking moiety is removed prior to binding the capture probe binding domain (e.g., present in a connected probe (e.g., a ligation product)) to a capture probe. In some embodiments, a capture probe binding domain blocking moiety comprises a poly-uridine sequence, a poly-thymidine sequence, or a combination thereof.

Hybridization of the probes to the target analyte can occur at a target analyte having a sequence that is 100% complementary to the probe(s). In some embodiments, hybridization can occur at a target analyte having a sequence that is at least (e.g. at least about) 80%, at least (e.g. at least about) 85%, at least (e.g. at least about) 90%, at least (e.g. at least about) 95%, at least (e.g. at least about) 96%, at least (e.g. at least about) 97%, at least (e.g. at least about) 98%, or at least (e.g. at least about) 99% complementary to the probe(s).

In some embodiments, methods disclosed herein include a wash step after hybridizing the first and the second probes. In some embodiments, a pre-hybridization buffer is used to wash the sample. In some embodiments, a phosphate buffer is used. In some embodiments, multiple wash steps are performed to remove unbound oligonucleotides. For example, it is advantageous to decrease the amount of unhybridized probes present in a biological sample as they may interfere with downstream applications and methods.

In some embodiments, after hybridization of probes (e.g., first and the second probes) to the target analyte, the probes (e.g., the first probe and the second probe) are coupled (e.g., ligated) together, creating a single connected probe (e.g., a ligation product) that is complementary to the target analyte. Ligation can be performed enzymatically or chemically, as described herein. For example, the probes may be subjected to an enzymatic ligation reaction using a ligase (e.g., T4 RNA ligase (Rnl2), a SplintR ligase, or a T4 DNA ligase). A skilled artisan will understand that various reagents, buffers, cofactors, etc. may be included in a ligation reaction depending on the ligase being used.

In some embodiments, the first probe and the second probes are on a contiguous nucleic acid sequence. In some embodiments, the first probe is on the 3' end of the contiguous nucleic acid sequence. In some embodiments, the first probe is on the 5' end of the contiguous nucleic acid sequence. In some embodiments, the second probe is on the 3' end of the contiguous nucleic acid sequence. In some embodiments, the second probe is on the 5' end of the contiguous nucleic acid sequence.

In some embodiments, the method further includes hybridizing a third probe to the first probe and the second probe such that the first probe and the second probe abut each other. In some embodiments, the third probe comprises a sequence that is at least 80%, at least 85%, at least 90%, at least 95%, at least 96%, at least 97%, at least 98%, or at least 99% complementary to a portion of the first probe that hybridizes to the third probe. In some embodiments, the third probe comprises a sequence that is 100% complementary to a portion of the first probe that hybridizes to the third probe. In some embodiments, the third probe comprises a sequence that is at least 80%, at least 85%, at least 90%, at least 95%, at least 96%, at least 97%, at least 98%, or at least 99% complementary to a portion of the second probe that hybridizes to the third probe. In some embodiments, the third probe comprises a sequence that is 100% complementary to a portion of the second probe that hybridizes to the third probe.

In some embodiments, after coupling (e.g., ligation) of the first and second probes to create a ligation product, the connected probe (e.g., a ligation product) is released from the analyte. To release the connected probe (e.g., a ligation product), a nuclease is may be used. The nuclease may be an endonuclease. In some instances, the endonuclease is an RNAse. In some instances, the RNAse is selected from RNase A, RNase C, RNase H, or RNase I. In some embodiments, the releasing of the connected probe (e.g., a ligation product) includes contacting the biological sample with a reagent medium comprising a permeabilization agent (e.g., pepsin or proteinase K) and an agent (e.g., RNAse) for releasing the connected probe (e.g., a ligation product), thereby permeabilizing the biological sample and releasing the connected probe (e.g., a ligation product) from the analyte.

In some embodiments, the reagent medium further includes a detergent. In some embodiments, the detergent is selected from sodium dodecyl sulfate (SDS), sarkosyl, saponin, Triton X-100 ™, or Tween-20 ™. In some embodiments, the reagent medium includes less than 5 w/v % of a detergent selected from sodium dodecyl sulfate (SDS) and sarkosyl. In some embodiments, the reagent medium includes as least 5% w/v % of a detergent selected from SDS and sarkosyl. In some embodiments, the reagent medium does not include SDS or sarkosyl.

In some embodiments, the biological sample and the array are contacted with the reagent medium for about 1 to about 60 minutes (e.g., about 1 to about 55 minutes, about 1 to about 50 minutes, about 1 to about 45 minutes, about 1 to about 40 minutes, about 1 to about minutes, about 1 to about 30 minutes, about 1 to about 25 minutes, about 1 to about 20 minutes, about 1 to about 15 minutes, about 1 to about 10 minutes, about 1 to about 5 minutes, about 5 to about 60 minutes, about 5 to about 55 minutes, about 5 to about 50 minutes, about 5 to about 45 minutes, about 5 to about 40 minutes, about 5 to about 35 minutes, about 5 to about 30 minutes, about 5 to about 25 minutes, about 5 to about 20 minutes, about 5 to about 15 minutes, about 5 to about 10 minutes, about 10 to about 60 minutes, about 10 to about 55 minutes, about 10 to about 50 minutes, or about 10 to about 45 minutes. In some embodiments, the biological sample and the array are contacted with the reagent medium for about 30 minutes.

In some embodiments, at least 50% of connected probes (e.g., a ligation products) released from the portion of the biological sample aligned with the portion of the array are captured by capture probes of the portion of the array. In some embodiments, at least 50%, at least 55%, at least 60%, at least 65%, at least 70%, at least 75%, at least 85%, at least 90%, at least 95%, at least 96%, at least 97%, at least 98%, at least 99%, or 100% of connected probe (e.g., a ligation products) are detected in spots directly under the biological sample.

In some embodiments, the connected probe (e.g., a ligation product) (e.g., the analyte derived molecule) includes a capture probe binding domain, which can hybridize to a capture probe (e.g., a capture probe immobilized, directly or indirectly, on a substrate). Methods provided herein include contacting a biological sample with a substrate, wherein the capture probe is affixed to the substrate (e.g., immobilized to the substrate, directly or indirectly). After hybridization of the connected probe (e.g., a ligation product) to the capture probe, downstream methods as disclosed herein (e.g., sequencing, in situ analysis such as RCA) can be performed.

In some embodiments, the method further includes concurrently (e.g. or i.e., in a same experiment as both in situ methods disclosed herein and RTL) analyzing a different analyte in the biological sample. In some embodiments, the analysis of the different analyte includes (a) further contacting the biological sample on the first substrate with a plurality of analyte capture agents, wherein an analyte capture agent of the plurality of analyte capture agents includes an analyte binding moiety and a capture agent barcode domain, wherein the analyte binding moiety specifically binds to the different analyte, and wherein the capture agent barcode domain includes an analyte binding moiety barcode and an capture handle sequence that is complementary to a capture domain of a capture probe; and (b) hybridizing the analyte capture sequence to the capture domain. An exemplary embodiment of a workflow for analysis of protein and RNA analytes is shown in FIG. 16A. As shown in FIG. 16A, a fixed tissue sample mounted on a first substrate (e.g., a slide-mounted tissue sample) is decrosslinked, followed by hybridization of probe pairs to nucleic acid target analytes. Also as shown in FIG. 16A, a first and second probe of a probe pair is connected, e.g., ligated. The sample is optionally washed (e.g., with a buffer), prior to incubation with an analyte capture agent (e.g., an antibody) that specifically binds a different analyte, e.g., a protein analyte. The analyte capture agent comprises a capture agent barcode domain. In some embodiments, the analyte capture agent is an antibody with an oligonucleotide tag, the oligonucleotide tag comprising a capture agent barcode domain. In some embodiments, the connected probes (e.g., the ligation products) and antibody oligonucleotide tags are released from the tissue under sandwich conditions as described herein. For the sandwich conditions, the tissue-mounted slide can be aligned with an array and permeabilized with a reagent medium in the sandwich configuration as described herein (see, e.g., FIG. 16B). In some embodiments, the reagent medium comprises RNase and a permeabilization agent (e.g., Proteinase K). RNAse releases the connected probe (e.g., a ligation product) and/or capture agent barcode domain from the analyte, for capture onto a second substrate comprising an array with a plurality of capture probes (see, e.g., FIG. 16B). After capture of the connected probe and capture agent barcode domain, the tissue slide can be removed (e.g., the sandwich can be "opened" or "broken").

In some embodiments, following opening of the sandwich, the capture probes can be extended, sequencing libraries can be prepared and sequenced, and the results can be analyzed computationally.

In some embodiments, the method further includes determining (i) all or part of the sequence of the capture agent barcode domain; and (ii) all or a part of the sequence of the spatial barcode, or a complement thereof. In some embodiments, the method further includes using the determined sequence of (i), and (ii) to analyze the different analyte in the biological sample. In some embodiments, the releasing step further releases the capture agent barcode domain from the different analyte. In some embodiments, the different analyte is a protein analyte. In some embodiments, the protein analyte is an extracellular protein. In some embodiments, the protein analyte is an intracellular protein.

(b) Spatial Detection of Analytes Using Analyte Capture Agents

In some embodiments, following one or more steps of an in situ assay module described herein, one or more analytes (and/or one or more analyte proxies or intermediate agents) from the biological sample are transferred to a second substrate comprising an array of capture probes, wherein a capture probe of the array comprises a capture domain and a spatial barcode. In some instances, methods, compositions, devices, and systems disclosed herein utilize analyte capture agents for spatial detection. An "analyte capture agent" refers to a molecule that interacts with an analyte (e.g., a protein) and with a capture probe. Such analyte capture agents can be used to identify the analyte. In some embodiments, the analyte capture agent can include an analyte binding moiety and a capture agent barcode domain. In some embodiments, the analyte capture agent includes a linker. In some embodiments, the linker is a cleavable linker. In some embodiments, the cleavable linker is a photo-cleavable linker, a UV-cleavable linker, or an enzyme cleavable linker.

An analyte binding moiety is a molecule capable of binding to a specific analyte. In some embodiments, the analyte binding moiety comprises an antibody or antibody fragment. In some embodiments, the analyte binding moiety comprises a polypeptide and/or an aptamer. In some embodiments, the analyte is a protein (e.g., a protein on a surface of a cell or an intracellular protein).

A capture agent barcode domain can include a capture handle sequence which can hybridize to at least a portion or an entirety of a capture domain of a capture probe. In some embodiments, the capture handle sequence is complementary to a portion or entirety of a capture domain of a capture probe. In some embodiments, the capture handle sequence includes a poly (A) tail. In some embodiments, the capture handle sequence includes a sequence capable of binding a poly (T) domain. In some embodiments, the capture agent barcode domain comprises an analyte binding moiety barcode and a capture handle sequence. The analyte binding moiety barcode refers to a barcode that is associated with or otherwise identifies the analyte binding moiety, and the capture handle sequence can hybridize to a capture probe. In some embodiments, the capture handle sequence specifically binds to the capture domain of the capture probe. Other embodiments of an analyte capture agent useful in spatial analyte detection are described herein.

Provided herein are methods for analyzing an analyte in a biological sample including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and an capture handle sequence; (b) contacting the biological sample with a reagent medium including an agent for releasing the capture agent barcode domain from the analyte binding moiety, thereby releasing the capture agent barcode domain from the analyte binding moiety; and (c) hybridizing the capture handle sequence to a capture domain of a capture probe, wherein the capture probe includes (i) a spatial barcode and (ii) a capture domain. In some embodiments, steps (a), (b), and (c) of the method occur after the biological sample has undergone an in situ analysis or detection protocol according to methods disclosed herein. In some embodiments, steps (b) and (c) of the method occur after the biological sample has undergone an in situ analysis or detection protocol according to methods disclosed herein. In some embodiments, step (a) of the method occurs at the same time that the biological sample is undergoing an in situ analysis or detection protocol according to methods disclosed herein.

Also provided herein are methods for analyzing an analyte in a biological sample mounted on a first substrate including (a) contacting the biological sample with a plurality of analyte capture agents, wherein an analyte capture agent of the plurality of analyte capture agents includes an analyte binding moiety and a capture agent barcode domain, wherein the analyte binding moiety specifically binds to the analyte, and wherein the capture agent barcode domain includes an analyte binding moiety barcode and an capture handle sequence; (b) aligning the first substrate with a second substrate comprising an array, such that at least a portion of the biological sample is aligned with at least a portion of the array, wherein the array includes a plurality of capture probes, wherein a capture probe of the plurality of capture probes includes (i) a spatial barcode and (ii) a capture domain; (c) when the biological sample is aligned with at least a portion of the array, (i) releasing the capture agent barcode domain from the analyte and (ii) passively or actively migrating the capture agent barcode domain from the biological sample to the array; and (d) coupling the capture handle sequence to the capture domain. In some embodiments, any one of more of steps (a), (b), and (c) of the method may occur after the biological sample has undergone an in situ analysis protocol according to methods disclosed herein. In some embodiments, steps (a), b), and (c) of the method occur after the biological sample has undergone an in situ analysis protocol according to methods disclosed herein. In some embodiments, steps (b) and (c) of the method occur after the biological sample has undergone an in situ analysis or detection protocol according to methods disclosed herein. In some embodiments, step (a) of the method occurs at the same time that the biological sample is undergoing an in situ analysis or detection protocol according to methods disclosed herein.

In some embodiments, the method further includes determining (i) all or a part of the capture agent barcode domain, or a complement thereof; and (ii) all or a part of the sequence of the spatial barcode, or a complement thereof. In some embodiments, the method further includes using the determined sequence of (i) and (ii) to determine the location and abundance of the analyte in the biological sample.

In some embodiments, an analyte capture agent is introduced to a biological sample, wherein the analyte binding moiety specifically binds to an analyte, and then the biological sample can be treated to release the capture agent barcode domain from the biological sample. In some embodiments, the capture agent barcode domain can then migrate and bind to a capture domain of a capture probe, and the capture agent barcode domain can be extended to generate a spatial barcode complement at the end of the capture agent barcode domain. In some embodiments, the spatially-tagged capture agent barcode domain can be denatured from the capture probe, and analyzed using methods described herein.

In some embodiments, the releasing includes contacting the biological sample and the array with a reagent medium including a nuclease. In some embodiments, the nuclease includes an RNase. In some embodiments, the RNase is selected from RNase A, RNase C, RNase H, and RNase I. In some embodiments, the reagent medium further includes a permeabilization agent. In some embodiments, the releasing further includes simultaneously permeabilizing the biological sample and releasing the capture agent barcode domain from the analyte. In some embodiments, the permeabilization agent further includes a protease. In some embodiments, the protease is selected from trypsin, pepsin, elastase, or Proteinase K.

In some embodiments, the capture agent barcode domain is released from the analyte binding moiety by using a different stimulus that can include, but is not limited to, a proteinase (e.g., Proteinase K), an RNase, and UV light.

In some embodiments, the reagent medium further includes a detergent. In some embodiments, the detergent is selected from sodium dodecyl sulfate (SDS), sarkosyl, saponin, Triton X-100 ™, or Tween-20 ™. In some embodiments, the reagent medium includes less than 5 w/v % of a detergent selected from sodium dodecyl sulfate (SDS) and sarkosyl. In some embodiments, the reagent medium includes as least 5% w/v % of a detergent selected from SDS and sarkosyl. In some embodiments, the reagent medium does not include SDS or sarkosyl.

In some embodiments, the biological sample and the array are contacted with the reagent medium for about 1 to about 60 minutes (e.g., about 1 to about 55 minutes, about 1 to about 50 minutes, about 1 to about 45 minutes, about 1 to about 40 minutes, about 1 to about minutes, about 1 to about 30 minutes, about 1 to about 25 minutes, about 1 to about 20 minutes, about 1 to about 15 minutes, about 1 to about 10 minutes, about 1 to about 5 minutes, about 5 to about 60 minutes, about 5 to about 55 minutes, about 5 to about 50 minutes, about 5 to about 45 minutes, about 5 to about 40 minutes, about 5 to about 35 minutes, about 5 to about 30 minutes, about 5 to about 25 minutes, about 5 to about 20 minutes, about 5 to about 15 minutes, about 5 to about 10 minutes, about 10 to about 60 minutes, about 10 to about 55 minutes, about 10 to about 50 minutes, about 10 to about 45 minutes, about 10 to about 40 minutes, about 10 to about 35 minutes, about 10 to about 30 minutes, about 10 to about 25 minutes, about 10 to about 20 minutes, about 10 to about 15 minutes, about 15 to about 60 minutes, about 15 to about 55 minutes, about 15 to about 50 minutes, about 15 to about 45 minutes, about 15 to about 40 minutes, about 15 to about 35 minutes, about 15 to about 30 minutes, about 15 to about 25 minutes, about 15 to about 20 minutes, about 20 to about 60 minutes, about 20 to about 55 minutes, about 20 to about 50 minutes, about 20 to about 45 minutes, about 20 to about 40 minutes, about 20 to about 35 minutes, about 20 to about 30 minutes, about 20 to about 25 minutes, about 25 to about 60 minutes, about 25 to about 55 minutes, about 25 to about 50 minutes, about 25 to about 45 minutes, about 25 to about 40 minutes, about 25 to about 35 minutes, about 25 to about 30 minutes, about 30 to about 60 minutes, about 30 to about 55 minutes, about 30 to about 50 minutes, about 30 to about 45 minutes, about 30 to about 40 minutes, about 30 to about 35 minutes, about 35 to about 60 minutes, about 35 to about 55 minutes, about 35 to about 50 minutes, about 35 to about 45 minutes, about 35 to about 40 minutes, about 40 to about 60 minutes, about 40 to about 55 minutes, about 40 to about 50 minutes, about 40 to about 45 minutes, about 45 to about 60 minutes, about 45 to about 55 minutes, about 45 to about 50 minutes, about 50 to about 60 minutes, about 50 to about 55 minutes, or about 55 to about 60 minutes). In some embodiments, the biological sample and the array are contacted with the reagent medium for about 30 minutes.

In some embodiments, disclosed herein is a method of analyzing a biological sample, comprising contacting a biological sample on a first substrate with one or more probes comprising nucleic acid molecules that directly or indirectly hybridize to a first analyte or set of analytes which include nucleic acid molecules (or a complement or an amplification product thereof) in the biological sample. The first analyte may be an RNA molecule. In some embodiments, the method further comprises detecting the one or more probes at a spatial location of the biological sample, and providing conditions to allow a plurality of capture probes to capture a second analyte, which may be a protein analyte. In some embodiments, the protein analyte is bound by an analyte capture agent comprising a nucleic acid label that corresponds to the analyte capture agent and/or the protein analyte, and a capture probe may capture the nucleic acid label. The captured nucleic acid label (corresponding to the analyte capture agent and/or the protein analyte), or a complement thereof or an amplification product thereof, may be analyzed in a spatial assay. For example, the plurality of capture probes may be provided on a second substrate, and a capture probe of the plurality of capture probes comprises a capture domain capable of capturing a nucleic acid (e.g., the nucleic acid label), and a spatial barcode corresponding to the position of the capture probe on the second substrate. In some embodiments, the method further comprises generating a spatially labeled polynucleotide comprising (i) a sequence of the nucleic acid label (corresponding to the analyte capture agent and/or the protein analyte) or complement thereof and (ii) a sequence of the spatial barcode or complement thereof. In any of the embodiments herein, the biological sample may be contacted with the analyte capture agent for the protein analyte before, during, or after detecting the one or more probes at a spatial location of the sample. In any of the embodiments herein, the biological sample may be contacted with the analyte capture agent for the protein analyte before, during, or after an in situ analysis module performed on the sample for the first analyte which is a nucleic acid. In some embodiments, the protein analyte or a subunit or polypeptide sequence thereof can be encoded by a sequence of the nucleic acid analyte.

In some embodiments, disclosed herein is a method of analyzing a biological sample, comprising contacting a biological sample on a first substrate with one or more probes comprising nucleic acid molecules that directly or indirectly hybridize to a nucleic acid label (or a complement or an amplification product thereof) of a analyte capture agent that binds a first analyte which is a non-nucleic acid analyte in the biological sample. The first analyte may be a protein. The nucleic acid label may correspond to the analyte capture agent and/or the protein analyte. In some embodiments, the method further comprises detecting the one or more probes at a spatial location of the biological sample, and providing conditions to allow a plurality of capture probes to capture a second analyte which is a nucleic acid analyte such as an mRNA. The captured nucleic acid analyte, or a complement thereof or an amplification product thereof, may be analyzed in a spatial assay. For example, the plurality of capture probes may be provided on a second substrate, and a capture probe of the plurality of capture probes comprises a capture domain capable of capturing a nucleic acid (e.g., the nucleic acid analyte such as an mRNA), and a spatial barcode corresponding to the position of the capture probe on the second substrate. In some embodiments, the method further comprises generating a spatially labeled polynucleotide comprising (i) a sequence of the nucleic acid analyte such as an mRNA or complement thereof and (ii) a sequence of the spatial barcode or complement thereof. In any of the embodiments herein, the protein analyte or a subunit or polypeptide sequence thereof can be encoded by a sequence of the nucleic acid analyte.

In some embodiments, a method disclosed herein integrates intact tissue features from a first set of analytes in a sample in situ with assay steps capable of whole transcriptome, nucleotide resolution (e.g., full RNA sequences) analysis of a second set of analytes in the same sample. In some embodiments, the first and second sets of analytes comprises nucleic acid sequences of interest. In some embodiments, the first and second sets of analytes are mRNA transcripts. In some embodiments, the first set of analytes are a subset of the second set of analytes, e.g., the first set being a panel of mRNA transcripts for targeted analysis and the second set being the whole transcriptome or a subset thereof for a non-targeted analysis. In some embodiments, the first set of analytes comprise protein analytes and the second set of analytes comprise nucleic acid molecules (e.g., mRNA transcripts) that correspond to at least some of the protein analytes.

In some embodiments, a method disclosed herein comprises in situ analysis of a first set of analytes in a spatially intact tissue context and spatial analysis of a second set of analytes, where the spatial analysis may be confirmatory or supplemental to the in situ analysis. In some embodiments, the in situ analysis comprises a 2D analysis of a biological sample, e.g., a tissue section isolated from an organism or a tissue culture on a substrate. In some embodiments, the in situ analysis comprises a 3D analysis of a biological sample, e.g., a tissue section isolated from an organism or a tissue culture such as an organoid culture in 3D form.

In some embodiments, a method disclosed herein comprises in situ analysis of a first set of nucleic acid or protein analytes, e.g., for cell phenotyping in a tissue sample by using the nucleic acid or protein analytes as biomarkers, and spatial analysis of a second set of nucleic acid analytes, e.g., for deeper sequencing of many other nucleic acid molecules (e.g., mRNAs) in a discovery mode, for example, to identify nucleic acid molecules associated with one or more particular cell phenotype.

In some embodiments, a method disclosed herein comprises using a result from the in situ analysis of a sample to validate a result from the spatial assay of the same sample. For instance, in situ analysis results of a set of nucleic acid or protein analytes may be used to validate the spatial analysis of the same or related nucleic acid analytes or the nucleic acid molecules (DNA sequences from a spatial genomics analysis or RNA transcript sequences from a spatial transcriptomics analysis) that correspond to the protein analytes analyzed in situ. In another example, results of spatial analysis of a set of nucleic acid analytes may be used to validate the in situ analysis of the same or related nucleic acid analytes, e.g., by providing information of tissue morphology and/or spatial relationship of a nucleic acid analyte with regard to the tissue morphology and/or other molecules in the tissue.

In some embodiments, a method disclosed herein comprises in situ analysis of one or more protein analytes in a sample and spatial analysis of one or more nucleic acid analytes, e.g., mRNAs, in the same sample. In some embodiments, the in situ analysis comprises contacting the sample with one or more probes, where a probe comprises an analyte-binding moiety (e.g., an antibody) that binds a protein analyte or a portion (e.g., an epitope) thereof and a nucleic acid barcode sequence that corresponds to the analyte-binding moiety and/or the protein analyte or portion thereof. In some embodiments, the in situ analysis further comprises analyzing the one or more probes, e.g., by optical imaging. For example, the one or more probes may be barcoded probes comprising one or more nucleic acid barcode sequences, which can be directly or indirectly bound by detectably-labeled detection probes. A detectable signal or a series of signals such as fluorescence comprising a spatial pattern and/or a temporal pattern may be analyzed to reveal the presence/absence, distribution, location, amount, level, expression, or activity of the one or more protein analytes in the sample. In some embodiments, the one or more protein analytes are analyzed (e.g., by imaging) in situ in a tissue sample without migrating out of a cell of the tissue sample. In some embodiments, the one or more protein analytes are analyzed (e.g., by imaging) in situ in a tissue sample without migrating out of the tissue sample, e.g., onto a substrate. In some embodiments, the probe comprises the analyte-binding moiety (e.g., antibody) and the nucleic acid barcode sequence is not cleaved during the in situ analysis. For example, for the in situ analysis, the nucleic acid barcode sequence is not released from the analyte-binding moiety (e.g., antibody) of the probe bound to the protein analyte or captured by a capture agent on a substrate; however, after the in situ analysis, the nucleic acid barcode sequence may be released and captured by a capture agent for spatial analysis together with other nucleic acid molecules (e.g., mRNA transcripts) released from the sample.

In some embodiments, a method disclosed herein comprises in situ analysis of one or more non-polyadenylated analytes (e.g., non-polyadenylated mRNA transcripts) in a sample, and spatial analysis of one or more polyadenylated analytes (e.g., mRNAs transcripts with poly-A tails) in the same sample.

In some embodiments, a method disclosed herein comprises in situ analysis of a first region of a tissue sample and spatial analysis of a second region in the same tissue sample. In some embodiments, the first and second regions do not overlap. In some embodiments, the first and second regions overlap. The regions may be identical or one region may be entirely within the other region. In an example, a portion of a cell in a sample is analyzed in situ for a first set of analytes (e.g., a panel of mRNA transcripts of interest), e.g., with a super resolution microscope, and a region (e.g., a 1 cm×1 cm tissue slice) comprising the cell is subjected to a spatial assay disclosed herein for a second set of analytes, e.g., all mRNA transcripts for non-targeted transcriptomic analysis.

In some embodiments, a method disclosed herein comprises in situ analysis of a first set of analytes (e.g., nucleic acid analytes of interest) using a plurality of probes. The plurality of probes may comprise primary probes, second probes, and/or even higher order probes, any one or more of which may comprise nucleic acid barcode sequences. The binding of a probe to an analyte or another probe may be direct (e.g., direct hybridization) or indirect (e.g., via a splint or bridging probe). In some embodiments, a method disclosed herein comprises in situ analysis of a nucleic acid analyte (e.g., DNA or mRNA), using one or more probes that directly or indirectly bind to the nucleic acid analyte or complement or product (e.g., a hybridization product, a ligation product, an extension product (e.g., by a DNA or RNA polymerase), a replication product, a transcription/reverse transcription product, and/or an amplification product) thereof. In some embodiments, the method further comprises a spatial analysis disclosed herein, where conditions are provided to allow the capture agents to directly or indirectly capture not only the nucleic acid analyte (e.g., DNA or mRNA) but also at least one of the one or more probes. In some embodiments, the method further comprises generating a first spatially labeled polynucleotide comprising (i) a sequence of the nucleic acid analyte or complement thereof and (ii) a sequence of the spatial barcode or complement thereof of a capture agent disclosed herein, where the spatial barcode corresponds to the position of the capture agent on a substrate (e.g., the first substrate or the second substrate disclosed herein). In some embodiments, the method further comprises generating a second spatially labeled polynucleotide comprising (i) a sequence of one of the one or more probes or complement thereof and (ii) a sequence of the spatial barcode or complement thereof of a capture agent disclosed herein. In some embodiments, the method comprises analyzing both the first spatially labeled polynucleotide (for analyzing the nucleic acid analyte) and the second spatially labeled polynucleotide (for analyzing a probe that directly or indirectly binds the nucleic acid analyte), and analysis of one can be used to validate or complement the other.

In some embodiments, the method comprises capturing the nucleic acid analyte (e.g., DNA or mRNA) and at least one of the one or more probes on different capture agent molecules at the same location on a substrate. In some embodiments, the method comprises capturing the nucleic acid analyte (e.g., DNA or mRNA) and at least one of the one or more probes on different capture agent molecules having the same spatial barcode sequence(s). In some embodiments, the method comprises capturing the nucleic acid analyte (e.g., DNA or mRNA) and at least one of the one or more probes on the same capture agent. In some embodiments, the method comprises generating a spatially labeled polynucleotide comprising (i) a sequence of the nucleic acid analyte or complement thereof, (ii) a sequence of the at least one of the one or more probes or complement thereof, and (iii) a sequence of the spatial barcode or complement thereof of a capture agent disclosed herein.

In some embodiments, the probe(s) captured on the substrate may serve as a spatial reference to provide information regarding one or more other analytes (e.g., endogenous nucleic acid molecules) not targeted by the one or more probes in the in situ analysis.

In some embodiments, an in situ assay module is used as a fiducial marker for the spatial assay module. For example, a probe panel comprising a probe P1 targeting a first analyte mRNA1 of Gene No. 1 may be used to analyze a brain tissue section in situ. mRNA1 is known to be expressed in the brain and this transcript is detected at position X in the tissue sample during in situ imaging. Probe P1 and transcripts including mRNA1 of Gene No. 1 are captured by capture agents on a substrate, tagged by spatial barcodes (including spatial barcode(s) corresponding to position X), and subjected to sequencing. The sequencing reads from Position X include not only those comprising sequences corresponding to P1 and those comprising sequences corresponding to mRNA1 (as a validation of the in situ readout), but also sequencing reads comprising a sequence corresponding to mRNA2. mRNA2 may be a transcript of Gene No. 2 which is different from Gene No. 1, or a variant (e.g., splice variant) of mRNA1 from Gene No. 1. mRNA2 may or may not be targeted by a probe (e.g., probe P1) in the in situ probe panel. Regardless, the sequencing reads comprising a sequence corresponding to mRNA2 and the spatial barcode(s) or complement(s) thereof corresponding to position X indicate that mRNA2 is also present and/or expressed at position X, although mRNA2 is not represented by a probe in the in situ analysis. In this example, a probe (e.g., P1) captured on the substrate serves as a spatial reference at a position (e.g., position X) on a substrate, and analysis of spatially labeled polynucleotides comprising a sequence of the spatial barcode(s) or complement(s) thereof corresponding to the position can provide information of the presence/absence, distribution, location, amount, level, expression, or activity of an analyte (e.g., mRNA2) which is not represented or targeted by a probe in the in situ analysis.

Also provided herein are methods further including analyzing a different analyte in the biological sample. In some embodiments, the analysis of the different analyte includes (a) hybridizing a first probe and a second probe to the different analyte, wherein the first probe and the second probe each comprise a sequence that is substantially complementary to adjacent sequences of the different analyte, and wherein the second probe comprises a capture probe binding domain; (b) ligating the first probe and the second probe, thereby generating a connected probe (e.g., a ligation product) comprising the capture probe binding domain; and (c) hybridizing the capture probe binding domain of the connected probe (e.g., a ligation product) to the capture domain. In some embodiments, steps (a), (b), and (c) of the method may occur after the biological sample has undergone an in situ analysis protocol according to methods disclosed herein.

In some embodiments, the method further includes determining (i) all or part of the sequence of the connected probe (e.g., a ligation product), or a complement thereof, and (ii) all or a part of the sequence of the spatial barcode, or a complement thereof. In some embodiments, the method further includes using the determined sequence of (i), and (ii) to analyze the different analyte in the biological sample. In some embodiments, the releasing step further releases the connected probe (e.g., a ligation product) from the different analyte. In some embodiments, the different analyte is RNA. In some embodiments, the different analyte is mRNA.

In some embodiments, the capture probe comprises a poly(T) sequence. In some embodiments, the capture probe comprises a sequence complementary to the capture handle sequence. In some embodiments, the capture probe comprises a functional domain. In some embodiments, the capture probe further comprises one or more functional domains, a unique molecular identifier (UMI), a cleavage domain, and combinations thereof.

In some embodiments, the biological sample is a tissue sample. In some embodiments, the tissue sample is a tissue section. In some embodiments, the tissue sample is a fixed tissue sample. In some embodiments, the fixed tissue sample is a formalin fixed paraffin embedded (FFPE) tissue sample. In some embodiments, the FFPE tissue is deparaffinized and decrosslinked prior to step (a) of any one of the methods provided herein. In some embodiments, the fixed tissue sample is a formalin fixed paraffin embedded cell pellet. In some embodiments, the tissue sample is a fresh tissue sample or a frozen tissue sample. In some embodiments, the tissue sample is fixed and stained prior to step (a) of any one of the methods provided herein.

In some instances, RTL is performed between two oligonucleotides that each are affixed to an analyte binding moiety (e.g. or i.e., a protein-binding moiety). Generally, the methods of RTL in this setting is as follows. In some embodiments, provided herein is a method of determining a location of at least one analyte in a biological sample including: (a) hybridizing a first analyte-binding moiety to a first analyte in the biological sample, wherein the first analyte-binding moiety is bound to a first oligonucleotide, wherein the first oligonucleotide comprises: (i) a functional sequence; (ii) a first barcode; and (iii) a first bridge sequence; (b) hybridizing a second analyte-binding moiety to a second analyte in the biological sample, wherein the second analyte-binding moiety is bound to a second oligonucleotide; wherein the second oligonucleotide comprises: (i) capture probe binding domain sequence, (ii) a second barcode; and (ii) a second bridge sequence; (c) contacting the biological sample with a third oligonucleotide; (d) hybridizing the third oligonucleotide to the first bridge sequence of the first oligonucleotide and second bridge sequence of the second oligonucleotide; (e) ligating the first oligonucleotide and the second oligonucleotide, creating a connected probe (e.g., a ligation product); (0 contacting the biological sample with a substrate, wherein a capture probe is affixed to the substrate, wherein the capture probe comprises a spatial barcode and the capture domain; and (g) allowing the capture probe binding domain sequence of the second oligonucleotide to specifically bind to the capture domain. In some instances, the connected probe (e.g., a ligation product) is cleaved from the analyte biding moieties.

In some instances, two analytes (e.g., two different proteins) in close proximity in a biological sample are detected by a first analyte-binding moiety and a second analyte-binding moiety, respectively. In some embodiments, a first analyte-binding moiety and/or the second analyte-binding moiety is an analyte capture agent (e.g., any of the exemplary analyte capture agents described herein). In some embodiments, the first analyte-binding moiety and/or the second analyte-binding moiety is a first protein. In some embodiments, the first analyte-binding moiety and/or the second analyte-binding moiety is an antibody. For example, the antibody can include, without limitation, a monoclonal antibody, recombinant antibody, synthetic antibody, a single domain antibody, a single-chain variable fragment (scFv), and or an antigen-binding fragment (Fab). In some embodiments, the first analyte-binding moiety binds to a cell surface analyte (e.g., any of the exemplary cell surface analytes described herein). In some embodiments, binding of the analyte is performed metabolically. In some embodiments, binding of the analyte is performed enzymatically. In some embodiments, the methods include a secondary antibody that binds to a primary antibody, enhancing its detection.

In some embodiments, the first analyte-binding moiety and the second analyte-binding moiety each bind to the same analyte. In some embodiments, the first analyte-binding moiety and/or second analyte-binding moiety each bind to a different analyte. For example, in some embodiments, the first analyte-binding moiety binds to a first polypeptide and the second analyte-binding moiety binds to a second polypeptide.

In some embodiments of any of the methods of determining a location of at least one analyte in a biological sample, a first and/or a second oligonucleotide are bound (e.g., conjugated or otherwise attached using any of the methods described herein) to a first analyte-binding moiety and/or a second analyte-binding moiety, respectively.

In some embodiments of any of the methods of determining a location of at least one analyte in a biological sample as described herein, a second oligonucleotide is bound (e.g., conjugated or otherwise attached using any of the methods described herein) to a second analyte-binding moiety. For example, the second oligonucleotide can be covalently linked to the second analyte-binding moiety. In some embodiments, the second oligonucleotide is bound to the second analyte-binding moiety via its 5' end. In some embodiments, the second oligonucleotide includes a free 3' end. In some embodiments the second oligonucleotide is bound to the second analyte-binding moiety via its 3' end. In some embodiments, the second oligonucleotide includes a free 5' end.

In some embodiments, the oligonucleotides are bound to the first and/or second analyte-binding moieties via a linker (e.g., any of the exemplary linkers described herein). In some embodiments, the linker is a cleavable linker. In some embodiment, the linker is a linker with photo-sensitive chemical bonds (e.g., photo-cleavable linkers). In some embodiments, the linker is a cleavable linker that can undergo induced dissociation.

In some embodiments, the oligonucleotides are bound (e.g., attached via any of the methods described herein) to an analyte-binding domain via a 5' end.

In some embodiments, a barcode is used to identify the analyte-binding moiety to which it is bound. The barcode can be any of the exemplary barcodes described herein. In some embodiments, the first and/or second oligonucleotide include a capture probe binding domain sequence. For example, a capture probe binding domain sequence can be a poly(A) sequence when the capture domain sequence is a poly(T) sequence.

In some embodiments, a third oligonucleotide (e.g., a splint oligonucleotide) hybridizes to both the first and second oligonucleotides and enables ligation of the first oligonucleotide and the second oligonucleotide. In some embodiments, a ligase is used. In some aspects, the ligase includes a DNA ligase. In some aspects, the ligase includes a RNA ligase. In some aspects, the ligase includes T4 DNA ligase. In some embodiments, the ligase is a SplintR ligase.

(c) Sandwich Processes

In some embodiments, the alignment of the first substrate and the second substrate and transfer of analytes from the biological sample to the array of capture probes on the second substrate is facilitated by a sandwiching process. Accordingly, described herein are methods, compositions, devices, and systems for sandwiching together the first substrate as described herein with a second substrate having an array with capture probes.

In some embodiments, the sandwiching process may be facilitated by a device, sample holder, sample handling apparatus, or system described in, e.g., US. Patent Application Pub. No. 20210189475, PCT/US2021/036788, or PCT/US2021/050931.

Figure 16:
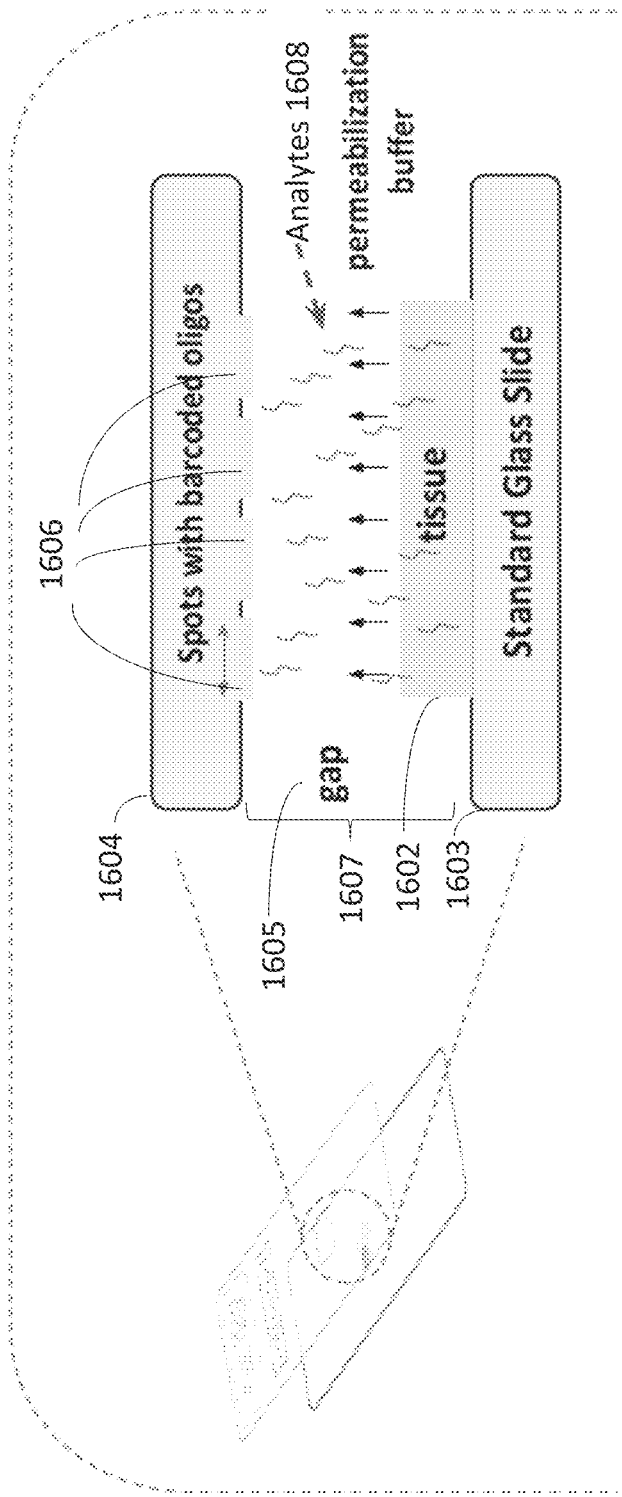
FIG. 16 shows an exemplary schematic diagram depicting a sandwiching process.

FIG. 16 is a schematic diagram depicting an exemplary sandwiching process between a first substrate comprising a biological sample (e.g., a tissue section 1602 on a slide 1603) and a second substrate comprising a spatially barcoded array, e.g., a slide 1604 that is populated with spatially-barcoded capture probes 1606. During the exemplary sandwiching process, the first substrate is aligned with the second substrate, such that at least a portion of the biological sample is aligned with at least a portion of the array (e.g., aligned in a sandwich configuration). As shown, the second substrate (e.g., slide 1604) is in a superior position to the first substrate (e.g., slide 1603). In some embodiments, the first substrate (e.g., slide 1603) may be positioned superior to the second substrate (e.g., slide 1604). In some embodiments, the first and second substrates are aligned to maintain a gap or separation distance 1607 between the two substrates. When the first and second substrates are aligned, one or more analytes are released from the biological sample and actively or passively migrate to the array for capture. In some embodiments, the migration occurs while the aligned portions of the biological sample and the array are contacted with a reagent medium 1605. The released one or more analytes may actively or passively migrate across the gap 1607 via the reagent medium 1605 toward the capture probes 1606, and be captured by the capture probes 1606.

In some embodiments, the separation distance 1607 between first and second substrates is maintained between 2 microns and 1 mm (e.g., between 2 microns and 800 microns, between 2 microns and 700 microns, between 2 microns and 600 microns, between 2 microns and 500 microns, between 2 microns and 400 microns, between 2 microns and 300 microns, between 2 microns and 200 microns, between 2 microns and 100 microns, between 2 microns and 25 microns, between 2 microns and 10 microns), measured in a direction orthogonal to the surface of first substrate that supports sample. In some embodiments, the separation distance 1607 between first and second substrates is less than 50 microns. In some instances, the distance is 2 microns. In some instances, the distance is 2.5 microns. In some instances, the distance is about 2, 3, 4, 5, 6, 7, 8, 9, 10, 11, 12, 13, 14, 15, 16, 17, 18, 19, 20, 21, 22, 23, 24, or 25 microns. In some embodiments, second substrate is placed in direct contact with the sample on the first substrate ensuring no diffusive spatial resolution losses. In some embodiments, the separation distance is measured in a direction orthogonal to a surface of the first substrate that supports the biological sample.

In some embodiments, the first and second substrates are placed in a substrate holder (e.g., an array alignment device) configured to align the biological sample and the array. In some embodiments, the device comprises a sample holder. In some embodiments, the sample holder includes a first member and a second member that receive a first substrate and a second substrate, respectively. The device can include an alignment mechanism that is connected to at least one of the members and aligns the first and second members. Thus, the devices of the disclosure can advantageously align the first substrate and the second substrate and any samples, barcoded probes, or permeabilization reagents that may be on the surface of the first and second substrates.

In some embodiments, the sandwiching process comprises: mounting the first substrate on a first member of a support device, the first member configured to retain the first substrate; mounting the second substrate on a second member of the support device, the second member configured to retain the second substrate, applying a reagent medium to the first substrate and/or the second substrate, the reagent medium comprising a permeabilization agent, operating an alignment mechanism of the support device to move the first member and/or the second member such that a portion of the biological sample is aligned (e.g., vertically aligned) with a portion of the array of capture probes and within a threshold distance of the array of capture probes, and such that the portion of the biological sample and the capture probe contact the reagent medium, wherein the permeabilization agent releases the analyte from the biological sample.

In some embodiments of a sample holder, the sample holder can include a first member including a first retaining mechanism configured to retain a first substrate comprising a sample. The first retaining mechanism can be configured to retain the first substrate disposed in a first plane. The sample holder can further include a second member including a second retaining mechanism configured to retain a second substrate disposed in a second plane. The sample holder can further includes an alignment mechanism connected to one or both of the first member and the second member. The alignment mechanism can be configured to align the first and second members along the first plane and/or the second plane such that the sample contacts at least a portion of the reagent medium when the first and second members are aligned and within a threshold distance along an axis orthogonal to the second plane. The alignment mechanism may be configured to move the second member along the axis orthogonal to the second plane and/or move the first member along an axis orthogonal to the first plane.

In some embodiments, the alignment mechanism includes a linear actuator. In some embodiments, the alignment mechanism includes one or more of a moving plate, a bushing, a shoulder screw, a motor bracket, and a linear actuator. The moving plate may be coupled to the first member or the second member. The alignment mechanism may, in some cases, include a first moving plate coupled to the first member and a second moving plate coupled to the second member. In some embodiments, the linear actuator is configured to move the second member along an axis orthogonal to the plane or the first member and/or the second member. For example, the moving plate may be coupled to the second member and adjust the separation distance along a z axis (e.g., orthogonal to the second substrate) by moving the moving plate up in a superior direction toward the first substrate. In some embodiments, the linear actuator is configured to move the first member along an axis orthogonal to the plane of the first member and/or the second member. The movement of the moving plate may be accomplished by the linear actuator configured to move the first member and/or the second member at a velocity. The velocity may be controlled by a controller communicatively coupled to the linear actuator. In some embodiments, the linear actuator is configured to move the first member, the second member, or both the first member and the second member at a velocity of at least 0.1 mm/sec (e.g., at least 0.1 mm/sec to 2 mm/sec). In some aspects, the velocity may be selected to reduce or minimize bubble generation or trapping within the reagent medium. In some embodiments, the linear actuator is configured to move the first member, the second member, or both the first member and the second member with an amount of force of at least 0.1 lbs. (e.g., between 0.1-4.0 pounds of force).

In some aspects, the velocity of the moving plate (e.g., closing the sandwich) may affect bubble generation or trapping within the reagent medium. It may be advantageous to minimize bubble generation or trapping within the reagent medium during the "sandwiching" process, as bubbles can interfere with the migration of analytes through the reagent medium to the array. In some embodiments, the closing speed is selected to minimize bubble generation or trapping within the reagent medium. In some embodiments, the closing speed is selected to reduce the time it takes the flow front of the reagent medium from an initial point of contact with the first and second substrate to sweep across the sandwich area (also referred to herein as "closing time"). In some embodiments, the closing speed is selected to reduce the closing time to less than about 1100 ms. In some embodiments, the closing speed is selected to reduce the closing time to less than about 1000 ms. In some embodiments, the closing speed is selected to reduce the closing time to less than about 900 ms. In some embodiments, the closing speed is selected to reduce the closing time to less than about 750 ms. In some embodiments, the closing speed is selected to reduce the closing time to less than about 600 ms. In some embodiments, the closing speed is selected to reduce the closing time to about 550 ms or less. In some embodiments, the closing speed is selected to reduce the closing time to about 370 ms or less. In some embodiments, the closing speed is selected to reduce the closing time to about 200 ms or less. In some embodiments, the closing speed is selected to reduce the closing time to about 150 ms or less.

Figure 17A:
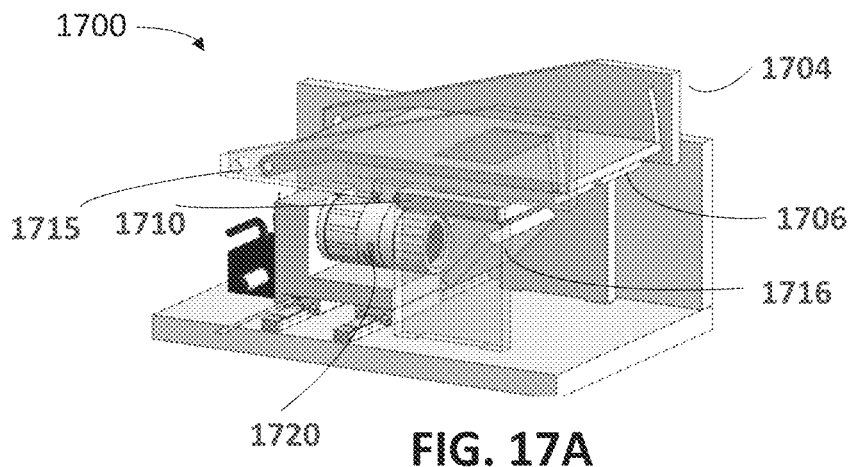
FIG. 17A shows a perspective view of an example sample handling apparatus in a closed position.

FIG. 17A is a perspective view of an example sample handling apparatus 1700 (also referred to herein as a support device, a sample holder, and an array alignment device) in a closed position in accordance with some example implementations. As shown, the sample handling apparatus 1700 includes a first member 1704, a second member 1710, optionally an image capture device 1720, a first substrate 1706, optionally a hinge 1715, and optionally a mirror 1716. The hinge 1715 may be configured to allow the first member 1704 to be positioned in an open or closed configuration by opening and/or closing the first member 1704 in a clamshell manner along the hinge 1715.

Figure 17B:
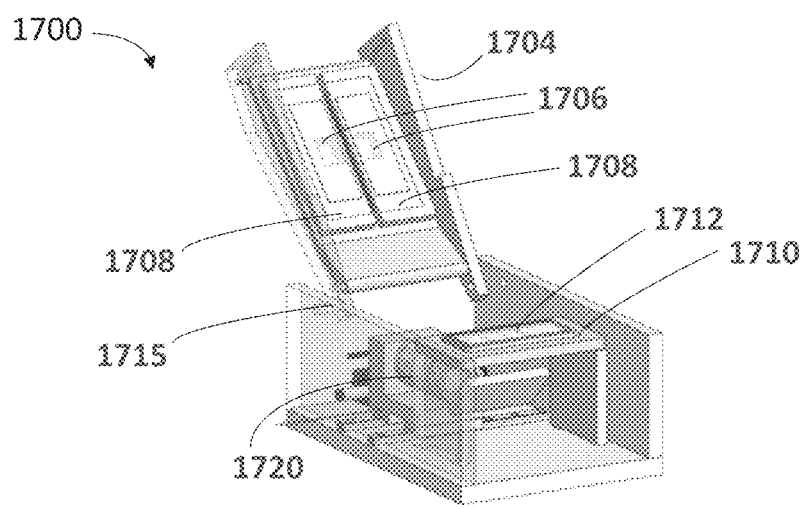
FIG. 17B shows a perspective view of the example sample handling apparatus in an open position.

FIG. 17B is a perspective view of the example sample handling apparatus 1700 in an open position in accordance with some example implementations. As shown, the sample handling apparatus 1700 includes one or more first retaining mechanisms 1708 configured to retain one or more first substrates 1706. In the example of FIG. 17B, the first member 1704 is configured to retain two first substrates 1706, however the first member 1704 may be configured to retain more or fewer first substrates 1706.

In some aspects, when the sample handling apparatus 1700 is in an open position (as in FIG. 17B), the first substrate 1706 and/or the second substrate 1712 may be loaded and positioned within the sample handling apparatus 1700 such as within the first member 1704 and the second member 1710, respectively. As noted, the hinge 1715 may allow the first member 1704 to close over the second member 1710 and form a sandwich configuration (e.g., the sandwich configuration shown in FIG. 16).

In some aspects, after the first member 1704 closes over the second member 1710, an alignment mechanism (not shown) of the sample handling apparatus 1700 may actuate the first member 1704 and/or the second member 1710 to form the sandwich configuration for the permeabilization step (e.g., bringing the first substrate 1706 and the second substrate 1712 closer to each other and within a threshold distance for the sandwich configuration). The alignment mechanism may be configured to control a speed, an angle, or the like of the sandwich configuration.

In some embodiments, the biological sample (e.g., tissue sample 1602 of FIG. 16) may be aligned within the first member 1704 (e.g., via the first retaining mechanism 1708) prior to closing the first member 1704 such that a desired region of interest of the sample 1602 is aligned with the barcoded array of the second substrate (e.g., the slide 1604), e.g., when the first and second substrates are aligned in the sandwich configuration. Note that element numbers "17XX" refer to elements from FIGS. 17A and 17B and element numbers "16XX" refer to elements in FIG. 16, wherein "XX" is any two digits. Such alignment may be accomplished manually (e.g., by a user) or automatically (e.g., via an automated alignment mechanism). After or before alignment, spacers may be applied to the first substrate 1706 and/or the second substrate 1712 to maintain a minimum spacing between the first substrate 1706 and the second substrate 1712 during sandwiching. In some aspects, the reagent medium (e.g., reagent medium 1605) may be applied to the first substrate 1706 and/or the second substrate 1712. The first member 1704 may then close over the second member 1710 and form the sandwich configuration. Analytes (including derivatives or intermediate agents such as RTL ligation products or analyte capture agents) 1608 may be captured by the capture probes 1606 and may be processed for spatial analysis.

In some embodiments, during the permeabilization step, the image capture device 1720 may capture images of the overlap area between the tissue 1602 and the capture probes 1606. If more than one first substrates 1706 and/or second substrates 1712 are present within the sample handling apparatus 1700, the image capture device 1720 may be configured to capture one or more images of one or more overlap areas. Further details on support devices, sample holders, sample handling apparatuses, or systems for implementing a sandwiching process are described in, e.g., WO 2020/123320 A2 and PCT/US2021/050931, each of which are incorporated by reference in their entirety.

Analytes within a biological sample may be released through disruption (e.g., permeabilization, digestion, etc.) of the biological sample or may be released without disruption. Various methods of permeabilizing (e.g., any of the permeabilization reagents and/or conditions described herein) a biological sample are described herein, including for example including the use of various detergents, buffers, proteases, and/or nucleases for different periods of time and at various temperatures. Additionally, various methods of delivering fluids (e.g., a buffer, a permeabilization solution) to a biological sample are described herein including the use of a substrate holder (e.g., for sandwich assembly, sandwich configuration, as described herein).

Provided herein are methods for delivering a fluid to a biological sample disposed on an area of a first substrate and an array disposed on a second substrate.

In some embodiments and with reference to FIG. 16, the sandwich configuration described herein between a first substrate comprising a biological sample (e.g., slide 1603) and a second substrate comprising a spatially barcoded array (e.g., slide 1604 with barcoded capture probes 1606) may include a reagent medium (e.g., a liquid reagent medium, e.g., a permeabilization solution 1605 or other analyte molecule release and capture solution) to fill a gap (e.g., gap 1607). It may be desirable that the reagent medium be free from air bubbles between the slides to facilitate transfer of analyte molecules with spatial information. Additionally, air bubbles present between the slides may obscure at least a portion of an image capture of a desired region of interest. Accordingly, it may be desirable to ensure or encourage suppression and/or elimination of air bubbles between the two substrates (e.g., slide 1603 and slide 1604) during a permeabilization step.

In some aspects, it may be possible to reduce or eliminate bubble formation between the slides using a variety of filling methods and/or closing methods.

Workflows described herein may include contacting a drop of the reagent medium (e.g., liquid reagent medium, e.g., a permeabilization solution 1605) disposed on a first substrate or a second substrate with at least a portion of the second substrate or first substrate, respectively. In some embodiments, the contacting comprises bringing the two substrates into proximity such that the sample on the first substrate is aligned with the barcode array of capture probes on the second substrate.

In some embodiments, the drop includes permeabilization reagents (e.g., any of the permeabilization reagents described herein). In some embodiments, the rate of permeabilization of the biological sample is modulated by delivering the permeabilization reagents (e.g., a fluid containing permeabilization reagents) at various temperatures.

In the example sandwich maker workflows described herein, the reagent medium (e.g., liquid reagent medium, permeabilization solution 1605) may fill a gap (e.g., the gap 1607) between a first substrate (e.g., slide 1603) and a second substrate (e.g., slide 1604 with barcoded capture probes 1606) to warrant or enable transfer of analyte molecules with spatial information. Described herein are examples of filling methods that may suppress bubble formation and suppress undesirable flow of transcripts and/or analyte molecules or analytes. Robust fluidics in the sandwich making described herein may preserve spatial information by reducing or preventing deflection of molecules as they move from the tissue slide to the capture slide.

Figure 18A:
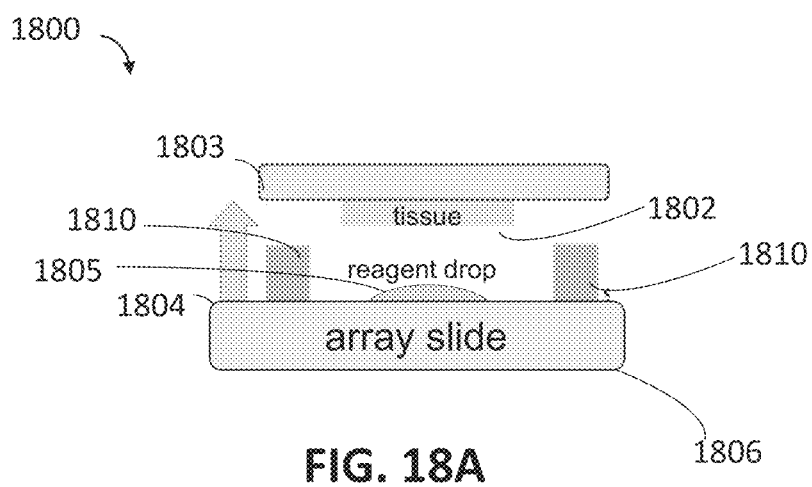
FIG. 18A shows an exemplary sandwiching process where a first substrate, including a biological sample, and a second substrate are brought into proximity with one another.

FIG. 18A shows an exemplary sandwiching process 1800 where a first substrate (e.g., slide 1803), including a biological sample 1802 (e.g., a tissue section), and a second substrate (e.g., slide 1804 including spatially barcoded capture probes 1806) are brought into proximity with one another. As shown in FIG. 18A a liquid reagent drop (e.g., permeabilization solution 1805) is introduced on the second substrate in proximity to the capture probes 1806 and in between the biological sample 1802 and the second substrate (e.g., slide 1804 including spatially barcoded capture probes 1806). The permeabilization solution 1805 may release analytes that can be captured by the capture probes 1806 of the array. As further shown, one or more spacers 1810 may be positioned between the first substrate (e.g., slide 1803) and the second substrate (e.g., slide 1804 including spatially barcoded capture probes 1806). The one or more spacers 1810 may be configured to maintain a separation distance between the first substrate and the second substrate. While the one or more spacers 1810 is shown as disposed on the second substrate, the spacer may additionally or alternatively be disposed on the first substrate.

In some embodiments, the one or more spacers 1810 is configured to maintain a separation distance between first and second substrates that is between about 2 microns and 1 mm (e.g., between about 2 microns and 800 microns, between about 2 microns and 700 microns, between about 2 microns and 600 microns, between about 2 microns and 500 microns, between about 2 microns and 400 microns, between about 2 microns and 300 microns, between about 2 microns and 200 microns, between about 2 microns and 100 microns, between about 2 microns and 25 microns, or between about 2 microns and 10 microns), measured in a direction orthogonal to the surface of first substrate that supports the sample. In some instances, the separation distance is about 2, 3, 4, 5, 6, 7, 8, 9, 10, 11, 12, 13, 14, 15, 16, 17, 18, 19, 20, 21, 22, 23, 24, or 25 microns. In some embodiments, the separation distance is less than 50 microns. In some embodiments, the separation distance is less than 25 microns. In some embodiments, the separation distance is less than 20 microns. The separation distance may include a distance of at least 2 µm.

Figure 18B:
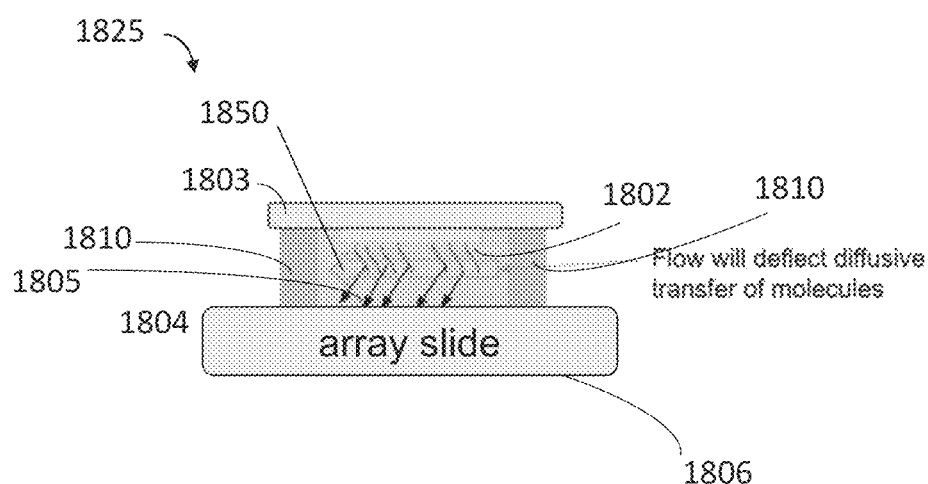
FIG. 18B shows a fully formed sandwich configuration creating a chamber formed from the one or more spacers, the first substrate, and the second substrate.

FIG. 18B shows a fully formed sandwich configuration creating a chamber 1850 formed from the one or more spacers 1810, the first substrate (e.g., the slide 1803), and the second substrate (e.g., the slide 304 including spatially barcoded capture probes 1806) in accordance with some example implementations. In the example of FIG. 18B, the liquid reagent (e.g., the permeabilization solution 1805) fills the volume of the chamber 1850 and may create a permeabilization buffer that allows analytes, RTL ligation products, and analyte capture agents to diffuse from the biological sample 1802 toward the capture probes 1806 of the second substrate (e.g., slide 1804). In some aspects, flow of the permeabilization buffer may deflect transcripts and/or molecules from the biological sample 1802 and may affect diffusive transfer of analytes for spatial analysis. A partially or fully sealed chamber 1850 resulting from the one or more spacers 1810, the first substrate, and the second substrate may reduce or prevent flow from undesirable convective movement of transcripts and/or molecules over the diffusive transfer from the biological sample 1802 to the capture probes 1806.

In some instances, the first substrate and the second substrate are arranged in an angled sandwich assembly as described herein. For example, during the sandwiching of the two substrates (e.g., the slide 1803 and the slide 1804), an angled closure workflow may be used to suppress or eliminate bubble formation.

FIGS. 19A-19C depict a side view and a top view of an exemplary angled closure workflow 1900 for sandwiching a first substrate (e.g., slide 1903) having a biological sample 1902 and a second substrate (e.g., slide 1904 having capture probes 1906) in accordance with some example implementations.

FIG. 19A depicts the first substrate (e.g., the slide 1903 including biological sample 1902) angled over (superior to) the second substrate (e.g., slide 1904). As shown, a drop of the reagent medium (e.g., permeabilization solution) 1905 is located on the spacer 1910 toward the right-hand side of the side view in FIG. 19A. While FIG. 19A depicts the reagent medium on the right hand side of side view, it should be understood that such depiction is not meant to be limiting as to the location of the reagent medium on the spacer.

FIG. 19B shows that as the first substrate lowers, and/or as the second substrate rises, the dropped side of the first substrate (e.g., a side of the slide 1903 angled toward the second substrate) may contact the drop of the reagent medium 1905. The dropped side of the first substrate may urge the reagent medium 1905 toward the opposite direction (e.g., towards an opposite side of the spacer 1910, towards an opposite side of the first substrate relative to the dropped side). For example, in the side view of FIG. 19B the reagent medium 1905 may be urged from right to left as the sandwich is formed.

In some embodiments, the first substrate and/or the second substrate are further moved to achieve an approximately parallel arrangement of the first substrate and the second substrate.

FIG. 19C depicts a full closure of the sandwich between the first substrate and the second substrate with the spacer 1910 contacting both the first substrate and the second substrate and maintaining a separation distance and optionally the approximately parallel arrangement between the two substrates. As shown in the top view of FIG. 19C, the spacer 1910 fully encloses and surrounds the biological sample 1902 and the capture probes 1906, and the spacer 1910 forms the sides of chamber 1950 which holds a volume of the reagent medium 1905.

It should be understood that while FIGS. 19A-19C depict the first substrate (e.g., the slide 1903 including biological sample 1902) angled over (superior to) the second substrate (e.g., slide 1904) and the second substrate comprising the spacer 1910, it should be understood that an exemplary angled closure workflow can include the second substrate angled over (superior to) the first substrate and the first substrate comprising the spacer 1910.

FIGS. 20A-20E depict an example workflow 2000 for an angled sandwich assembly in accordance with some example implementations. As shown in FIG. 20A, a substrate 2012 (e.g., comprising a first substrate such as slide 1603 or a second substrate such as slide 1604 comprising spatially barcoded capture probes 1606, as shown in FIG. 16) may be positioned and placed on a base 2004 (e.g., a first member or a second member of a sample holder disclosed herein) with a side of the substrate 2012 supported by a spring 2015. The spring 2015 may extend from the base 2004 in a superior direction and may be configured to dispose the substrate 2012 along a plane angled differently than the base 2004. The angle of the substrate 2012 may be such that a drop of reagent medium 2005 (e.g., drop of liquid reagent medium) placed on the surface of the substrate 2012 (e.g., a surface of a spacer attached to the substrate) will not fall off the surface (e.g., due to gravity). The angle may be determined based on a gravitational force versus any surface force to move the drop away from and off the substrate 2012.

FIG. 20B depicts a drop 2005 of reagent medium placed on the substrate 2012. As shown, the drop 2005 is located on the side of the substrate 2012 contacting the spring 2015 and is located in proximity and above (superior to) the spring 2015.

As shown in FIG. 20C, another substrate 2006 may be positioned above (superior to) the substrate 2012 and at an angle substantially parallel with the base 2004. For example, in cases wherein substrate 2012 is a second substrate disclosed herein (e.g., slide 1604 from FIG. 16 comprising spatially barcoded capture probes), substrate 2006 may be a first substrate disclosed herein (e.g., slide 1603). In cases wherein substrate 2012 is a first substrate disclosed herein (e.g., slide 1603), substrate 2006 may be a second substrate (e.g., slide 1604 comprising spatially barcoded capture probes).

In some cases, another base (not shown) supporting substrate 2006 (e.g., a first member or a second member of a sample holder disclosed herein) may be configured to retain substrate 1706 at the angle substantially parallel to the base 2004.

As shown in FIG. 20D, substrate 2006 may be lowered toward the substrate 2012 such that a dropped side of the substrate 2006 contacts the drop 2005 first. In some aspects, the dropped side of the substrate 2006 may urge the drop 2005 toward the opposite side of the substrate 2006. In some embodiments, the substrate 2012 may be moved upward toward the substrate 2006 to accomplish the contacting of the dropped side of the substrate 2006 with the drop 2005.

FIG. 20E depicts a full sandwich closure of the substrate 2006 and the substrate 2012 with the drop of reagent medium 2005 positioned between the two sides. In some aspects and as shown, as the substrate 2006 is lowered onto the drop 2005 and toward the substrate 2012 (and/or as the substrate 2012 is raised up toward the substrate 2006), the spring 2015 may compress and the substrate 2012 may lower to the base 2004 and become substantially parallel with the substrate 2006.

Figures 21A, 21B:
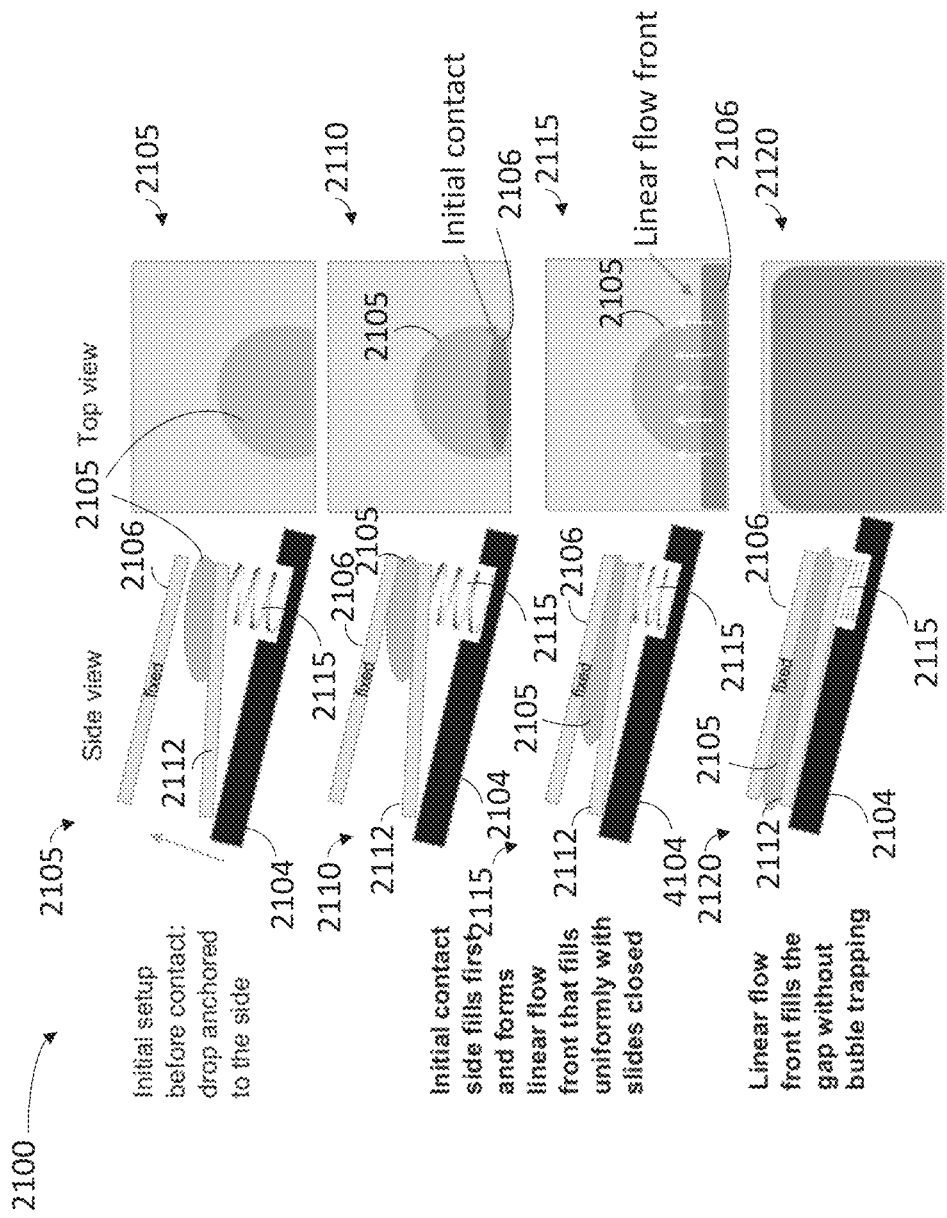
FIG. 21A shows a side view of the angled closure workflow.
FIG. 21B shows a top view of the angled closure workflow.

FIG. 21A is a side view of the angled closure workflow 2100 in accordance with some example implementations. FIG. 21B is a top view of the angled closure workflow 2100 in accordance with some example implementations. As shown at 2105 and in accordance with FIGS. 20C-20D, the drop of reagent medium 2105 is positioned to the side of the substrate 2112 contacting the spring 2115.

At step 2110, the dropped side of the angled substrate 2106 contacts the drop of reagent medium 2105 first. The contact of the substrate 2106 with the drop of reagent medium 2105 may form a linear or low curvature flow front that fills uniformly with the slides closed.

At step 2115, the substrate 2106 is further lowered toward the substrate 2112 (or the substrate 2112 is raised up toward the substrate 2106) and the dropped side of the substrate 2106 may contact and may urge the liquid reagent toward the side opposite the dropped side and creating a linear or low curvature flow front that may prevent or reduce bubble trapping between the slides. As further shown, the spring 2115 may begin to compress as the substrate 2106 is lowered.

At step 2120, the drop of reagent medium 2105 fills the gap (e.g., the gap 1607 as shown in FIG. 16) between the substrate 2106 and the substrate 2112. The linear flow front of the liquid reagent may form by squeezing the drop 2105 volume along the contact side of the substrate 2112 and/or the substrate 2106. Additionally, capillary flow may also contribute to filling the gap area. As further shown in step 2120, the spring 2115 may be fully compressed such that the substrate 2106, the substrate 2112, and the base 2104 are substantially parallel to each other.

In some aspects, an angled closure workflow disclosed herein (e.g., FIGS. 19A-19C, 20A-40E, and 21A-21B) may be performed by a sample handling apparatus (e.g., as described in PCT/US2021/050931, which is hereby incorporated by reference in its entirety.

Further details on angled closure workflows, and devices and systems for implementing an angled closure workflow, are described in PCT/US2021/036788 and PCT/US2021/050931, which are hereby incorporated by reference in their entirety.

Additional configurations for reducing or eliminating bubble formation, and/or for reducing unwanted fluid flow, are described in PCT/US2021/036788, which is hereby incorporated by reference in its entirety.

In some embodiments, the reagent medium comprises a permeabilization agent. Suitable agents for this purpose include, but are not limited to, organic solvents (e.g., acetone, ethanol, and methanol), cross-linking agents (e.g., paraformaldehyde), detergents (e.g., saponin, Triton X100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). Exemplary permeabilization reagents are described in in US. Patent Application Pub. No. 20210189475, which is incorporated by reference in its entirety.

In some embodiments, the reagent medium comprises a lysis reagent. Lysis solutions can include ionic surfactants such as, for example, sarkosyl and sodium dodecyl sulfate (SDS). More generally, chemical lysis agents can include, without limitation, organic solvents, chelating agents, detergents, surfactants, and chaotropic agents. Exemplary lysis reagents are described in US. Patent Application Pub. No. 20210189475, which is incorporated by reference in its entirety.

In some embodiments, the reagent medium comprises a protease. Exemplary proteases include, e.g., pepsin, trypsin, pepsin, elastase, and proteinase K. Exemplary proteases are described in US. Patent Application Pub. No. 20210189475, which is incorporated by reference in its entirety.

In some embodiments, the reagent medium comprises a detergent. Exemplary detergents include sodium dodecyl sulfate (SDS), sarkosyl, saponin, Triton X-100™, and Tween-20™. Exemplary detergents are described in US. Patent Application Pub. No. 20210189475, which is incorporated by reference in its entirety.

In some embodiments, the reagent medium comprises a nuclease. In some embodiments, the nuclease comprises an RNase. In some embodiments, the RNase is selected from RNase A, RNase C, RNase H, and RNase I. In some embodiments, the reagent medium comprises one or more of sodium dodecyl sulfate (SDS), proteinase K, pepsin, N-lauroylsarcosine, RNase, and a sodium salt thereof.

In some embodiments, the reagent medium comprises an agent for releasing a connected probe disclosed herein and a permeabilization agent. In some embodiments, the agent for releasing the connected probe comprises or is a nuclease, e.g., RNase, and the permeabilization agent is a protease (e.g., proteinase K, trypsin, pepsin, elastase).

In some embodiments, the reagent medium comprises polyethylene glycol (PEG). In some embodiments, the PEG is from about PEG 2K to about PEG 16K. In some embodiments, the PEG is PEG 2K, 3K, 4K, 5K, 6K, 7K, 8K, 9K, 10K, 11K, 12K, 13K, 14K, or 16K. In some embodiments, the PEG is present at a concentration from about 2% to 25%, from about 4% to about 23%, from about 6% to about 21%, or from about 8% to about 20% (v/v).

In some embodiments, the reagent medium includes a wetting agent.

The sample holder is compatible with a variety of different schemes for contacting the aligned portions of the biological sample and array with the reagent medium to promote analyte capture. In some embodiments, the reagent medium is deposited directly on the second substrate (e.g., forming a reagent medium that includes the permeabilization reagent and the feature array), and/or directly on the first substrate. In some embodiments, the reagent medium is deposited on the first and/or second substrate, and then the first and second substrates aligned in the sandwich configuration such that the reagent medium contacts the aligned portions of the biological sample and array. In some embodiments, the reagent medium is introduced into the gap 307 while the first and second substrates are aligned in the sandwich configuration.

In certain embodiments a dried permeabilization reagent is applied or formed as a layer on the first substrate or the second substrate or both prior to contacting the sample and the feature array. For example, a reagent can be deposited in solution on the first substrate or the second substrate or both and then dried. Drying methods include, but are not limited to spin coating a thin solution of the reagent and then evaporating a solvent included in the reagent or the reagent itself. Alternatively, in other embodiments, the reagent can be applied in dried form directly onto the first substrate or the second substrate or both. In some embodiments, the coating process can be done in advance of the analytical workflow and the first substrate and the second substrate can be stored pre-coated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid). In some instances, the substrate that includes the sample (e.g., a histological tissue section) is hydrated. The sample can be hydrated by contacting the sample with a reagent medium, e.g., a buffer that does not include a permeabilization reagent. In some embodiments, the hydration is performed while the first and second substrates are aligned in a sandwich configuration.

In some instances, the aligned portions of the biological sample and the array are in contact with the reagent medium 305 for about 1 minute. In some instances, the aligned portions of the biological sample and the array are in contact with the reagent medium 1605 for about 5 minutes. In some instances, the aligned portions of the biological sample and the array are in contact with the reagent medium 305 in the gap 307 for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium 1605 for about 1-60 minutes. In some instances, the aligned portions of the biological sample and the array are in contact with the reagent medium 305 for about 30 minutes.

In some embodiments, following initial contact between sample and a permeabilization agent, the permeabilization agent can be removed from contact with sample (e.g., by opening sample holder).

In some instances, the device is configured to control a temperature of the first and second substrates. In some embodiments, the temperature of the first and second members is lowered to a first temperature that is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower). In some embodiments, the device includes a temperature control system (e.g., heating and cooling conducting coils) to control the temperature of the sample holder. Alternatively, in other embodiments, the temperature of the sample holder is controlled externally (e.g., via refrigeration or a hotplate). In a first step, the second member, set to or at the first temperature, contacts the first substrate, and the first member, set to or at the first temperature, contacts the second substrate, thereby lowering the temperature of the first substrate and the second substrate to a second temperature. In some embodiments, the second temperature is equivalent to the first temperature. In some embodiments, the first temperature is lower than room temperature (e.g., 25 degrees Celsius). In some embodiments, the second temperature ranges from about −10 degrees Celsius to about 4 degrees Celsius. In some embodiments, the second temperature is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower).

In an exemplary embodiment, the second substrate is contacted with the permeabilization reagent. In some embodiments, the permeabilization reagent is dried. In some embodiments, the permeabilization reagent is a gel or a liquid. Also in the exemplary embodiment, the biological sample is contacted with buffer. Both the first and second substrates are placed at lower temperature to slow down diffusion and permeabilization efficiency. Alternatively, in some embodiments, the sample can be contacted directly with a liquid permeabilization reagent without inducing an unwanted initiation of permeabilization due to the substrates being at the second temperature. In some embodiments, the low temperature slows down or prevents the initiation of permeabilization. In a second step, keeping the sample holder and substrates at a cold temperature (e.g., at the first or second temperatures) continues to slow down or prevent the permeabilization of the sample. In a third step, the sample holder (and consequently the first and second substrates) is heated up to initiate permeabilization. In some embodiments, the sample holder is heated up to a third temperature. In some embodiments, the third temperature is above room temperature (e.g., degrees Celsius) (e.g., 30 degrees Celsius or higher, 35 degrees Celsius or higher, 40 degrees Celsius or higher, 50 degrees Celsius or higher, 60 degrees Celsius or higher). In some embodiments, analytes that are released from the permeabilized tissue of the sample diffuse to the surface of the second substrate and are captured on the array (e.g., barcoded probes) of the second substrate. In a fourth step, the first substrate and the second substrate are separated (e.g., pulled apart) and temperature control is stopped.

In certain embodiments, a permeabilization solution can be soaked into a hydrogel film that is applied directly to the sample, and/or soaked into features (e.g., beads) of the array. When the first and second substrates are aligned in the sandwich configuration, the permeabilization solution promotes migration of analytes from the sample to the array.

In certain embodiments, different permeabilization agents or different concentrations of permeabilization agents can be infused into array features (e.g., beads) or into a hydrogel layer as described above. By locally varying the nature of the permeabilization reagent(s), the process of analyte capture from the sample can be spatially adjusted.

In some instances, migration of the analyte from the biological sample to the second substrate is passive (e.g., via diffusion). Alternatively, in certain embodiments, migration of the analyte from the biological sample is performed actively (e.g., electrophoretic, by applying an electric field to promote migration). In some instances, first and second substrates can include a conductive epoxy. Electrical wires from a power supply can connect to the conductive epoxy, thereby allowing a user to apply a current and generate an electric field between the first and second substrates. In some embodiments, electrophoretic migration results in higher analyte capture efficiency and better spatial fidelity of captured analytes (e.g., on a feature array) than random diffusion onto matched substrates without the application of an electric field (e.g., via manual alignment of the two substrates). Exemplary methods of electrophoretic migration are described in WO 2020/176788, including at FIGS. 13-15, 24A-24B, and 25A-25C, which is hereby incorporated by reference in its entirety.

Loss of spatial resolution can occur when analytes migrate from the sample to the feature array and a component of diffusive migration occurs in the transverse (e.g., lateral) direction, approximately parallel to the surface of the first substrate on which the sample is mounted. To address this loss of resolution, in some embodiments, a permeabilization agent deposited on or infused into a material with anisotropic diffusion can be applied to the sample or to the feature array. The first and second substrates are aligned by the sample holder and brought into contact. A permeabilization layer that includes a permeabilization solution infused into an anisotropic material is positioned on the second substrate.

In some embodiments, the feature array can be constructed atop a hydrogel layer infused with a permeabilization agent. The hydrogel layer can be mounted on the second substrate, or alternatively, the hydrogel layer itself may function as the second substrate. When the first and second substrates are aligned, the permeabilization agent diffuses out of the hydrogel layer and through or around the feature array to reach the sample. Analytes from the sample migrate to the feature array. Direct contact between the feature array and the sample helps to reduce lateral diffusion of the analytes, mitigating spatial resolution loss that would occur if the diffusive path of the analytes was longer.

Spatial analysis workflows can include a sandwiching process described herein, e.g., a process as described in FIG. 16. In some embodiments, the workflow includes provision of the first substrate comprising the biological sample. In some embodiments, the workflow includes mounting the biological sample onto the first substrate. In some embodiments wherein the biological sample is a tissue sample, the workflow include sectioning of the tissue sample (e.g., cryostat sectioning). In some embodiments, the workflow includes a fixation step. In some instances, the fixation step can include fixation with methanol. In some instances, the fixation step includes formalin (e.g., 2% formalin).

In some embodiments, the biological sample on the first substrate is stained using any of the methods described herein. In some instances, the biological sample is imaged, capturing the stain pattern created during the stain step. In some instances, the biological sample then is destained prior to the sandwiching process.

The biological sample can be stained using known staining techniques, including, without limitation, Can-Grunwald, Giemsa, hematoxylin and eosin (H&E), hematoxylin, Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes biological staining using hematoxylin. In some embodiments, staining includes identifying analytes using fluorescently-conjugated antibodies, e.g., by immunofluorescence. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample. In some instances, a biological sample on the first substrate is stained.

In some instances, methods for immunofluorescence include a blocking step. The blocking step can include the use of blocking probes to decrease unspecific binding of the antibodies. The blocking step can optionally further include contacting the biological sample with a detergent. In some instances, the detergent can include Triton X100™. The method can further include an antibody incubation step. In some embodiments, the antibody incubation step effects selective binding of the antibody to antigens of interest in the biological sample. In some embodiments, the antibody is conjugated to an oligonucleotide (e.g., an oligonucleotide-antibody conjugate as described herein). In some embodiments, the antibody is not conjugated to an oligonucleotide. In some embodiments, the method further comprises an antibody staining step. The antibody staining step can include a direct method of immunostaining in which a labelled antibody binds directly to the analyte being stained for. Alternatively, the antibody staining step can include an indirect method of immunostaining in which a first antibody binds to the analyte being stained for, and a second, labelled antibody binds to the first antibody. In some embodiments, the antibody staining step is performed prior to sandwich assembly. In some embodiments wherein an oligonucleotide-antibody conjugate is used in the antibody incubation step, the method does not comprise an antibody staining step.

In some instances, the methods include subjecting the biological sample to an in situ assay disclosed herein.

In some instances, the methods include imaging the biological sample. In some instances, imaging occurs prior to sandwich assembly. In some instances, imaging occurs while the sandwich configuration is assembled. In some instances, imaging occurs during permeabilization of the biological sample. In some instances, image are captured using high resolution techniques (e.g., having 300 dots per square inch (dpi) or greater). For example, images can be captured using brightfield imaging (e.g., in the setting of hematoxylin or H&E stain), or using fluorescence microscopy to detect adhered labels. In some instances, high resolution images are captured temporally using e.g., confocal microscopy. In some instances, a low resolution image is captured. A low resolution image (e.g., images that are about 72 dpi and normally have an RGB color setting) can be captured at any point of the workflow, including but not limited to staining, destaining, permeabilization, sandwich assembly, and migration of the analytes. In some instances, a low resolution image is taken during permeabilization of the biological sample.

In some embodiments, the location of the one or more additional analytes in a biological sample are determined by immunofluorescence. In some embodiments, one or more detectable labels (e.g., fluorophore-labeled antibodies, nucleic acid probes disclosed herein) bind to the one or more analytes that are captured (hybridized to) by a probe on the first slide and the location of the one or more analytes is determined by detecting the labels under suitable conditions. In some embodiments, one or more fluorophore-labeled antibodies are used to conjugate to a moiety that associates with a probe on the first slide or the analyte that is hybridized to the probe on the first slide. In some instances, the location(s) of the one or more analytes is determined by imaging the fluorophore-labeled antibodies when the fluorophores are excited by a light of a suitable wavelength. In some embodiments, the location of the one or more analytes in the biological sample is determined by correlating the immunofluorescence data to an image of the biological sample. In some instances, the tissue is imaged throughout the permeabilization step.

In some instances, the biological samples can be destained. In some instances, destaining occurs prior to permeabilization of the biological sample. By way of example only, H&E staining can be destained by washing the sample in HCl. In some instances, the hematoxylin of the H&E stain is destained by washing the sample in HCl. In some embodiments, destaining can include 1, 2, 3, or more washes in HCl. In some embodiments, destaining can include adding HCl to a downstream solution (e.g., permeabilization solution). Between any of the methods disclosed herein, the methods can include a wash step (e.g., with SSC (e.g., 0.1×SSC)). Wash steps can be performed once or multiple times (e.g., 1×, 2×, 3×, between steps disclosed herein). In some instances, wash steps are performed for about 10 seconds, about 15 seconds, about 20 seconds, about 30 seconds, or about a minute. In some instances, three washes occur for 20 seconds each. In some instances, the wash step occurs before staining the sample, after destaining the sample, before permeabilization the sample, after permeabilization the sample, or any combination thereof.

In some instances, after the sandwiching process the first substrate and the second substrate are separated (e.g., such that they are no longer aligned in a sandwich configuration, also referred to herein as opening the sandwich). In some embodiments, subsequent analysis (e.g., cDNA synthesis, library preparation, and sequences) can be performed on the captured analytes after the first substrate and the second substrate are separated.

In certain embodiments a dried permeabilization reagent is applied or formed as a layer on the first substrate or the second substrate or both prior to contacting the sample and the feature array. For example, a reagent can be deposited in solution on the first substrate or the second substrate or both and then dried. Drying methods include, but are not limited to spin coating a thin solution of the reagent and then evaporating a solvent included in the reagent or the reagent itself. Alternatively, in other embodiments, the reagent can be applied in dried form directly onto the first substrate or the second substrate or both. In some embodiments, the coating process can be done in advance of the analytical workflow and the first substrate and the second substrate can be stored pre-coated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid). In some instances, the substrate that includes the sample (e.g., a histological tissue section) is hydrated. The sample can be hydrated by contacting the sample with a reagent medium, e.g., a buffer that does not include a permeabilization reagent. In some embodiments, the hydration is performed while the first and second substrates are aligned in a sandwich configuration.

In some instances, the aligned portions of the biological sample and the array are in contact with the reagent medium for about 1 minute. In some instances, the aligned portions of the biological sample and the array are in contact with the reagent medium for about 5 minutes. In some instances, the aligned portions of the biological sample and the array are in contact with the reagent medium in the gap between the first substrate and the second substrate for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium for about 1-60 minutes. In some instances, the aligned portions of the biological sample and the array are in contact with the reagent medium for about 30 minutes.

In some embodiments, following initial contact between sample and a permeabilization agent, the permeabilization agent can be removed from contact with sample (e.g., by opening sample holder) before complete permeabilization of sample. For example, in some embodiments, only a portion of sample is permeabilized, and only a portion of the analytes in sample may be captured by feature array. In some instances, the reduced amount of analyte captured and available for detection can be offset by the reduction in lateral diffusion that results from incomplete permeabilization of sample. In general, the spatial resolution of the assay is determined by the extent of analyte diffusion in the transverse direction (e.g. or i.e., orthogonal to the normal direction to the surface of sample). The larger the distance between the sample on the first substrate and the feature array on the second substrate, the greater the extent of diffusion in the transverse direction, and the concomitant loss of resolution. Analytes liberated from a portion of the sample closest to the feature array have a shorter diffusion path, and therefore do not diffuse as far laterally as analytes from portions of the sample farthest from the feature array. As a result, in some instances, incomplete permeabilization of the sample (by reducing the contact interval between the permeabilization agent and the sample) can be used to maintain adequate spatial resolution in the assay.

(d) Analysis of Tagged and/or Captured Analytes

After analytes from the sample have hybridized or otherwise been associated with capture probes, analyte capture agents, or other barcoded oligonucleotide sequences according to any of the methods described above in connection with the general spatial analysis methodology, the barcoded constructs that result from hybridization/association may be extended, amplified, purified, and analyzed via sequencing to identify the location and abundance of the analytes in the biological sample.

In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe. An extended capture probe can include additional nucleotides added to the terminus (e.g., 3' or 5' end) of the capture probe thereby extending the overall length of the capture probe. In some instances, polymerization reactions are used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, after hybridizing to a capture probe, a connected probe (e.g., a ligation product) is extended. In some embodiments, extending the connected probe includes adding to a 3' end of a connected probe a nucleic acid sequence that is complementary to a nucleic acid sequence of the capture probe specifically bound to the 3' end of the connected probe. In some embodiments, the connected probe (e.g., a ligation product) is extended using reverse transcription. In some embodiments, the connected probe is extended using one or more DNA polymerases. The extended connected probes include the sequence of the connected probe and the sequence of the capture probe to which the connected probe hybridized. An extended connected probe can include additional nucleotides added to the terminus (e.g., 3' or 5' end) of the connected probe thereby extending the overall length of the connected probe. In some embodiments, extending the connected probe includes adding to a 3' end of a connected probe a nucleic acid sequence that is complementary to a nucleic acid sequence of a capture probe specifically bound to a domain of the connected probe. In some embodiments, the capture probe and the connected probe are both extended, with the capture probe acting as a template for the extension of the connected probe and the connected probe acting as a template for the extension of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

A wide variety of different sequencing methods can be used to analyze barcoded analyte constructs. Sequencing methods have been described previously in PCT Publ. No. WO 2020/176788 and/or U.S. Patent Application Publication No. 2020/0277663, each of which is incorporated by reference. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog). Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

In some embodiments, a method disclosed herein comprises correlating, comparing and/or integrating a result of the in situ assay with a result of the spatial assay. In some embodiments, a method disclosed herein comprises correlating, comparing and/or integrating the presence/absence, distribution, location, amount, level, expression, or activity of a first analyte (e.g., a first nucleic acid or protein analyte) from the in situ assay with the presence/absence, distribution, location, amount, level, expression, or activity of a second analyte (e.g., a second nucleic acid or protein analyte) from the spatial assay.

In some embodiments, disclosed herein is a method of analyzing a biological sample, comprising contacting a biological sample on a first substrate with one or more probes comprising nucleic acid molecules that directly or indirectly hybridize to a first analyte which is a nucleic acid (or a complement or an amplification product thereof) in the biological sample. The first analyte may be an RNA molecule. In some embodiments, the method further comprises detecting the one or more probes at a spatial location of the biological sample, and providing conditions to allow a plurality of capture probes to capture a second analyte, which may be a protein analyte. In some embodiments, the protein analyte is bound by an analyte capture agent comprising a nucleic acid label that corresponds to the analyte capture agent and/or the protein analyte, and a capture probe may capture the nucleic acid label, thereby capturing the protein analyte. The captured nucleic acid label (corresponding to the analyte capture agent and/or the protein analyte), or a complement thereof or an amplification product thereof, may be analyzed in a spatial assay. For example, the plurality of capture probes may be provided on a second substrate, and a capture probe of the plurality of capture probes comprises a capture domain capable of capturing a nucleic acid (e.g., the nucleic acid label), and a spatial barcode corresponding to the position of the capture probe on the second substrate. In some embodiments, the method further comprises generating a spatially labeled polynucleotide comprising (i) a sequence of the nucleic acid label (corresponding to the analyte capture agent and/or the protein analyte) or complement thereof and (ii) a sequence of the spatial barcode or complement thereof. In any of the embodiments herein, the biological sample may be contacted with the analyte capture agent for the protein analyte before, during, or after detecting the one or more probes at a spatial location of the sample. In any of the embodiments herein, the biological sample may be contacted with the analyte capture agent for the protein analyte before, during, or after an in situ analysis module performed on the sample for the first analyte which is a nucleic acid. In some embodiments, the protein analyte or a subunit or polypeptide sequence thereof can be encoded by a sequence of the nucleic acid analyte.

In some embodiments, disclosed herein is a method of analyzing a biological sample, comprising contacting a biological sample on a first substrate with one or more probes comprising nucleic acid molecules that directly or indirectly hybridize to a nucleic acid label (or a complement or an amplification product thereof) of an analyte capture agent that binds a first analyte which is a non-nucleic acid analyte in the biological sample. The first analyte may be a protein. The nucleic acid label may correspond to the analyte capture agent and/or the protein analyte. In some embodiments, the method further comprises detecting the one or more probes at a spatial location of the biological sample, and providing conditions to allow a plurality of capture probes to capture a second analyte which is a nucleic acid analyte such as an mRNA. The captured nucleic acid analyte, or a complement thereof or an amplification product thereof, may be analyzed in a spatial assay. For example, the plurality of capture probes may be provided on a second substrate, and a capture probe of the plurality of capture probes comprises a capture domain capable of capturing a nucleic acid (e.g., the nucleic acid analyte such as an mRNA), and a spatial barcode corresponding to the position of the capture probe on the second substrate. In some embodiments, the method further comprises generating a spatially labeled polynucleotide comprising (i) a sequence of the nucleic acid analyte such as an mRNA or complement thereof and (ii) a sequence of the spatial barcode or complement thereof. In any of the embodiments herein, the protein analyte or a subunit or polypeptide sequence thereof can be encoded by a sequence of the nucleic acid analyte.

In some embodiments, a method disclosed herein integrates intact tissue features from a first set of analytes in a sample in situ with assay steps capable of whole transcriptome, nucleotide resolution (e.g., full RNA sequences) analysis of a second set of analytes in the same sample. In some embodiments, the first and second set of analytes comprises nucleic acid sequences of interest. In some embodiments, the first and second set of analytes are mRNA transcripts. In some embodiments, the first set of analytes are a subset of the second set of analytes, e.g., the first set being a panel of mRNA transcripts for targeted analysis and the second set being the whole transcriptome or a subset thereof for a non-targeted analysis. In some embodiments, the first set of analytes comprise protein analytes and the second set of analytes comprise nucleic acid molecules (e.g., mRNA transcripts) that correspond to at least some of the protein analytes.

In some embodiments, a method disclosed herein comprises in situ analysis of a first set of analytes in a spatially intact tissue context and spatial analysis of a second set of analytes, where the spatial analysis may be confirmatory or supplemental to the in situ analysis. In some embodiments, the in situ analysis comprises a 2D analysis of a biological sample, e.g., a tissue section isolated from an organism or a tissue culture on a substrate. In some embodiments, the in situ analysis comprises a 3D analysis of a biological sample, e.g., a tissue section isolated from an organism or a tissue culture such as an organoid culture in 3D form.

In some embodiments, a method disclosed herein comprises in situ analysis of a first set of nucleic acid or protein analytes, e.g., for cell phenotyping in a tissue sample by using the nucleic acid or protein analytes as biomarkers, and spatial analysis of a second set of nucleic acid analytes, e.g., for deeper sequencing of many other nucleic acid molecules (e.g., mRNAs) in a discovery mode, for example, to identify nucleic acid molecules associated with one or more particular cell phenotype.

In some embodiments, a method disclosed herein comprises using a result from the in situ analysis of a sample to validate a result from the spatial assay of the same sample. For instance, in situ analysis results of a set of nucleic acid or protein analytes may be used to validate the spatial analysis of the same or related nucleic acid analytes or the nucleic acid molecules (DNA sequences from a spatial genomics analysis or RNA transcript sequences from a spatial transcriptomics analysis) that correspond to the protein analytes analyzed in situ. In another example, results of spatial analysis of a set of nucleic acid analytes may be used to validate the in situ analysis of the same or related nucleic acid analytes, e.g., by providing information of tissue morphology and/or spatial relationship of a nucleic acid analyte with regard to the tissue morphology and/or other molecules in the tissue.

In some embodiments, a method disclosed herein comprises in situ analysis of one or more protein analytes in a sample and spatial analysis of one or more nucleic acid analytes, e.g., mRNAs, in the same sample. In some embodiments, the in situ analysis comprises contacting the sample with one or more probes, where a probe comprises an analyte-binding moiety (e.g., an antibody) that binds a protein analyte or a portion (e.g., an epitope) thereof and a nucleic acid barcode sequence that corresponds to the analyte-binding moiety and/or the protein analyte or portion thereof. In some embodiments, the in situ analysis further comprises analyzing the one or more probes, e.g., by optical imaging. For example, the one or more probes may be barcoded probes comprising one or more nucleic acid barcode sequences, which can be directly or indirectly bound by detectably-labeled detection probes. A detectable signal or a series of signals such as fluorescence comprising a spatial pattern and/or a temporal pattern may be analyzed to reveal the presence/absence, distribution, location, amount, level, expression, or activity of the one or more protein analytes in the sample. In some embodiments, the one or more protein analytes are analyzed (e.g., by imaging) in situ in a tissue sample without migrating out of a cell of the tissue sample. In some embodiments, the one or more protein analytes are analyzed (e.g., by imaging) in situ in a tissue sample without migrating out of the tissue sample, e.g., onto a substrate. In some embodiments, the probe comprises the analyte-binding moiety (e.g., antibody) and the nucleic acid barcode sequence is not cleaved during the in situ analysis. For example, for the in situ analysis, the nucleic acid barcode sequence is not released from the analyte-binding moiety (e.g., antibody) of the probe bound to the protein analyte or captured by a capture agent on a substrate; however, after the in situ analysis, the nucleic acid barcode sequence may be released and captured by a capture agent for spatial analysis together with other nucleic acid molecules (e.g., mRNA transcripts) released from the sample.

In some embodiments, a method disclosed herein comprises in situ analysis of one or more non-polyadenylated analytes (e.g., non-polyadenylated mRNA transcripts) in a sample, and spatial analysis of one or more polyadenylated analytes (e.g., mRNAs transcripts with poly-A tails) in the same sample.

In some embodiments, a method disclosed herein comprises in situ analysis of a first region of a tissue sample and spatial analysis of a second region in the same tissue sample. In some embodiments, the first and second regions do not overlap. In some embodiments, the first and second regions overlap. The regions may be identical or one region may be entirely within the other region. In an example, a portion of a cell in a sample is analyzed in situ for a first set of analytes (e.g., a panel of mRNA transcripts of interest), e.g., with a super resolution microscope, and a region (e.g., a 1 cm×1 cm tissue slice) comprising the cell is subjected to a spatial assay disclosed herein for a second set of analytes, e.g., all mRNA transcripts for non-targeted transcriptomic analysis.

In some embodiments, a method disclosed herein comprises in situ analysis of a first set of analytes (e.g., nucleic acid analytes of interest) using a plurality of probes. The plurality of probes may comprise primary probes, second probes, and/or even higher order probes, any one or more of which may comprise nucleic acid barcode sequences. The binding of a probe to an analyte or another probe may be direct (e.g., direct hybridization) or indirect (e.g., via a splint or bridging probe). In some embodiments, a method disclosed herein comprises in situ analysis of a nucleic acid analyte (e.g., DNA or mRNA), using one or more probes that directly or indirectly bind to the nucleic acid analyte or complement or product (e.g., a hybridization product, a ligation product, an extension product (e.g., by a DNA or RNA polymerase), a replication product, a transcription/reverse transcription product, and/or an amplification product) thereof. In some embodiments, the method further comprises a spatial analysis disclosed herein, where conditions are provided to allow the capture agents to directly or indirectly capture not only the nucleic acid analyte (e.g., DNA or mRNA) but also at least one of the one or more probes. In some embodiments, the method further comprises generating a first spatially labeled polynucleotide comprising (i) a sequence of the nucleic acid analyte or complement thereof and (ii) a sequence of the spatial barcode or complement thereof of a capture agent disclosed herein, where the spatial barcode corresponds to the position of the capture agent on a substrate (e.g., the first substrate or the second substrate disclosed herein). In some embodiments, the method further comprises generating a second spatially labeled polynucleotide comprising (i) a sequence of one of the one or more probes or complement thereof and (ii) a sequence of the spatial barcode or complement thereof of a capture agent disclosed herein. In some embodiments, the method comprises analyzing both the first spatially labeled polynucleotide (for analyzing the nucleic acid analyte) and the second spatially labeled polynucleotide (for analyzing a probe that directly or indirectly binds the nucleic acid analyte), and analysis of one can be used to validate or complement the other.

In some embodiments, the method comprises capturing the nucleic acid analyte (e.g., DNA or mRNA) and at least one of the one or more probes on different capture agent molecules at the same location on a substrate. In some embodiments, the method comprises capturing the nucleic acid analyte (e.g., DNA or mRNA) and at least one of the one or more probes on different capture agent molecules having the same spatial barcode sequence(s). In some embodiments, the method comprises capturing the nucleic acid analyte (e.g., DNA or mRNA) and at least one of the one or more probes on the same capture agent. In some embodiments, the method comprises generating a spatially labeled polynucleotide comprising (i) a sequence of the nucleic acid analyte or complement thereof, (ii) a sequence of the at least one of the one or more probes or complement thereof, and (iii) a sequence of the spatial barcode or complement thereof of a capture agent disclosed herein.

In some embodiments, the probe(s) captured on the substrate may serve as a spatial reference to provide information regarding one or more other analytes (e.g., endogenous nucleic acid molecules) not targeted by the one or more probes in the in situ analysis.

In some embodiments, an in situ assay module is used as a fiducial marker for the spatial assay module. For example, a probe panel comprising a probe P1 targeting a first analyte mRNA1 of Gene No. 1 may be used to analyze a brain tissue section in situ. mRNA1 is known to be expressed in the brain and this transcript is detected at position X in the tissue sample during in situ imaging. Probe P1 and transcripts including mRNA1 of Gene No. 1 are captured by capture agents on a substrate, tagged by spatial barcodes (including spatial barcode(s) corresponding to position X), and subjected to sequencing. The sequencing reads from Position X include not only those comprising sequences corresponding to P1 and those comprising sequences corresponding to mRNA1 (as a validation of the in situ readout), but also sequencing reads comprising a sequence corresponding to mRNA2. mRNA2 may be a transcript of Gene No. 2 which is different from Gene No. 1, or a variant (e.g., splice variant) of mRNA1 from Gene No. 1. mRNA2 may or may not be targeted by a probe (e.g., probe P1) in the in situ probe panel. Regardless, the sequencing reads comprising a sequence corresponding to mRNA2 and the spatial barcode(s) or complement(s) thereof corresponding to position X indicate that mRNA2 is also present and/or expressed at position X, although mRNA2 is not represented by a probe in the in situ analysis. In this example, a probe (e.g., P1) captured on the substrate serves as a spatial reference at a position (e.g., position X) on a substrate, and analysis of spatially labeled polynucleotides comprising a sequence of the spatial barcode(s) or complement(s) thereof corresponding to the position can provide information of the presence/absence, distribution, location, amount, level, expression, or activity of an analyte (e.g., mRNA2) which is not represented or targeted by a probe in the in situ analysis.

(e) Use of a Multiplexed Sandwich Process

This disclosure also provides methods, compositions, devices, and systems for using a single capture probe-containing substrate to detect analytes from different biological samples (e.g., tissues) on different slides using serial sandwich processes (e.g., using multiple and different first substrates). In this embodiment, multiple first substrates can be used, wherein in situ analysis is performed on each first substrate. In this way, as described herein, analytes from different samples or tissues can be captured serially and demultiplexed by sample-specific index sequences.

In some instances, in situ methods are performed on different biological samples on each first substrate as described throughout this disclosure. Then, the spatial analysis methods are performed. On each first substrate, the methods include generating intermediate agents (e.g., connected probes (e.g., ligation products) or protein derivatives such as an analyte capture agents) in multiple biological samples (e.g. or i.e., a first sample, a second sample, a third sample, etc.). Each intermediate agent (e.g., a ligation product, an analyte capture agent) that is used in a multiplexing sandwiching method as described herein includes a sample index sequence, which is a nucleotide sequence that is associated with a particular sample of origin in the multiplex sandwich methods.

In a multiplexing methods, the sandwiching process is repeated, once for each biological sample. During each sandwiching process, the indexed connected probe or analyte capture agent actively or passively migrates from the sample to the array for capture by a capture probe. Then the sandwich is opened, and the next sample is sandwiched with the array. In some embodiments, the array is washed prior to sandwiching with the next sample. Additional samples or tissues (e.g., at least 1, 2, 3, 4, 5, 6, 7, 8, 9, 10, or more additional samples) can then be sandwiched with the array or slide having a plurality of capture probes, wherein connected probes (e.g., ligation products) or analyte capture agents from the additional samples or tissues can be transferred to the array in a similar manner. Because each sample includes a unique sample index, the sample of origin for each connected probe (e.g., a ligation product) or analyte capture agent that is captured on the array can be identified. In addition, the location of the connected probe (e.g., a ligation product) can be identified. In some embodiments, the location of the analyte capture agent can be identified.

In some instances, the sample index is about 5 nucleotides to about 50 nucleotides long (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotides long. In some embodiments, the sample index is about 5-15 nucleotides long. In some embodiments, the sample index is about 10-12 nucleotides long. Both synthetic and/or naturally-occurring nucleotides can be used to generate a sample index sequence. It is appreciated that any sequence can be designed so long as it is unique among other sample index sequences and optionally that it can be distinguished from any sequence in the genome of the sample.

A sample index sequence can be located anywhere on the connected probe (e.g., a ligation product) so long as it does not affect (1) hybridization of the probes to the analyte, (2) ligation of the probes to generate the connected probe (e.g., a ligation product), and (3) hybridization of the capture probe binding domain to the capture probe on an array.

EXAMPLES

Example 1

This example illustrates a method of analyzing a biological sample by generating sequence and spatial information of analyte nucleic acid molecules using in situ analysis using fluorescence microscopy as readout, followed by spatial array-based analysis using next-generation sequencing of molecules captured on the array, for the same sample as for the in situ analysis.

Fresh frozen mouse brain sections were placed on a glass slide. The sections were fixed with formaldehyde then permeabilized with HCl.

Upon tissue fixation, mRNAs were targeted by barcoded padlock probes directed to three analyte genes, DAPI positive control, and negative control, padlock probes were ligated using a ligase, and a rolling circle amplification (RCA) protocol was performed. Probe hybridization occurred at 37 degrees C. overnight with a probe concentration of 10 nM. Ligation occurred at 37 degrees C. for two hours. RCA primer hybridization occurred at 30 degrees C. for 30 minutes and RCA occurred at 30 degrees C. overnight. Fluorescently labeled detection probes were hybridized to RCA products and analyzed by highly multiplexed in situ imaging approaches followed by sequencing by hybridization with microscopy readouts. Results from the microscopy readouts of the in situ analysis workflow are presented in FIGS. 8A-10E.

In order to preserve the endogenous transcriptome during the in situ protocol described above, ribonuclease (RNase) inhibitors were used to protect from RNase A and/or RNase H degradation of RNA in DNA-RNA hybrids during the in situ analysis workflow.

After the in situ analysis workflow was performed as described above, tissue samples on slides were stored at 4 degrees C. for approximately three weeks. Subsequently, the tissue samples on slides were brought to room temperature for the following spatial array-based workflow.

Figure 7A:
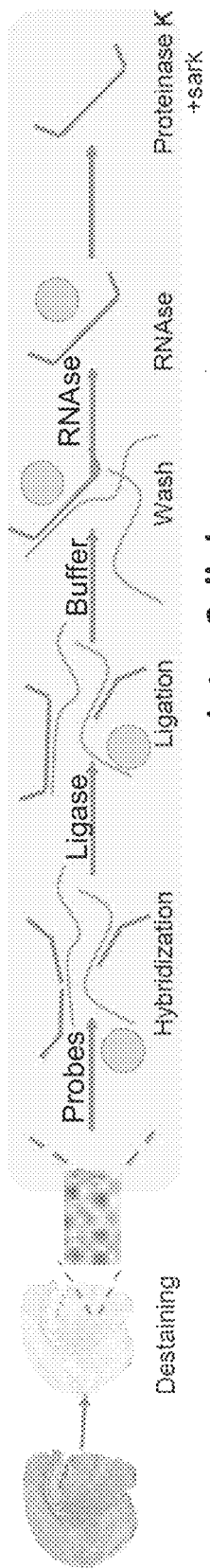
FIG. 7A shows an exemplary workflow for using ligated probes to capture intracellular analytes.

After temperature equilibration, tissue samples were incubated with a probe hybridization mix comprising RTL probes directed to the entire mouse transcriptome at 50° C. overnight. During this incubation, individual probes (e.g., a first probe, a second probe) of probe pairs hybridized to adjacent sequences of analyte mRNA molecules in the mouse brain sections on the slide. The following day, the tissue samples were washed to remove un-hybridized probes and a probe ligation mix was introduced to the slide. During a 60 minute incubation at 37° C., the RTL probes were then ligated together, thereby creating a connected probe (e.g., a ligation product) (FIG. 7A). The connected probe (e.g., a ligation product) included a capture probe binding domain. The probes were designed to hybridize to each transcript in the mouse transcriptome.

Figure 7B:
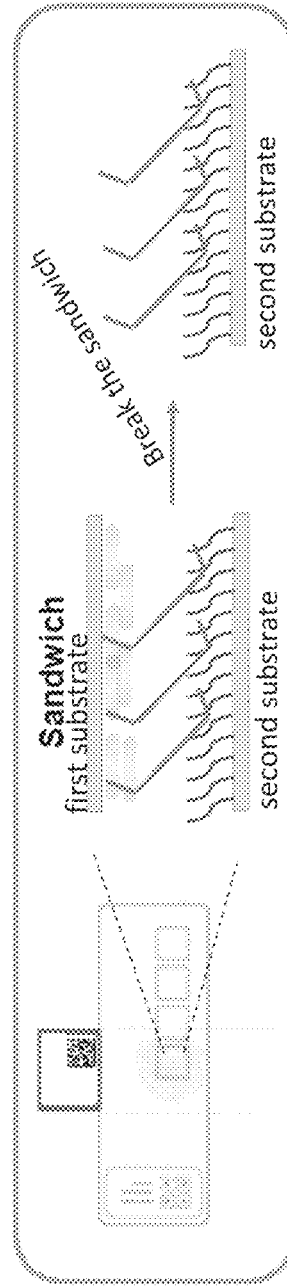
FIG. 7B shows an exemplary schematic illustrating the tissue sample sandwiched between a substrate and a spatially-barcoded capture probe array, wherein the ligated probes are transferred to the spatially-barcoded capture probe array.

After ligation of the RTL probes, the connected probes were released from the tissue using a sandwich process with RNase+Proteinase K in the reagent medium. The tissue mounted standard slides were aligned with a second substrate (e.g., barcoded array slide comprising an array of spatially barcoded capture probes), and permeabilized in the sandwich configuration as described herein (see, e.g., FIG. 7B). Following permeabilization, the capture probes were extended, sequencing libraries were prepared and sequenced, and the results were analyzed computationally. Results from these analyses are presented in FIGS. 12A-15B as heatmaps based on intensity of expression of either an analyte gene or expression of the entire mouse transcriptome.

Data generated by the workflows described above, e.g. or i.e., an in situ analysis workflow followed by a spatial analysis workflow performed on the same sample, were compared to data generated by a spatial analysis workflow alone which were treated as control data, and performance of the combined workflow was evaluated relative to the spatial analysis workflow alone. The comparisons of the performance of the combined workflow relative to the spatial analysis workflow alone are presented in Tables 1-3 (UMI=unique molecular identifier; nt=nucleotide):

TABLE 1

| | Valid Barcodes | Valid UMIs | Fraction of raw reads on analyte/ unambiguously mapped | Fraction reads unmapped | Fraction of chimeric reads under tissue | Fraction reads with primer/ homopolymer sequence | Reads with full polyA sequence | Fraction reads usable |
|---|---|---|---|---|---|---|---|---|
| Spatial assay control | 98.9% | 100% | 92.5% | 1.1% | 1.1% | 0.1% | 0.0% | 84.2% |
| In situ assay followed by spatial assay | 98.6% | 100% | 93.3% | 1.5% | 1.5% | 0.1% | 0.0% | 89.7% |

TABLE 2

| | Fraction UMI counts for genes <500 nt | Fraction UMI counts for genes >1500 nt | Fraction UMI counts for genes 1000-1500 nt | Fraction UMI counts for genes 500-1000 nt | Reads Mapped Confidently to Exonic Regions | Reads Mapped Confidently to Transcriptome | Reads Mapped to Genome |
|---|---|---|---|---|---|---|---|
| Spatial assay control | 2.7% | 47.1% | 14.7% | 35.6% | 98.2% | 98.2% | 98.9% |
| In situ assay followed by spatial assay | 2.6% | 47.0% | 15.3% | 35.2% | 98.3% | 98.3% | 98.5% |

TABLE 3

| | Fraction of Spots Under Tissue | Fraction Reads in Spots Under Tissue | Median panel genes detected at 30K panel reads per spot | Median panel genes detected at 30K raw reads per spot | Median panel UMI counts at 30K panel reads per spot | Median panel UMI counts at 30K raw reads per spot | Panel cDNA PCR Duplication (30K panel reads per spot) | Panel cDNA PCR Duplication (30K raw reads per spot) |
|---|---|---|---|---|---|---|---|---|
| Spatial assay control | 49.1% | 92.4% | 6,873 | 6,487 | 22,761 | 19,869 | 22.0% | 19.2% |
| In situ assay followed by spatial assay | 49.9% | 97.8% | 6,104 | 5,882 | 19,636 | 18,098 | 25.9% | 23.8% |

The spatial assay control data and in situ assay followed by spatial assay data presented in Tables 1-3 demonstrate that a spatial analysis workflow can be performed on a tissue sample that has undergone an in situ analysis workflow with similar results and performance. Given the conditions that the tissue sample experiences during the in situ analysis workflow (e.g. extended incubations at elevated temperatures, extended storage times, exposure to a variety of buffers and reagents, multiple imaging steps), these are unexpected results. The comparative data presented in Tables 1-3 indicate that it is possible to sequentially analyze the same tissue sample with multiple methods disclosed herein, e.g. an in situ analysis workflow followed by a spatial analysis workflow, and acquire spatial analysis data similar to as if the sample had only undergone the spatial analysis workflow.

Figure 8C:
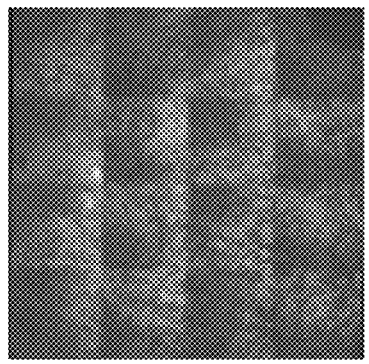
FIG. 8C shows fluorescent microscopy results from an in situ analysis workflow of a first mouse brain cortex tissue section displaying Cy3 detection of Tmem131 (NEG) transmembrane protein 131 (Neg).
Figure 8B:
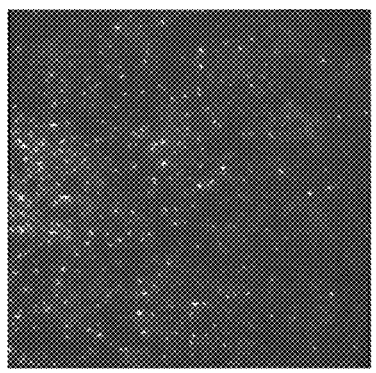
FIG. 8B shows fluorescent microscopy results from an in situ analysis workflow of a first mouse brain cortex tissue section displaying AF488 detection of proteolipid protein 1 (Plp1).
Figure 8E:
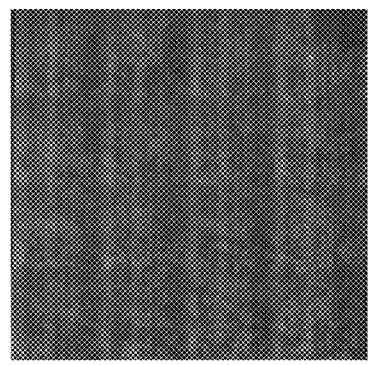
FIG. 8E shows fluorescent microscopy results from an in situ analysis workflow of a first mouse brain cortex tissue section displaying AF750 detection of prospero homeobox 1 (Prox1).
Figure 8A:
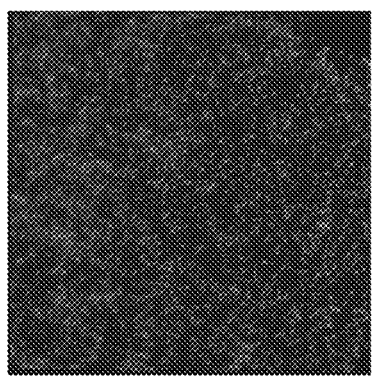
FIG. 8A shows fluorescent microscopy results from an in situ analysis workflow of a first mouse brain cortex tissue section displaying DAPI (i.e., nuclei) detection of the tissue sample.
Figure 8D:
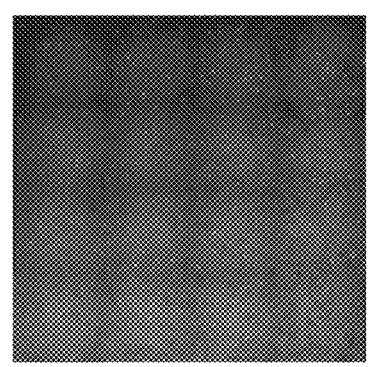
FIG. 8D shows fluorescent microscopy results from an in situ analysis workflow of a first mouse brain cortex tissue section displaying Cy5 detection of SATB homeobox 2 (Satb2).

Additional results from the sequential workflows represented in this example are shown in FIGS. 8A-10E and FIGS. 12A-15B. FIGS. 8A-8E show fluorescent images from the in situ analysis workflow of this example, performed on a first mouse brain cortex tissue section. FIG. 8A shows DAPI detection of the tissue sample, e.g. or i.e., detection of nuclei within cells of the tissue sample; FIG. 8B shows AF488 detection of proteolipid protein 1 (Plp1) in the tissue sample; FIG. 8C shows Cy3 detection of Tmem131 (NEG) transmembrane protein 131 (Neg) in the sample; FIG. 8D show Cy5 detection of SATB homeobox 2 (Satb2) in the tissue sample; and FIG. 8E shows AF750 detection of prospero homeobox 1 (Prox1) in the tissue sample.

Figure 9C:
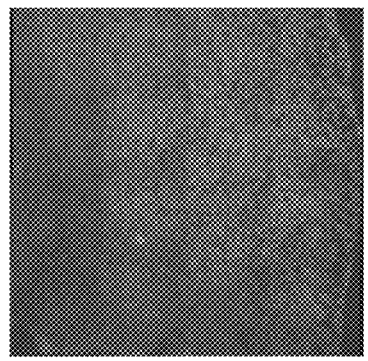
FIG. 9C shows fluorescent microscopy results from an in situ analysis workflow of a second mouse brain cortex tissue section displaying Cy3 detection of Neg.
Figure 9B:
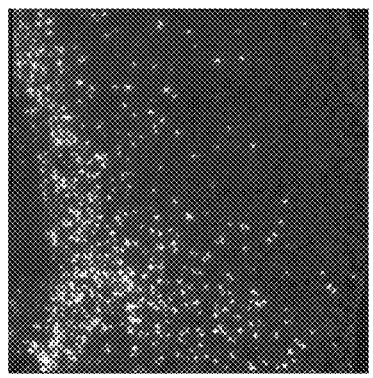
FIG. 9B shows fluorescent microscopy results from an in situ analysis workflow of a second mouse brain cortex tissue section displaying AF488 detection of Plp1.
Figure 9E:
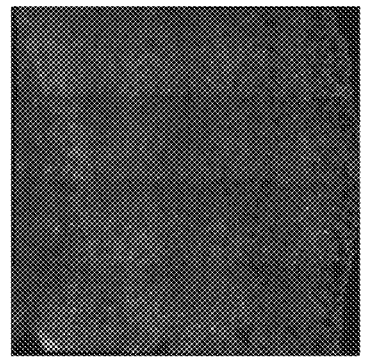
FIG. 9E shows fluorescent microscopy results from an in situ analysis workflow of a second mouse brain cortex tissue section displaying AF750 detection of Prox1.
Figure 9A:
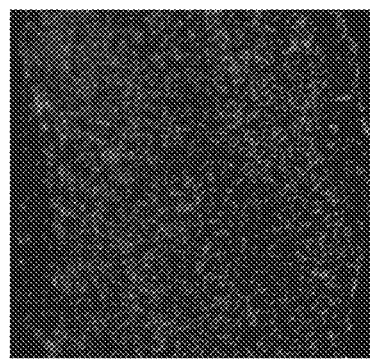
FIG. 9A shows fluorescent microscopy results from an in situ analysis workflow of a second mouse brain cortex tissue section displaying DAPI (i.e., nuclei) detection of the tissue sample.
Figure 9D:
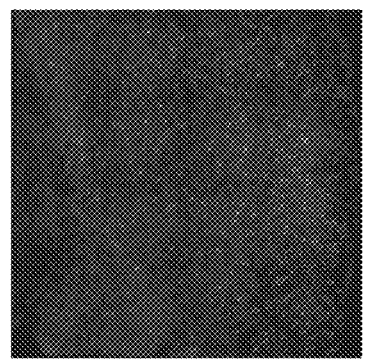
FIG. 9D shows fluorescent microscopy results from an in situ analysis workflow of a second mouse brain cortex tissue section displaying Cy5 detection of Satb2.

FIGS. 9A-9E show additional fluorescent images from the in situ analysis workflow of this example, performed on a second mouse brain cortex tissue section. FIG. 9A shows DAPI detection of the tissue sample, e.g. or i.e., detection of nuclei within cells of the tissue sample; FIG. 9B shows AF488 detection of Plp1 in the tissue sample; FIG. 9C shows Cy3 detection of Neg in the sample; FIG. 9D shows Cy5 detection of Satb2 in the tissue sample; and FIG. 9E shows AF750 detection of Prox1 in the tissue sample.

Figure 10C:
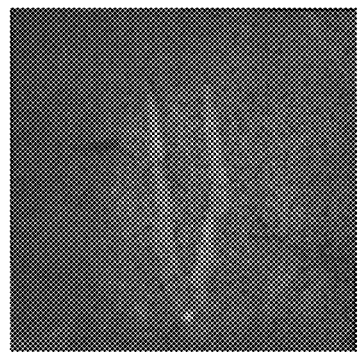
FIG. 10C shows fluorescent microscopy results from an in situ analysis workflow of a mouse brain dentate gyrus tissue section displaying Cy3 detection of Neg.
Figure 10B:
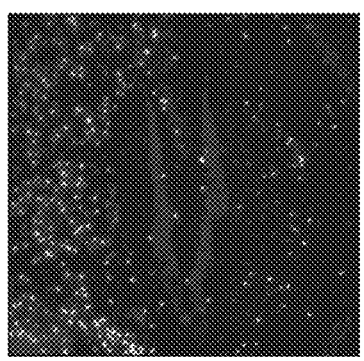
FIG. 10B shows fluorescent microscopy results from an in situ analysis workflow of a mouse brain dentate gyrus tissue section displaying AF488 detection of Plp1.
Figure 10E:
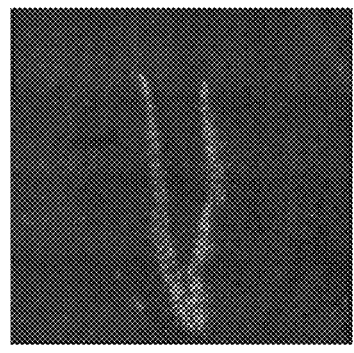
FIG. 10E shows fluorescent microscopy results from an in situ analysis workflow of a mouse brain dentate gyrus tissue section displaying AF750 detection of Prox1.
Figure 10A:
FIG. 10A shows fluorescent microscopy results from an in situ analysis workflow of a mouse brain cortex tissue section displaying DAPI (i.e., nuclei) detection of the tissue sample.
Figure 10D:
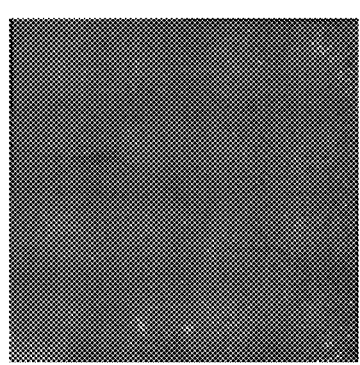
FIG. 10D shows fluorescent microscopy results from an in situ analysis workflow of a mouse brain dentate gyrus tissue section displaying Cy5 detection of Satb2.
Figure 11A:
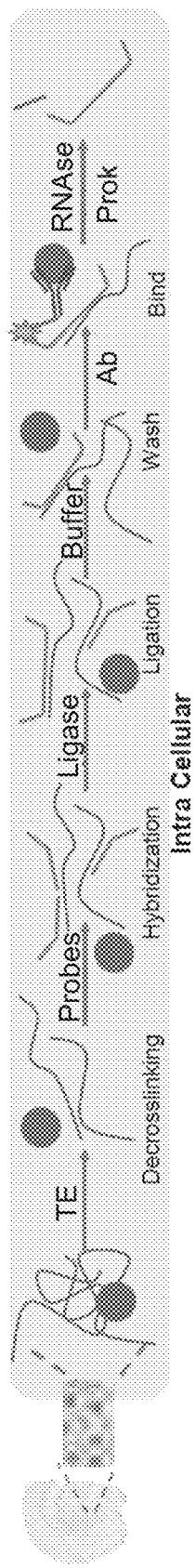
FIG. 11A shows an exemplary workflow for using ligated probes and analyte capture agents to capture intracellular analytes.
Figure 11B:
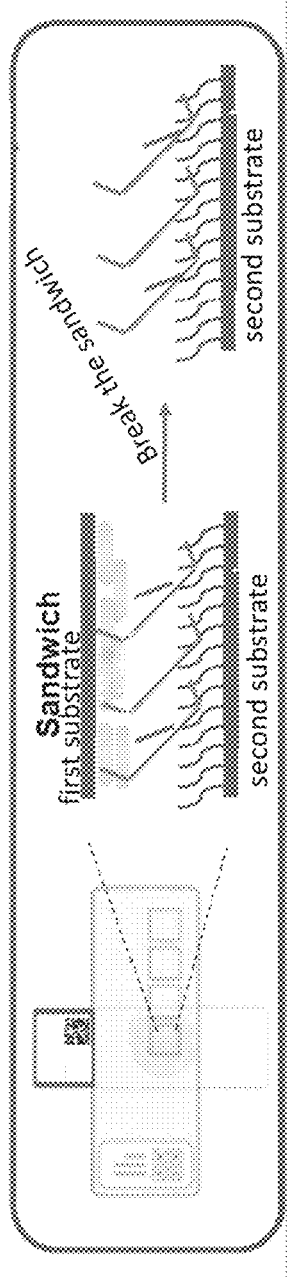
FIG. 11B shows an exemplary schematic illustrating the tissue sample sandwiched between a substrate and a spatially-barcoded capture probe array, wherein the ligated probes and capture agent barcode domains are transferred to the spatially-barcoded capture probe array.

FIGS. 10A-10E show additional fluorescent images from the in situ analysis workflow of this example, performed on a mouse brain dentate gyrus tissue section. FIG. shows DAPI detection of the tissue sample, e.g. or i.e., detection of nuclei within cells of the tissue sample; FIG. 10B shows AF488 detection of Plp1 in the tissue sample; FIG. 10C shows Cy3 detection of Neg in the sample; FIG. 10D shows Cy5 detection of Satb2 in the sample; and FIG. 10E shows AF750 detection of Prox1 in the tissue sample.

Figures 12A, 12B:
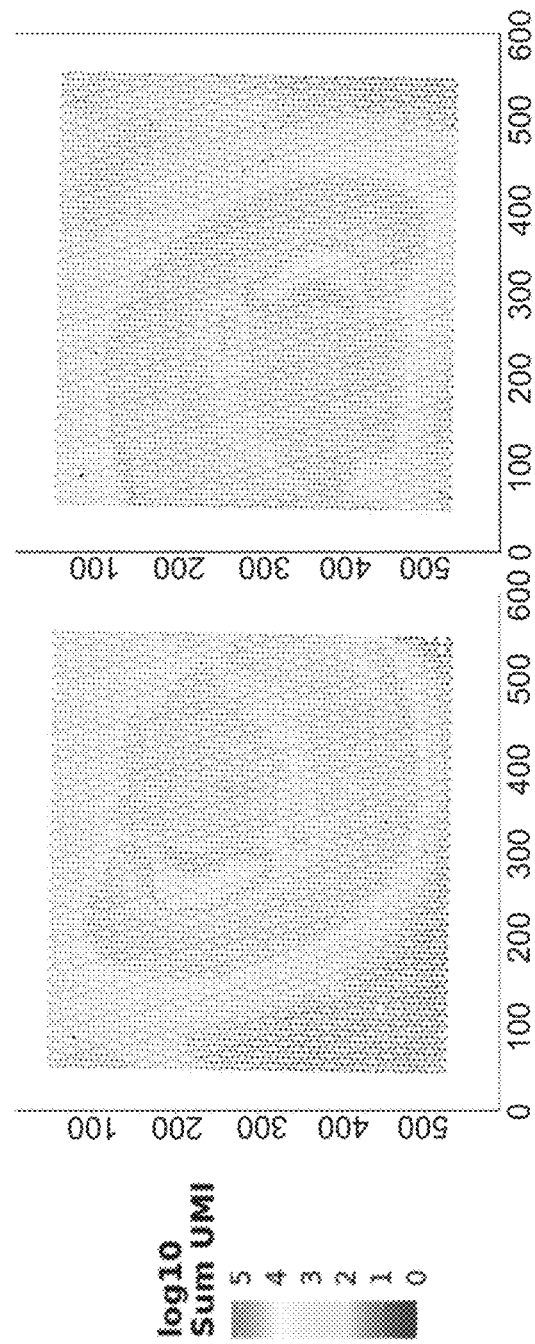
FIG. 12A shows spatial data of the entire mouse transcriptome for a mouse brain tissue section.
FIG. 12B shows spatial data of the entire mouse transcriptome for a second replicate of the same mouse brain tissue section as shown in FIG. 12A.

FIGS. 12A-13B show spatial data for tissue samples that underwent only the spatial analysis workflow, represented as heatmaps based on intensity of expression of an analyte gene or intensity of expression of the entire mouse transcriptome. FIGS. 14A-15B show spatial data for tissue samples that underwent the in situ analysis workflow followed by the spatial analysis workflow, represented as heatmaps based on intensity of expression of an analyte gene or expression of the entire mouse transcriptome. FIG. 12A shows spatial data of the entire mouse transcriptome for a mouse brain tissue section and FIG. 12B shows spatial data of the entire mouse transcriptome for a second replicate of the same mouse brain tissue section as FIG. 12A. FIG. 13A shows spatial data for expression of a single analyte gene for a mouse brain tissue section and FIG. 13B shows spatial data for expression of a single analyte gene for a second replicate of the same mouse brain tissue section as FIG. 13A.

FIG. 14A shows spatial data of the entire mouse transcriptome for the same mouse brain cortex tissue section as the fluorescent in situ analysis data presented in FIGS. 9A-9E. FIG. 14B shows spatial data of the entire mouse transcriptome for the same mouse brain cortex tissue section as the fluorescent in situ analysis data presented in FIGS. 8A-8E. The results shown in FIGS. 14A and 14B indicate that, surprisingly, whole transcriptome spatial data can successfully be obtained for a sample that has previously undergone the in situ analysis workflow, and that the data are similar in quality to the data for a tissue sample that has only undergone the spatial analysis workflow, e.g. the data shown in FIGS. 12A and 12B.

FIG. 15A shows spatial data of the intensity of expression of the analyte gene Hpca for the same mouse brain cortex tissue section as the fluorescent in situ analysis data presented in FIGS. 9A-9E. FIG. 15B shows spatial data of the intensity of expression of the analyte gene Hpca for the same mouse brain cortex tissue section as the fluorescent in situ analysis data presented in FIGS. 8A-8E. The results shown in FIGS. 15A and 15B indicate that, surprisingly, spatial data for a analyte gene of interest can successfully be obtained for a sample that has previously undergone the in situ analysis workflow, and that the data are similar in quality to the data for a tissue sample that has only undergone the spatial analysis workflow, e.g. the data shown in FIGS. 13A and 13B.

The spatial data of the entire mouse transcriptome presented in FIG. 14A and the spatial data of the intensity of expression of the analyte gene Hpca presented in FIG. 15A correspond to the fluorescent images from the in situ analysis workflow performed on the mouse brain dentate gyrus tissue section presented in FIGS. 10A-10E.

Taken together, FIGS. 8A-10E and FIGS. 12A-15B indicate, surprisingly, that it is possible to sequentially analyze the same tissue sample with multiple methods disclosed herein, e.g. or i.e. an in situ analysis workflow followed by a spatial analysis workflow, and generate reproducible informative data that is similar in quality to data produced for a tissue sample analyzed by the spatial analysis workflow alone.

Example 2

This example illustrates a method of analyzing a biological sample by generating sequence and spatial information of analyte nucleic acid molecules. In situ analysis using fluorescence microscopy as readout was followed by spatial array-based analysis using next-generation sequencing of molecules captured on the array, on the same (not-serial) section.

Figure 22B:
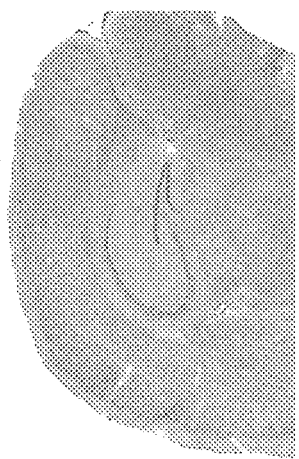
FIG. 22B shows H&E staining of the fresh frozen mouse brain section after the in situ analysis steps.
Figure 22D:
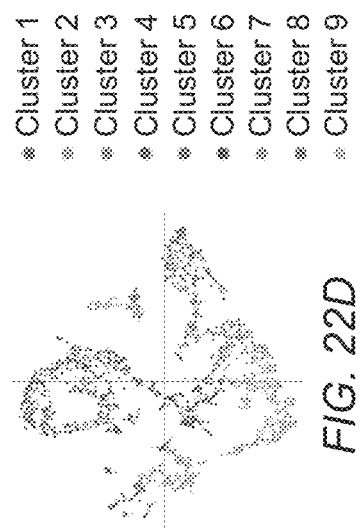
FIG. 22D shows a t-distributed stochastic neighbor (t-SNE) plot of results from a spatial analysis workflow performed on the same fresh frozen mouse brain section shown in FIGS. 22A and 22B.
Figure 22A:
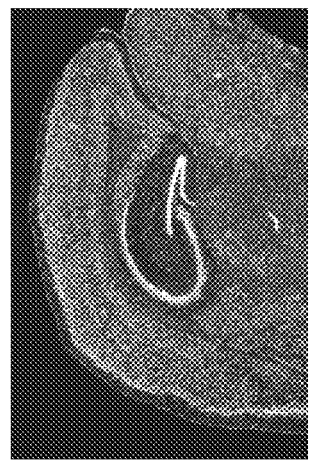
FIG. 22A shows a representative fluorescent microscopy image of a fresh frozen mouse brain section generated by the in situ analysis workflow using barcoded padlock probes directed to 200 analyte genes.
Figure 22C:
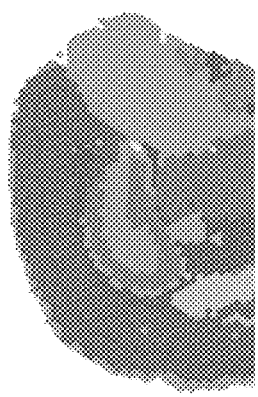
FIG. 22C shows a spatial plot of results from a spatial analysis workflow performed on the same fresh frozen mouse brain section shown in FIGS. 22A and 22B.
Figure 24:
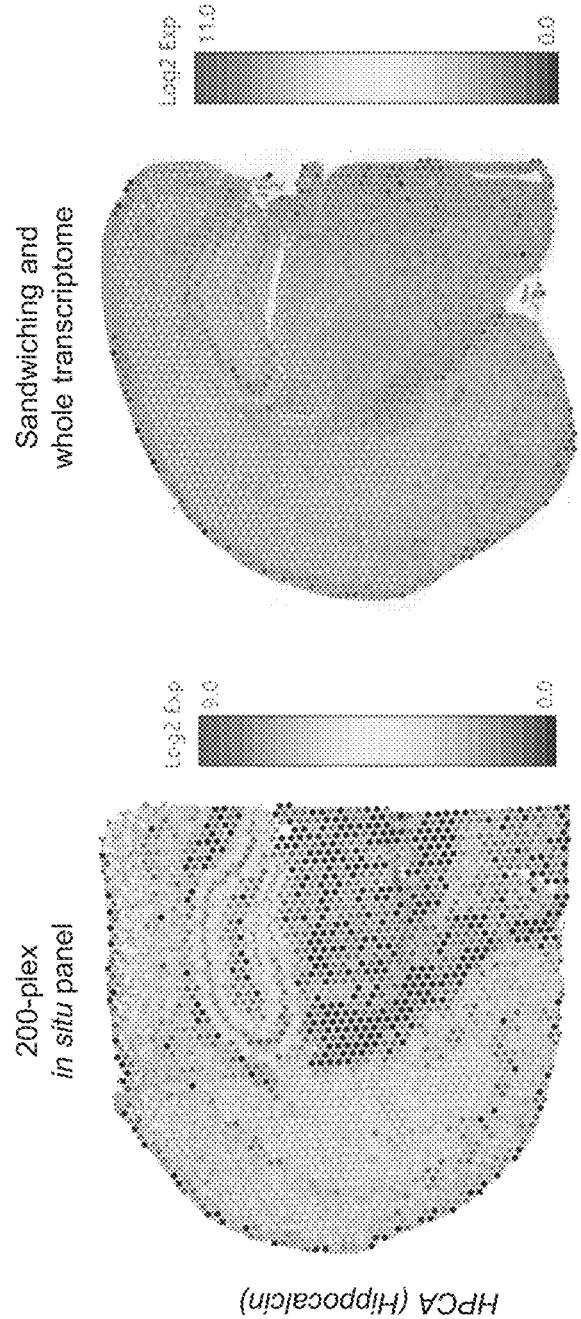
FIG. 24 shows example results for the HPCA gene in a fresh frozen mouse brain section by the in situ analysis workflow targeting 200 analyte genes (left) and the whole-transcriptome spatial analysis workflow performed on the same sample (right).
Figure 25:
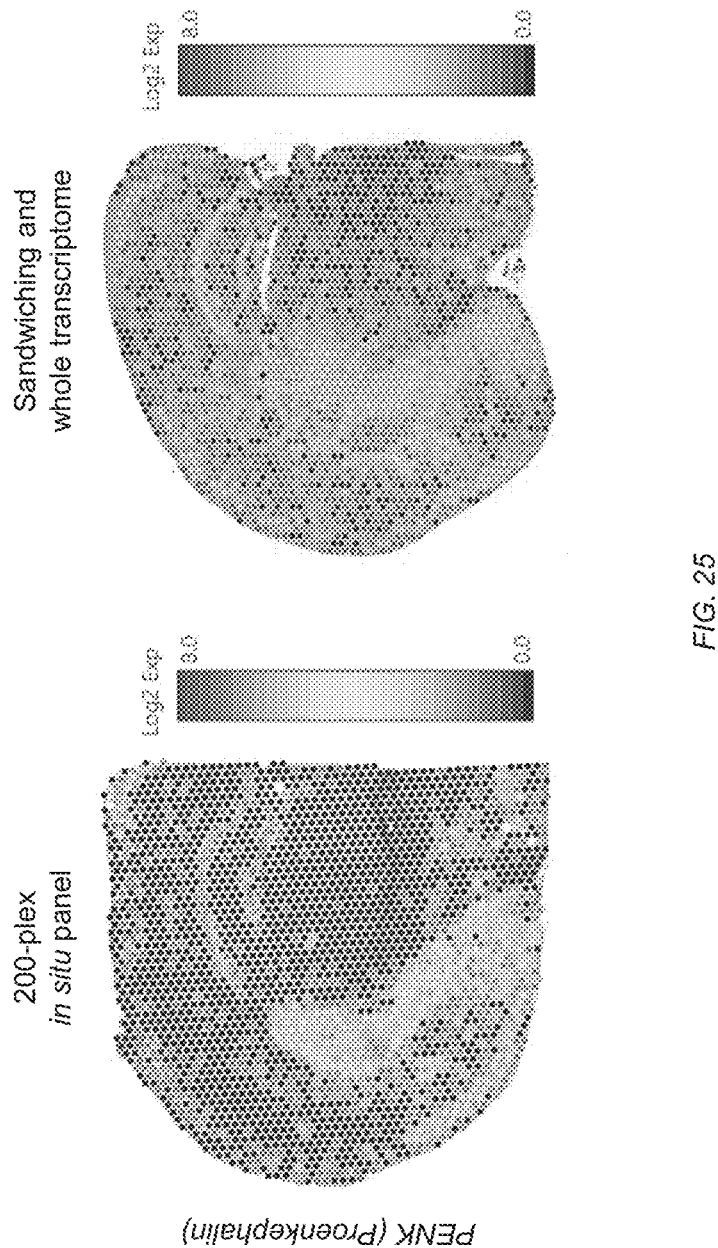
FIG. 25 shows example results for the PENK gene in a fresh frozen mouse brain section by the in situ analysis workflow targeting 200 analyte genes (left) and the whole-transcriptome spatial analysis workflow performed on the same sample (right).

Fresh frozen mouse brain sections were placed on a glass slide. Fresh frozen sections were fixed with formaldehyde then permeabilized with HCl.

mRNAs were targeted by barcoded padlock probes directed to 200 analyte genes and negative control probes. Padlock probe hybridization occurred at 50° C. overnight with a probe concentration of 10 nM. After stringency washing to remove un-hybridized probes, probes were ligated at 37° C. for two hours. During this step, a rolling circle amplification (RCA) primer was also annealed. RCA enzyme was incubated for 1 hour at 4° C. followed by 2 hours at 37° C. After washing, background fluorescence was then quenched, and sections were placed into an imaging cassette and loaded onto the decoding instrument. On the instrument, fluorescently labeled detection probes were hybridized to RCA products and then stripped for a total of 12 cycles according to highly multiplexed in situ imaging approaches. A representative microscopy image of the in situ analysis workflow is presented in FIG. 22A. FIG. 22A shows the fluorescent microscopy readout of the fresh frozen mouse brain section after hybridization of the fluorescently labeled detection probes. Exemplary summary statistics of the data include: 59,790 cells detected by the in situ assay; gene tissue density score: 0.416; and median transcripts detected per non-empty cell: 155. FIG. 22B shows H&E staining of the brain section after the in situ analysis steps.

In order to preserve the endogenous transcriptome during the in situ protocol described above, ribonuclease (RNase) inhibitors were used during the hybridization and ligation steps to protect from RNase degradation of RNA in DNA-RNA hybrids during the in situ analysis workflow.

After the in situ analysis workflow was performed as described above, tissue sections on slides were stored in PBS at 4° C. for approximately two weeks. Subsequently, the following spatial array-based workflow was performed. The slides were removed from the in situ cassette, stained with H&E (FIG. 22B) and photographed. The tissue sections were then destained with 0.1N HCl and incubated with a probe hybridization mix comprising RTL probes directed to the entire mouse transcriptome (about 18,000 genes) at 50° C. overnight. During this incubation, probe pairs hybridized to adjacent sequences of analyte mRNA molecules in the mouse brain sections. The following day, the tissue sections were washed to remove un-hybridized probes. During a 60 minute incubation at 37° C., the RTL probes were then ligated together, thereby creating a connected probe (e.g., a ligation product) (FIG. 7A).

The slides with tissue sections and barcoded array capture slides were loaded into the sandwich apparatus (e.g., a sample handling apparatus disclosed herein, e.g., a sample handling apparatus 1700). Ligated RTL probes were released from the tissue with RNase+Proteinase K in buffer and captured by the barcoded array capture slide for 30 minutes within the sandwich apparatus (see, e.g., FIG. 7B). After capture, probes were extended, amplified, and libraries were prepared for sequencing. Sequencing results demonstrated 2683 spots under tissue, a mean of 51735 reads per spot, a median of 2849 genes per spot, 138,805,290 reads total, 99.2% valid barcodes, 100% valid UMIs, and a sequencing saturation of 88.6%, indicating high quality sequencing data. Results were analyzed computationally to produce a spatial plot (FIG. 22C) and a t-distributed stochastic neighbor (t-SNE) plot (FIG. 22D). Example results for two of the 200 analyte genes, HPCA and PENK, are presented in FIGS. 24 and 25, respectively, as heatmaps based on intensity of expression of each analyte gene.

Results from the 200-plex in situ analysis, and subsequent spatial analysis for four exemplary target analyte genes (Cyp26b1, Prdm8, My14, and Shisa6) are presented in FIGS. 23A-23D, respectively.

The data presented in FIGS. 23A-23D and FIGS. 24-25 demonstrate that a spatial analysis workflow can be performed on a tissue sample that has undergone an in situ analysis workflow targeting a panel of at least 200 or more target analyte genes with similar results and performance. Given the conditions that the tissue sample experiences during the in situ analysis workflow (e.g. extended incubations at elevated temperatures, extended storage times, exposure to a variety of buffers and reagents, multiple imaging steps), these are unexpected results. The comparative data presented in FIGS. 23A-23D and FIGS. 24-25 indicate that it is possible to sequentially analyze the same tissue sample with multiple methods disclosed herein, e.g. an in situ analysis workflow targeting a panel of at least 200 or more target analyte genes followed by a spatial analysis workflow, and acquire spatial analysis data similar to as if the sample had only undergone the spatial analysis workflow.

Example 3

Figure 26:
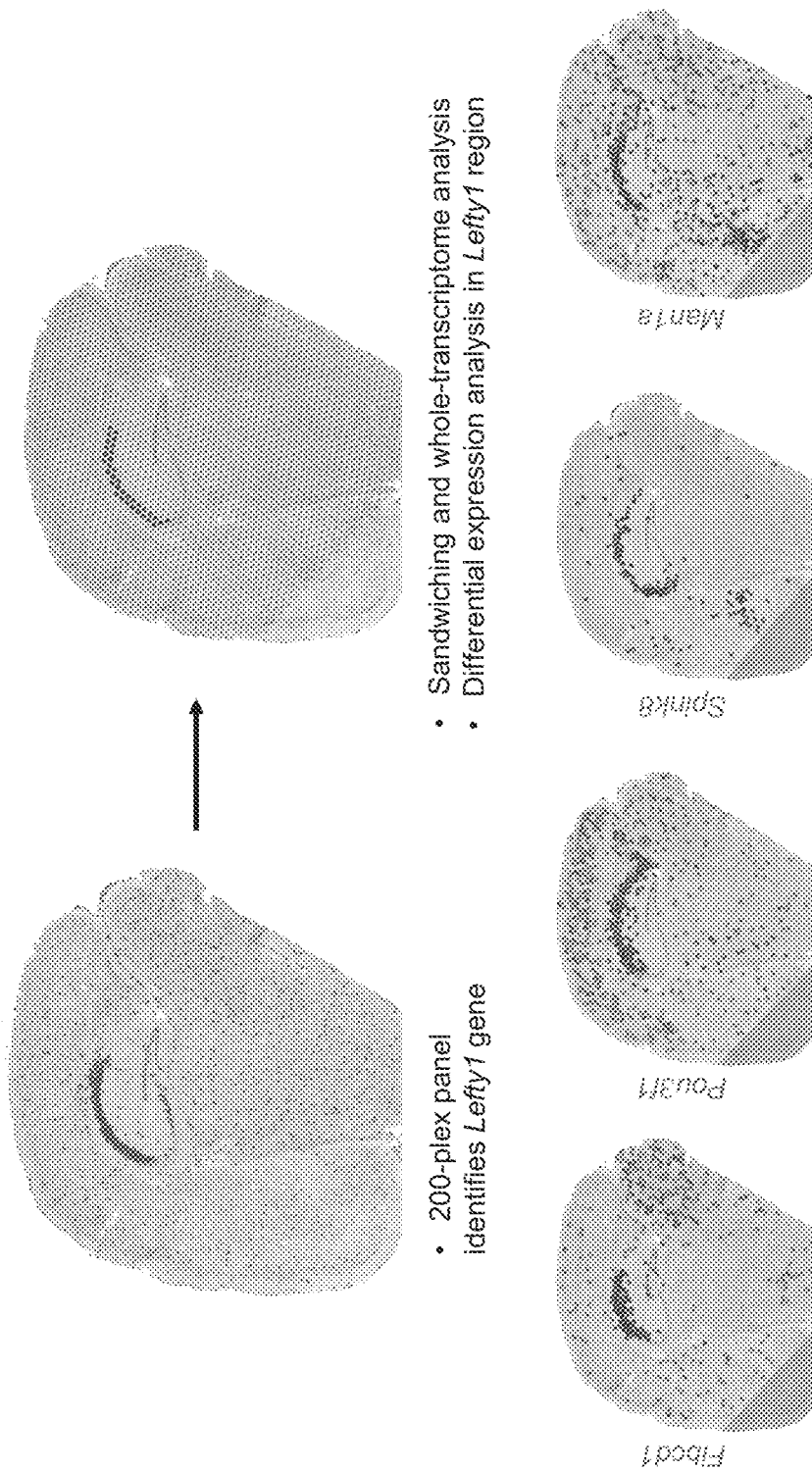
FIG. 26 shows the spatial distribution of expression of Fibcd1, Pou3f1, Spink8, and Man1 overlapping with the spatial distribution of expression of Lefty1, as determined by the in situ analysis workflow targeting a panel of 200 target analyte genes followed by the spatial analysis workflow performed on the same section.

This example illustrates an additional use of the combined method e.g. an in situ analysis workflow targeting a panel of at least 200 or more target analyte genes followed by a spatial analysis workflow. As shown in FIG. 26, the gene Lefty1 was identified as a spatially restricted gene in fresh frozen mouse brain section by the in situ analysis workflow described in Example 2 targeting a panel of at least 200 or more target analyte genes. In order to determine additional genes that exhibit a syn-expression pattern with Lefty1, the spatial analysis workflow was performed on the same section to obtain whole-transcriptome spatial gene expression data. Regional differential expression analysis was performed computationally in the regions of the section expressing Lefty1. From this analysis, additional differentially expressed genes were identified. For example, the spatial distribution of expression of Fibcd1, Pou3f1, Spink8, and Man1 overlap with the spatial distribution of expression of Lefty1, shown in FIG. 26. Data for additional differentially expressed genes in the Lefty1 synexpression group are shown in Table 4.

TABLE 4

| Gene | Log2 FC | p-value |
|---|---|---|
| Fibcd1 | 4.57 | $1.10 \times 10^{-33}$ |
| Spink8 | 4.42 | $3.44 \times 10^{-29}$ |
| Thsd4 | 3.58 | $1.01 \times 10^{-14}$ |
| Man1a | 2.85 | $2.66 \times 10^{-13}$ |
| Pou3f1 | 2.88 | $5.71 \times 10^{-12}$ |
| Wipf3 | 2.72 | $8.42 \times 10^{-12}$ |
| Hpca | 2.60 | $1.32 \times 10^{-11}$ |
| Neurod6 | 2.66 | $1.40 \times 10^{-11}$ |
| Sstr4 | 2.61 | $3.85 \times 10^{-11}$ |
| Crym | 2.63 | $9.46 \times 10^{-11}$ |

Taken together, the data represented in FIGS. 23A-23D, FIGS. 24-26, and Table 4 indicate, surprisingly, that it is possible to sequentially analyze the same tissue sample with multiple methods disclosed herein, e.g. an in situ analysis workflow targeting a panel of at least 200 or more target analyte genes followed by a spatial analysis workflow, and generate reproducible informative data that is similar in quality to data produced for a tissue sample analyzed by the spatial analysis workflow alone.

What is claimed is:

1. A method for analyzing nucleic acids in a tissue sample placed on a first substrate, the method comprising:
    (a) permeabilizing the tissue sample on the first substrate,
    (b) contacting the permeabilized tissue sample on the first substrate with one or more nucleic acid probes that directly or indirectly hybridize to a set of first nucleic acids or their complements thereof in the tissue sample;
    (c) detecting the one or more nucleic acid probes at a spatial location of the permeabilized tissue sample on the first substrate;
    (d) hybridizing a first probe and a second probe to a second nucleic acid in the permeabilized tissue sample on the first substrate, wherein the first probe comprises a sequence that is substantially complementary to a first sequence of the second nucleic acid, the second probe comprises a sequence that is substantially complementary to a second sequence of the second nucleic acid, and wherein the second probe comprises a capture probe binding domain that comprises a sequence complementary to a capture domain on an array;

(e) coupling the first probe and the second probe located on the second nucleic acid, thereby generating a connected probe;

(f) after step (e), mounting the first substrate on a first member of a support device, the first member configured to retain the first substrate;

(g) mounting a second substrate comprising the array on a second member of the support device, the second member configured to retain the second substrate, the array comprising a plurality of capture probes, wherein a capture probe of the plurality of capture probes comprises (i) a spatial barcode and (ii) the capture domain;

(h) after steps (f) and (g), applying a reagent medium to the first substrate and/or the second substrate;

(i) moving the first member or the second member along an axis orthogonal to the second member or the first member by operating an alignment mechanism of the support device such that the connected probe located on the second nucleic acid of the permeabilized tissue sample on the first substrate is aligned with the array on the second substrate, wherein at least portion of the permeabilized tissue sample on the first substrate and at least portion of the array on the second substrate contact the reagent medium, and the first substrate and the second substrate are separated by a distance less than 50 micrometers;

(j) after step (i), releasing the connected probe located on the second nucleic acid from the first substrate and migrating the connected probe from the permeabilized tissue sample on the first substrate to the array on the second substrate; and (k) hybridizing the connected probe to the capture domain of the capture probe of the array on the second substrate.

2. The method of claim 1, wherein the first sequence and the second sequence of the second nucleic acid are adjacent to one another.

3. The method of claim 1, wherein the first sequence and the second sequence of the second nucleic acid are at least 1, 2, 3, 4, 5, 6, 7, 8, 9, 10, or more than 10 nucleotides away from one another.

4. The method of claim 3, further comprising generating an extended first probe using a polymerase, wherein the extended first probe comprises a sequence complementary to a sequence between the first sequence and the second sequence of the second nucleic acid.

5. The method of claim 3, further comprising generating an extended second probe using a polymerase, wherein the extended second probe comprises a sequence complementary to a sequence between the first sequence and the second sequence of the second nucleic acid.

6. The method of claim 1, wherein said coupling the first probe and the second probe comprises ligating the first probe and the second probe via a ligase.

7. The method of claim 6, wherein the ligase is selected from a PBCV-1 DNA ligase, *Chlorella* virus DNA ligase, a single stranded DNA ligase, and a T4 DNA ligase.

8. The method of claim 1, wherein one or more of steps (a) to (g) comprise a ribonuclease (RNase) inhibitor.

9. The method of claim 1, wherein the reagent medium comprises a protease selected from trypsin, pepsin, elastase, and proteinase K.

10. The method of claim 1, further comprising determining (i) all or a part of the sequence of the connected probe or a complement thereof, and (ii) the sequence of the spatial barcode or a complement thereof, and determining the location of the second nucleic acid in the permeabilized tissue sample on the first substrate based on the all or a part of the sequence of the connected probe or the complement thereof, and the sequence of the spatial barcode or the complement thereof.

11. The method of claim 1, wherein the set of first nucleic acids comprises an RNA analyte.

12. The method of claim 1, wherein the set of first nucleic acids comprises a DNA analyte.

13. The method of claim 1, wherein the second nucleic acid is RNA.

14. The method of claim 13, wherein the reagent medium comprises an agent for releasing the connected probe, wherein the agent for releasing the connected probe is an RNase selected from RNase A, RNase C, RNase H, and RNase I.

15. The method of claim 1, wherein the one or more nucleic acid probes directly hybridize to a first nucleic acid in the set of first nucleic acids or a complement thereof.

16. The method of claim 15, wherein a nucleic acid probe of the one or more nucleic acid probes comprises a padlock probe, a circular probe, or a circularized probe.

17. The method of claim 1, wherein the one or more nucleic acid probes indirectly hybridize to a first nucleic acid in the set of first nucleic acids or a complement thereof.

18. The method of claim 1, wherein the tissue sample is a tissue section, optionally wherein the tissue section is a fixed tissue section or a fresh frozen tissue section.

19. The method of claim 1, wherein the capture probe comprises a poly (T) sequence, one or more functional domains, a unique molecular identifier (UMI), a cleavage domain, or a combination thereof.

20. The method of claim 1, wherein step (c) comprises sequential hybridization of a plurality of labelled probes to the one or more nucleic acid probes.

21. The method of claim 1, wherein the one or more nucleic acid probes comprise a primary probe that directly hybridizes to a first nucleic acid in the set of first nucleic acids or a complement thereof.

22. The method of claim 21, wherein step (c) comprises amplifying the primary probe and contacting the permeabilized tissue sample with one or more detectably labelled probes capable of directly or indirectly hybridizing to the primary probe or a complement thereof or an amplification product thereof, optionally wherein the one or more detectably labelled probes hybridize to one or more barcode sequences of the primary probe or the complement thereof or the amplification product thereof.

23. The method of claim 21, wherein step (c) comprises amplifying the primary probe and contacting the permeabilized tissue sample with one or more secondary probes capable of directly or indirectly hybridizing to the primary probe or a complement thereof or an amplification product thereof, optionally wherein the one or more secondary probes hybridize to one or more barcode sequences of the primary probe or the complement thereof or the amplification product thereof.

24. The method of claim 23, wherein step (c) further comprises contacting the permeabilized tissue sample with one or more detectably labelled probes capable of directly or indirectly hybridizing to the one or more secondary probes or complements thereof, optionally wherein the one or more detectably labelled probes hybridize to one or more barcode sequences of the one or more secondary probes or the complements thereof.

25. The method of claim 24, further comprising imaging the permeabilized tissue sample by detecting the one or more barcode sequences of the primary probe or the complements thereof, optionally by detecting the one or more barcode sequences of the one or more secondary probes or the complements thereof.

26. The method of claim 25, wherein the said detecting the one or more nucleic acid probes comprises sequencing (1) all or a part of the set of first nucleic acids or their complements thereof and/or (2) all or a part of the one or more nucleic acid probes by sequencing by ligation or sequencing by hybridization.

27. The method of claim 1, wherein said detecting the one or more nucleic acid probes comprises sequentially hybridizing a plurality of labelled probes to the one or more nucleic acid probes, wherein a labelled probe of the plurality of labelled probes comprises a fluorescent moiety, and wherein the method further comprises imaging the permeabilized tissue sample by detecting a fluorescent signal generated from the fluorescent moiety.

\* \* \* \* \*